US010270484B2

(12) United States Patent
Lambert et al.

(10) Patent No.: US 10,270,484 B2
(45) Date of Patent: Apr. 23, 2019

(54) STERILIZABLE ENCLOSURE FOR SECURING A PORTABLE ELECTRONIC DEVICE

(71) Applicant: Stryker Corporation, Kalamazoo, MI (US)

(72) Inventors: Trevor Jonathan Lambert, Portage, MI (US); Robert Kenneth Alexander, Portage, MI (US); Bruce D. Henniges, Galesburg, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/761,916

(22) PCT Filed: Oct. 5, 2016

(86) PCT No.: PCT/US2016/055518
§ 371 (c)(1),
(2) Date: Mar. 21, 2018

(87) PCT Pub. No.: WO2017/062466
PCT Pub. Date: Apr. 13, 2017

(65) Prior Publication Data
US 2018/0234127 A1 Aug. 16, 2018

Related U.S. Application Data

(60) Provisional application No. 62/237,315, filed on Oct. 5, 2015.

(51) Int. Cl.
*A61L 2/07* (2006.01)
*A61L 2/10* (2006.01)
(Continued)

(52) U.S. Cl.
CPC ............ *H04B 1/3888* (2013.01); *A45C 11/00* (2013.01); *A61L 2/07* (2013.01); *A61L 2/26* (2013.01);
(Continued)

(58) Field of Classification Search
CPC . H04B 1/3888; A61L 2/07; A61L 2/26; A61L 2202/182; A61L 2/10; A61L 2/18;
(Continued)

(56) References Cited

U.S. PATENT DOCUMENTS 5,534,221 A * 7/1996 Hillebrenner .......... A61B 1/125
206/438
5,812,188 A 9/1998 Adair
(Continued)

FOREIGN PATENT DOCUMENTS

| EP | 2180773 A1 | 4/2010 |
|----|------------|--------|
| GB | 2483309 A  | 3/2012 |

(Continued)

OTHER PUBLICATIONS

International Search Report for Application No. PCT/US2016/055518 dated Aug. 17, 2017, 4 pages.
(Continued)

*Primary Examiner* — Lewis G West
(74) *Attorney, Agent, or Firm* — Howard & Howard Attorneys PLLC

(57) ABSTRACT

A sterilizable enclosure for securing a portable electronic device having a touchscreen and for preventing ingress and egress of contaminants to and from the secured device, comprising a frame with a frame periphery edge, the frame defining a window with a transparent panel adjacent the window arranged to abut the touchscreen. A base coupled to the frame comprises a base periphery edge and cooperates with the frame to define a closed position in which the
(Continued)

device is secured between the base and the frame. A seal comprising a seal periphery edge is attached to at least one of the base and the frame and is arranged to be engaged between the base and the frame when the enclosure is closed to prevent ingress and egress of contaminants to and from the secured device with the seal periphery edge adjacent to the frame periphery edge and base periphery edge.

19 Claims, 57 Drawing Sheets

(51) Int. Cl.
*A61L 2/18* (2006.01)
*A61L 2/26* (2006.01)
*A45C 11/00* (2006.01)
*H04B 1/3888* (2015.01)

(52) U.S. Cl.
CPC ... *A45C 2011/002* (2013.01); *A45C 2011/003* (2013.01); *A45C 2200/10* (2013.01); *A61L 2/10* (2013.01); *A61L 2/18* (2013.01); *A61L 2202/182* (2013.01); *G06F 2200/1633* (2013.01)

(58) Field of Classification Search
CPC ........... A45C 2200/10; A45C 2011/003; G06F 2200/1633
See application file for complete search history.

(56) References Cited

U.S. PATENT DOCUMENTS

| | | | |
|---|---|---|---|
| 6,034,622 A * | 3/2000 | Levine | A61B 5/0031 340/3.7 |
| 6,845,775 B1 | 1/2005 | Barthes | |
| 7,194,202 B2 | 3/2007 | Funahashi et al. | |
| 7,389,872 B2 | 6/2008 | Wheeler et al. | |
| 7,424,314 B2 * | 9/2008 | Park | H04M 1/17 379/452 |
| 7,609,512 B2 | 10/2009 | Richardson et al. | |
| 8,203,124 B2 * | 6/2012 | Havens | A61L 2/10 250/455.11 |
| 8,475,365 B2 | 7/2013 | Modin et al. | |
| 8,597,569 B2 | 12/2013 | Gruen et al. | |
| 8,964,405 B2 * | 2/2015 | La Porte | A61L 2/10 361/807 |
| 9,010,537 B2 | 4/2015 | Carnevali | |
| 2002/0009195 A1 * | 1/2002 | Schon | B60R 11/0241 379/454 |
| 2003/0205029 A1 | 11/2003 | Chapolini et al. | |
| 2004/0147293 A1 * | 7/2004 | Park | H04M 1/04 455/573 |
| 2010/0096963 A1 * | 4/2010 | McLaughlin | G06F 1/1626 312/223.1 |
| 2012/0008880 A1 | 1/2012 | Toth | |
| 2012/0043235 A1 | 2/2012 | Klement | |
| 2013/0063922 A1 * | 3/2013 | La Porte | A61L 2/10 361/807 |
| 2013/0186798 A1 | 7/2013 | Naor | |
| 2014/0151247 A1 | 6/2014 | Rolf | |
| 2014/0332417 A1 * | 11/2014 | Wicks | H04B 1/3888 206/37 |
| 2015/0096963 A1 | 4/2015 | Bruck et al. | |
| 2015/0271308 A1 | 9/2015 | Roessler et al. | |
| 2015/0374868 A1 | 12/2015 | Bruce et al. | |
| 2016/0036952 A1 * | 2/2016 | Kim | A61L 2/10 455/575.8 |
| 2017/0360975 A1 * | 12/2017 | White | A61B 50/30 |
| 2018/0028703 A1 * | 2/2018 | McLaughlin | A61L 2/26 |

FOREIGN PATENT DOCUMENTS

| | | |
|---|---|---|
| WO | 2017051143 A2 | 3/2017 |
| WO | 2017051144 A1 | 3/2017 |

OTHER PUBLICATIONS

3D Techtronics, "Apple's Phil Schiller Says That Screen Guards Will Work with 3D Touch Display", Sep. 17, 2015, 1 page.
3M Company, "Technical Data—3M Quat Disinfectant Cleaner Concentrate 25A, 25L, and 25H", Apr. 2015, 4 pages.
9 to 5 MAC, "Seek Thermal Turns Your iPhone into a Thermographic Camera", Sep. 30, 2014, 2 pages.
Amazon, "JETech 2-pack Screen Protector for Apple Watch Reviews", 2015, 3 pages.
Apple, "Designing Accessories—Apple Developer", 2015, 2 pages.
Center for Disease Control, "Guideline for Disinfection and Sterilization in Healthcare Facilities", 2008, pp. 1-161.
Forbes Science, "3D Touch in iPhone 6S Isn't Just a Gimmick. Here's How it Works", Sep. 12, 2015, 6 pages.
Infection Control Today, "Preventing Infection Through Handwashing", Jun. 30, 2000, 9 pages.
Square Up, "Square Works for Every Business", Jun. 2015, 7 pages.

\* cited by examiner

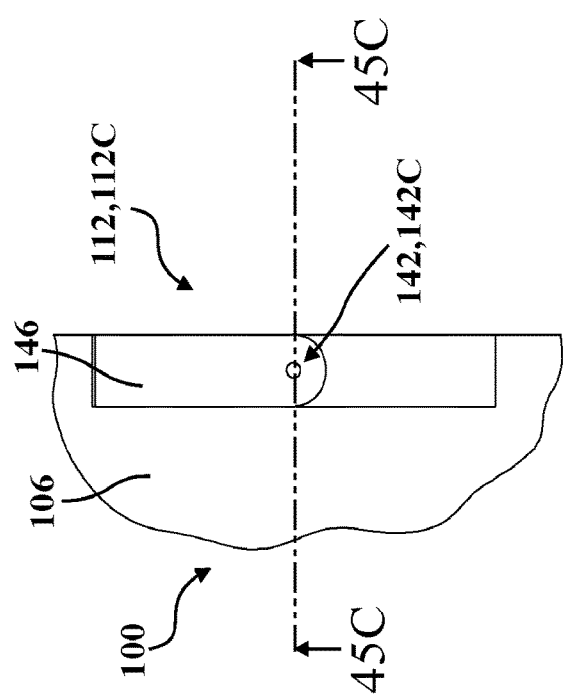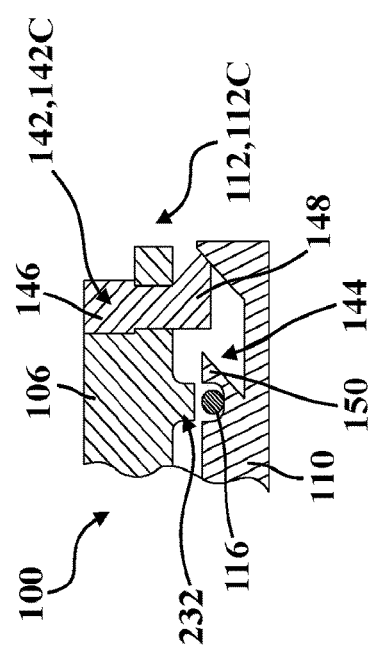

STERILIZABLE ENCLOSURE FOR SECURING A PORTABLE ELECTRONIC DEVICE

CROSS-REFERENCE TO RELATED APPLICATION

The subject patent application is the National Stage of International Patent Application No. PCT/US2016/055518, filed on Oct. 5, 2016, which claims priority to and all the benefits of U.S. Provisional Patent Application Ser. No. 62/237,315 which was filed on Oct. 5, 2015, the disclosure of which is hereby incorporated by reference.

TECHNICAL FIELD

The embodiments set forth herein relate, generally, to enclosures for portable electronic devices and, more specifically, to a sterilizable enclosure for securing a portable electronic device.

BACKGROUND

Portable electronic devices, such as iPad®s, tablet computers, cell phones, and the like are frequently utilized in a number of different environments and industries for facilitating communication and access to information. In the medical industry, portable electronic devices are increasingly utilized by medical professionals during triage, patient examination, and/or throughout the execution of medical procedures.

It will be appreciated that maintaining sterility and/or cleanliness in the medical industry is important in preventing the spread of communicable diseases, infection, pathogens, and the like. By way of example, medical procedures are typically performed in a sterile environment utilizing aseptically-packaged tools and materials in order to prevent inadvertent ingress of contaminants which could otherwise harm the patient or others. Further, it will be appreciated that minimizing transfer of contaminants is also important after a medical procedure has taken place in order to prevent inadvertent spread of contaminants which could otherwise harm others, such as where a medical professional has treated a highly-contagious patient.

Thus, in order to prevent transmission of contaminants, great care is taken to properly decontaminate reusable tools and equipment used in connection with treating a patient. To that end, various decontamination steps and procedures known in the art are utilized, such as manual washing, automatic washing with thermal disinfectant, steam sterilization (such as a pressurized chamber high-temperature steam autoclave), low-temperature sterilization (such as "Sterrad®"), point of contact chemical disinfection, application of disinfecting wipes and chemicals, and the like. These decontamination procedures are largely incompatible with conventional portable electronic devices, which are typically designed for general consumer use.

By way of example, portable electronic devices are often manufactured from materials that are incompatible with medical-grade cleaning and/or disinfectant agents. Further, portable electronic devices frequently include one or more connection ports that are open to the environment and cannot be exposed to liquids without causing irreversible damage. Similarly, while various shields, cases, and covers for portable electronic devices are known in the art, many are specifically designed for consumer use and are incompatible with one or more of the decontamination procedures described above, such as because of the presence of disadvantageous gaps or crevices, and may be expensive, difficult to use, or may otherwise restrict functionality of the portable electronic device in use.

For the foregoing reasons, there remains a need in the art for a sterilizable enclosure which prevents ingress and egress of contaminants to and from a secured portable electronic device and which strikes a substantial balance between usability, functionality, and manufacturing cost while, at the same time, affording compatibility with decontamination procedures commonly utilized in the medical industry.

SUMMARY

In one embodiment, a sterilizable enclosure is provided for use in securing a portable electronic device having a touchscreen interface and for preventing ingress and egress of contaminants to and from the secured portable electronic device. A frame comprising a frame periphery edge is provided. The frame defines a window, and a transparent panel is operatively attached to the frame adjacent to the window. The transparent panel is arranged to abut the touchscreen interface of the portable electronic device. A base is provided for being coupled to the frame, and comprises a base periphery edge. The base and the frame cooperate to define a closed position of the sterilizable enclosure in which the portable electronic device is secured between the base and the frame. A seal is provided and comprises a seal periphery edge. The seal is operatively attached to at least one of the base and the frame, and is arranged to be engaged between the base and the frame when the sterilizable enclosure is in the closed position so as to prevent ingress and egress of contaminants to and from the secured portable electronic device. The seal periphery edge is arranged adjacent to the frame periphery edge and the base periphery edge.

In another embodiment, a sterilizable enclosure is provided for use in securing a portable electronic device having a touchscreen interface and for preventing ingress and egress of contaminants to and from the secured portable electronic device. A frame defining a window is provided. A base is provided for being coupled to the frame. The base and the frame cooperate to define a closed position of the sterilizable enclosure in which the portable electronic device is secured between the base and the frame. A lock mechanism is provided for selectively locking the sterilizable enclosure in the closed position. A glass panel is operatively attached to the frame adjacent to the window and is arranged to abut the touchscreen interface of the portable electronic device when the sterilizable enclosure is locked in the closed position. A seal is operatively attached to at least one of the base and the frame and is arranged to be engaged between the base and the frame when the sterilizable enclosure is locked in the closed position so as to prevent ingress and egress of contaminants to and from the secured portable electronic device. A biasing mechanism is operatively attached to the base to urge the touchscreen interface of the portable electronic device into abutment with the glass panel to enable a capacitive coupling between the glass panel and the touchscreen interface of the secured portable electronic device when the sterilizable enclosure is in the closed position.

In another embodiment, a sterilizable enclosure is provided for use in securing a portable electronic device having a touchscreen interface and for preventing ingress and egress of contaminants to and from the secured portable electronic device. A frame defining a window is provided. A base is provided for being coupled to the frame. The base and the frame cooperate to define a closed position of the sterilizable enclosure in which the portable electronic device is secured between the base and the frame. A lock mechanism is provided for selectively locking the sterilizable enclosure in the closed position. The lock mechanism comprises a lock element rotatably coupled to one of the base and the frame. A glass panel is operatively attached to the frame adjacent to the window and is arranged to abut the touchscreen interface of the portable electronic device when the sterilizable enclosure is locked in the closed position. A seal is operatively attached to at least one of the base and the frame. Rotation of the lock element of the lock mechanism from a first position to a second position urges the base and the frame towards each other to enable a capacitive coupling between the glass panel and the touchscreen interface of the secured portable electronic device and to engage the seal so as to prevent ingress and egress of contaminants to and from the secured portable electronic device.

In another embodiment, a sterilizable enclosure is provided for use in securing a portable electronic device having a touchscreen interface and for preventing ingress and egress of contaminants to and from the secured portable electronic device. A frame defining a window is provided, and a transparent panel is operatively attached to the frame adjacent to the window. The transparent panel is arranged to abut the touchscreen interface of the portable electronic device. A base is provided for being coupled to the frame. The base and the frame cooperate to define a closed position of the sterilizable enclosure in which the portable electronic device is secured between the base and the frame. A seal is operatively attached to one of the base and the frame and is arranged to be engaged between the base and the frame when the sterilizable enclosure is in the closed position so as to prevent ingress and egress of contaminants to and from the secured portable electronic device. An engagement element is operatively attached to the other of the base and the frame and is shaped to engage the seal when the sterilizable enclosure is in the closed position. The seal and the engagement element each define a boundary between: a touch zone comprising first portions of the base and the frame, and a no-touch zone comprising second portions of the base and the frame. An indicia is provided, and is configured to differentiate the first portions of the touch zone from the second portions of the no-touch zone so as to promote contact only within the first portions of the base and the frame of the sterilizable enclosure.

In another embodiment, a method is provided for securing a portable electronic device having a touchscreen interface for use in a sterile environment. The method comprises: providing a sterilizable enclosure comprising a frame defining a window with a transparent panel operatively attached to the frame adjacent to the window and arranged to abut the touchscreen interface of the portable electronic device, a base pivotally coupled to the frame, and a seal arranged to be engaged between the base and the frame when the sterilizable enclosure is in a closed position so as to prevent ingress and egress of contaminants to and from the secured portable electronic device; providing a transfer device configured to shield at least a portion of the sterilizable enclosure from contaminants while holding the sterilizable enclosure in an opened position with the frame pivoted away from the base; holding the sterilizable enclosure in the opened position with the transfer device; inserting the portable electronic device into the sterilizable enclosure while in the opened position; and moving the transfer device away from the sterilizable enclosure to allow the frame to move towards the base into the closed position.

The sterilizable enclosures prevent both ingress and egress of contaminants to and from a secured portable electronic device, thereby significantly contributing to sterility and affording increased opportunity for robust utilization of portable electronic devices in industry while, at the same time, reducing the cost and complexity of manufacturing, assembling, and using sterilizable enclosures. Sometimes, portable electronic devices are used in such a manner that classifies them as devices requiring routine decontamination to remove or kill micro-organisms, such as by chemical disinfectants. The sterilizable enclosures provide a solution to enable such decontamination procedures.

BRIEF DESCRIPTION OF THE DRAWINGS

FIG. 44C is another partial top-side view of the sterilizable enclosure of FIGS. 44A-44B, shown with the lock mechanism in an autoclave configuration.

FIG. 45C is a partial section view taken along line 45C-45C in FIG. 44C.

DETAILED DESCRIPTION

Figure 1:
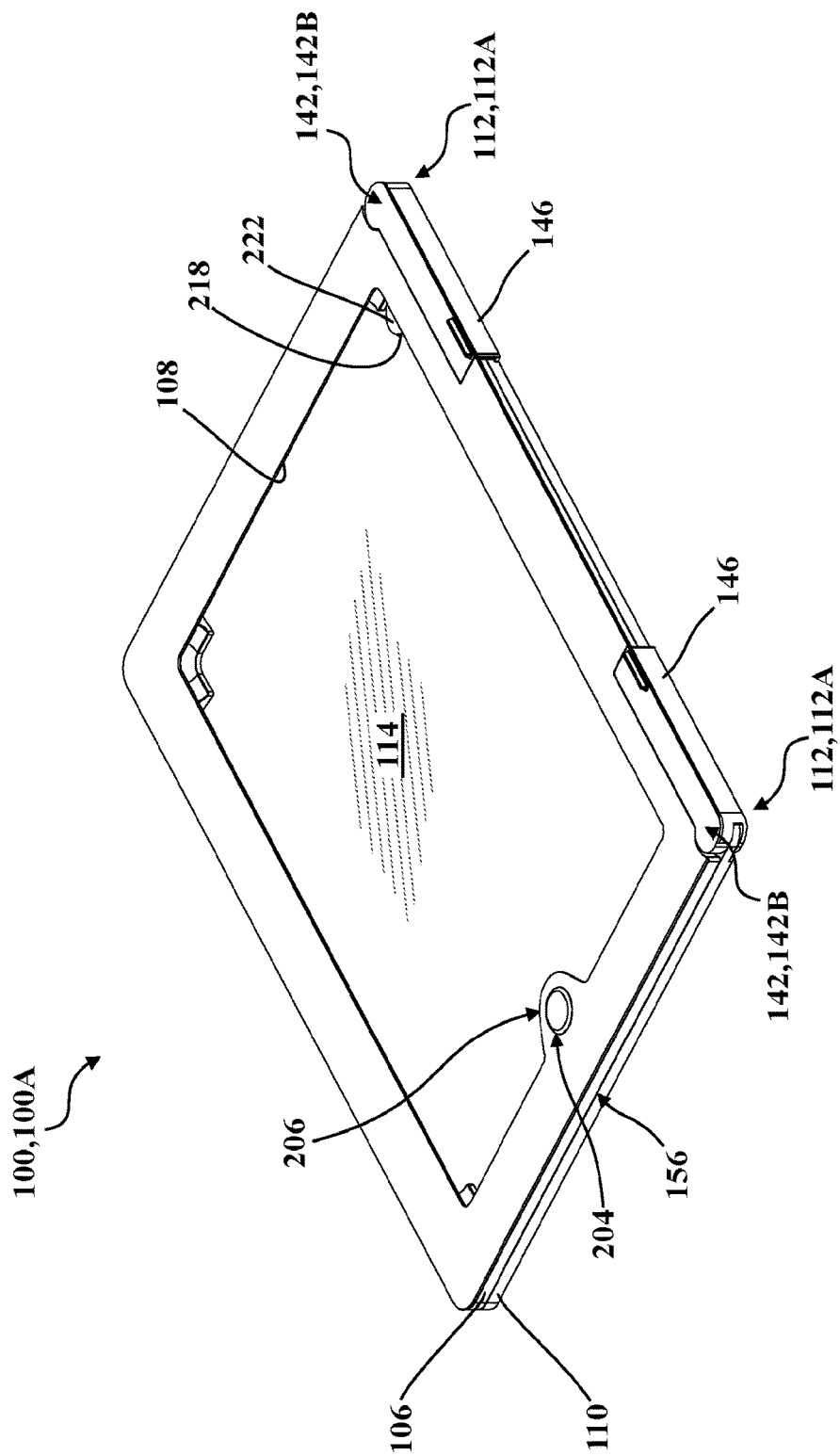
FIG. 1 is a top-side perspective view of a sterilizable enclosure according to one embodiment, showing a base pivotally coupled to a frame with the base and the frame arranged in a closed position, and a lock mechanism shown in a locked configuration.
Figure 2:
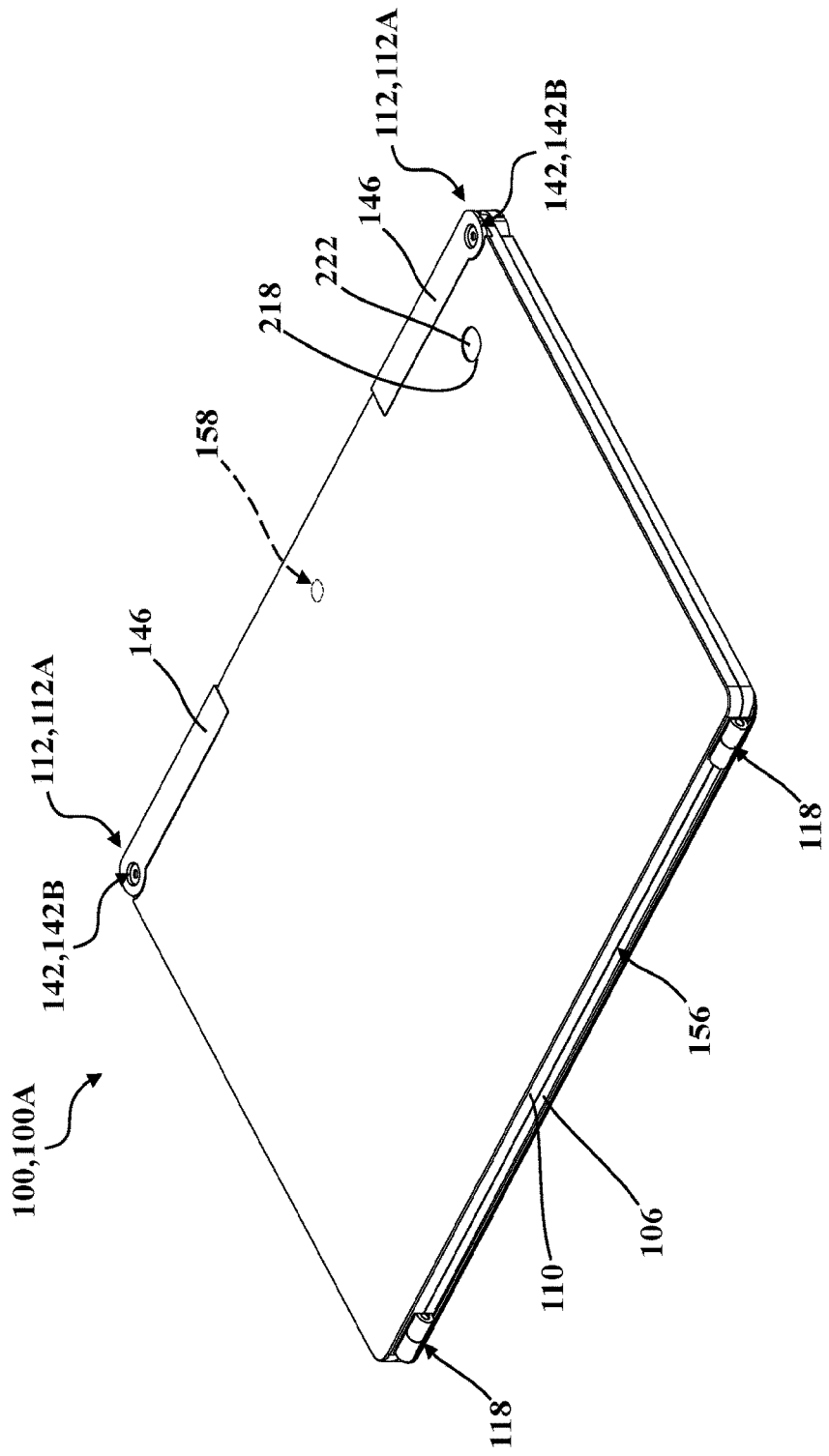
FIG. 2 is a bottom-side perspective view of the sterilizable enclosure of FIG. 1.
Figure 3:
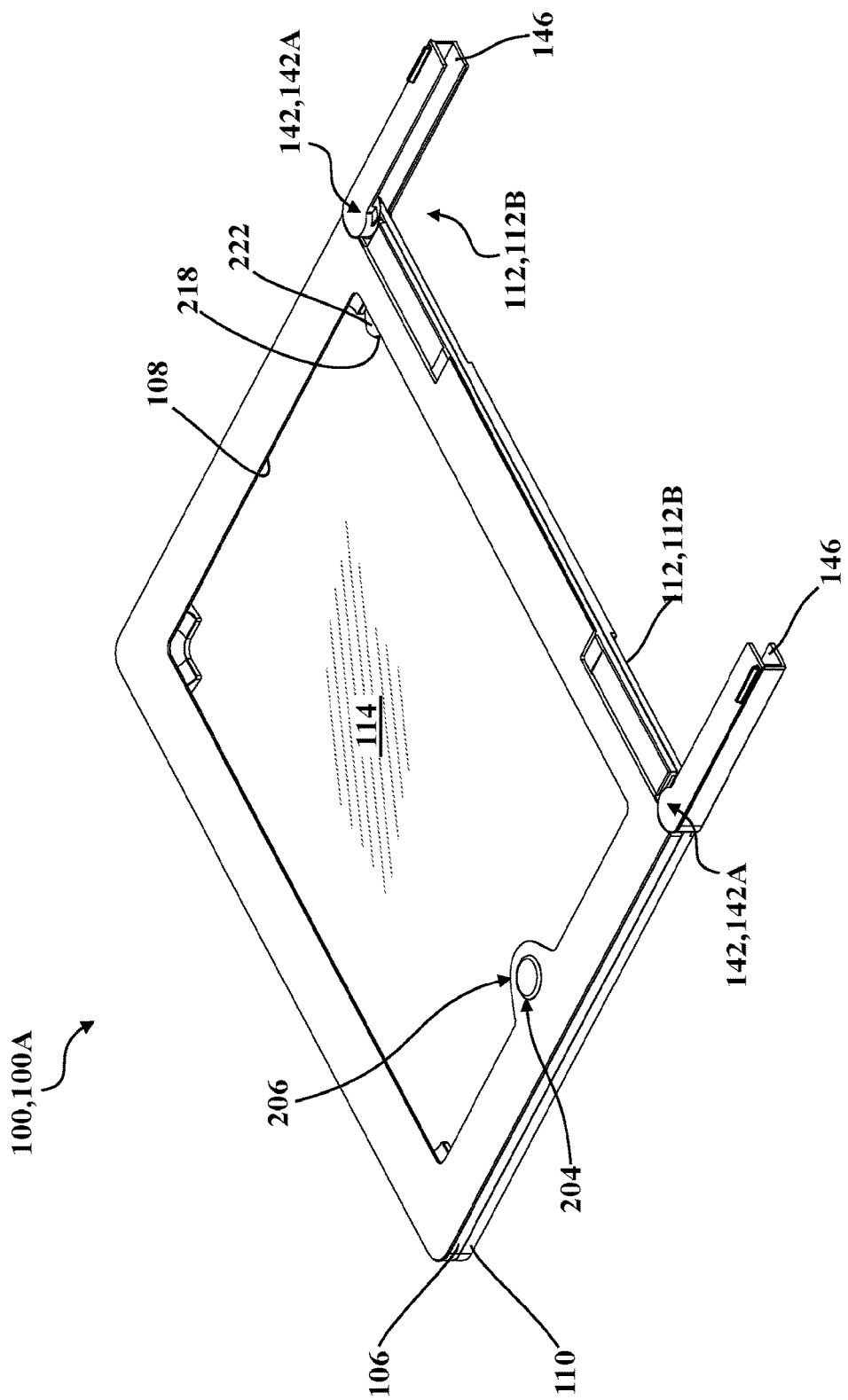
FIG. 3 is a top-side perspective view of the sterilizable enclosure of FIGS. 1-2, shown in the closed position and with the lock mechanism in an unlocked configuration.

With reference now to the drawings, wherein like numerals indicate like parts throughout the several views, a sterilizable enclosure is generally shown at 100 in FIGS. 1-20C. As described in greater detail below, the sterilizable enclosure 100 is adapted for use in securing a portable electronic device, generally indicated at 102, having a touchscreen interface 104 (see FIG. 5), and is further adapted to prevent ingress and egress of contaminants to and from the secured portable electronic device 102. To that end, the sterilizable enclosure 100 includes a frame, generally indicated at 106, which defines a window 108. A base, generally indicated at 110, is provided for being coupled to the frame 106. The base 110 and the frame 106 cooperate to define a closed position 100A of the sterilizable enclosure 100, in which the portable electronic device 102 is secured between the base 110 and the frame 106.

In the representative embodiment illustrated herein, the sterilizable enclosure 100 further comprises a lock mechanism, generally indicated at 112, operatively attached to the base 110 and the frame 106 for selectively locking the sterilizable enclosure 100 in the closed position 100A, as described in greater detail below. A transparent panel, such as glass panel 114, is operatively attached to the frame 106 adjacent to the window 108, and is arranged to abut the touchscreen interface 104 of the portable electronic device 102 when the sterilizable enclosure 100 is locked in the closed position 100A to effect a capacitive coupling between the glass panel 114 and the touchscreen interface 104. A seal 116 is operatively attached to at least one of the base 110 and the frame 106 and is arranged to be engaged between the base 110 and the frame 106 (for example, compressed between) when the sterilizable enclosure 100 is locked in the closed position 100A so as to prevent ingress and egress of contaminants to and from the secured portable electronic device 102. Each of these components will be described in greater detail below.

As will be appreciated from the subsequent description below, the present disclosure is directed, generally, towards two types of sterilizable enclosures: a first type in which the base 110 and the frame 106 are pivotally attached to each other via one or more hinges 118 (see the embodiments depicted in FIGS. 1-20, 23-24, and 26-27), and a second type without hinges (see the embodiments depicted in FIGS. 28-36 and 39-40). Moreover, those having ordinary skill in the art will appreciate that certain components, structures, and arrangements are common between the embodiments and may be interchanged between embodiments for certain applications, as is described in greater detail below.

In the embodiments illustrated herein, one or more, or even all, of the various components of the sterilizable enclosure 100 are capable of withstanding repeated steam sterilization in an autoclave, in which the sterilizable enclosure 100 is subjected to a temperature of 134 degrees Celsius for 3 minutes or subjected to a temperature of 121 degrees Celsius for 15 minutes. The components of the sterilizable enclosure 100 may also be configured to withstand chemical detergents used in cleaning medical/surgical equipment. In other embodiments, the sterilizable enclosure 100 may be configured to withstand all known sterilization and decontamination methods for medical equipment, or only specific sterilization methods and/or specific decontamination methods. In one embodiment, "withstand" means experiencing decontamination conditions without melting, deformation, or decomposition. Certain methods for decontamination may include manual wash, automatic wash (such as with thermal disinfectant), steam sterilization, low-temperature sterilization (such as Sterrad®), chemical disinfection (for example, point-of-contact), chemical and mechanical cleaning (such as with detergents and microfiber materials), and the like.

To this end, certain components of the sterilizable enclosure 100, such as the base 110 and/or the frame 106, may advantageously be manufactured from one or more materials that facilitate heat transfer of the secured portable electronic device 102 in operation. By way of non-limiting example, the base 110 and/or the frame 106 could be manufactured at least partially or fully from aluminum, stainless steel, magnesium, and the like. Moreover, other materials may be advantageously used, such as carbon-fiber, plastic, composites such as Raydel®, or combinations thereof, or any other suitable material. The "components" described above may include each and every piece of the sterilizable enclosure 100 described above, including but not limited to, the frame 106, the base 110, the seal 116, the transparent panel 114, etc. Furthermore, in certain embodiments, the sterilizable enclosure may consist of materials that have a melting point greater than 130 degrees Celsius. Moreover, as will be appreciated from the subsequent description below, certain components may comprise materials which have been treated, coated, etc. so as to effect antimicrobial properties. By way of non-limiting example, copper alloy coatings or plating may be applied to one or more of the components of the sterilizable enclosure 100 to promote or otherwise effect antimicrobial properties.

The portable electronic device 102 may be configured to interact with other computers, devices, systems, sensors, machines, and/or networks, such as via wireless communication over Bluetooth®, a WiFi™ Local Area Network (LAN), and the like. As shown best in FIGS. 5, 46, and 47, the portable electronic device 102 may also include one or more input controls 120, such as a "home button," for facilitating selective control of the portable electronic device 102 in addition to control afforded by the touchscreen interface 104. Moreover, the portable electronic device 102 could include one or more connection ports 122, such as a "charging port," a "headphone port," and/or a "data port," for connection to one or more electrical connectors or cables.

Figure 46:
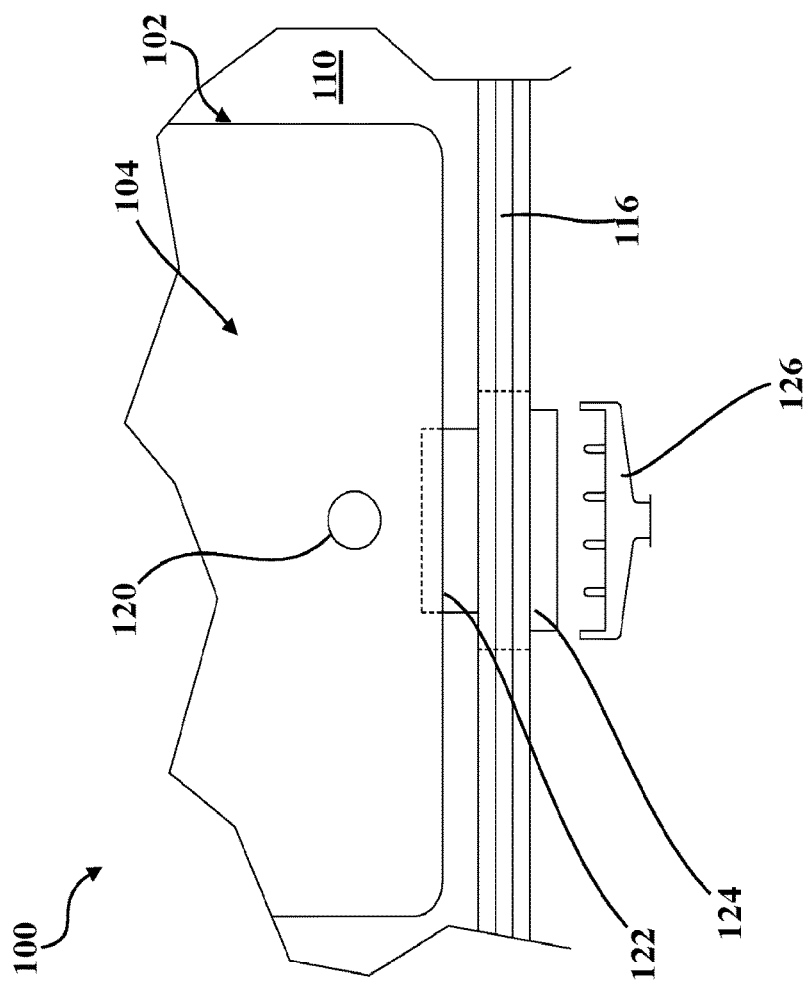
FIG. 46 is a partial top-side view of a sterilizable enclosure according to one embodiment, shown with a hermetically sealed connector operatively attached to a base positioned adjacent to a portable electronic device.
Figure 47:
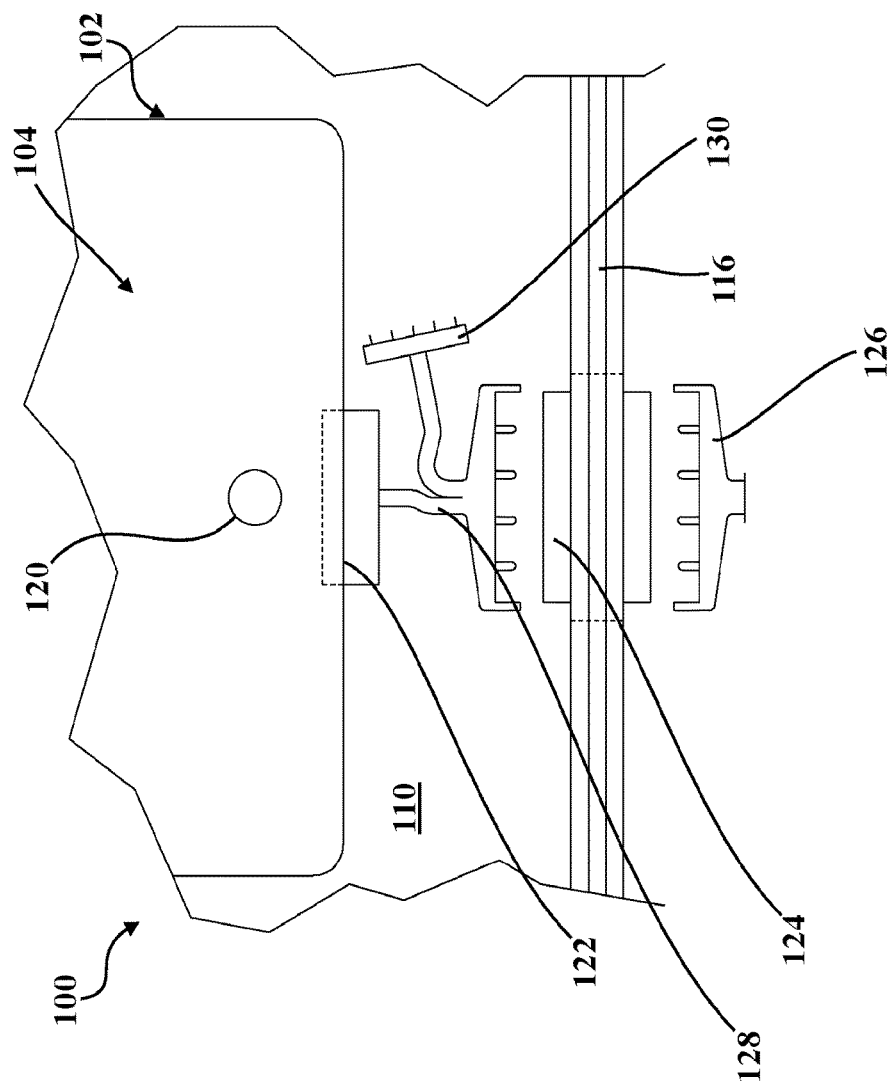
FIG. 47 is a partial top-side view of a sterilizable enclosure according to another embodiment, shown with a hermetically sealed connector, a harness, and an auxiliary cable operatively attached to a base positioned adjacent to a portable electronic device.

In the representative embodiment illustrated in FIGS. 46 and 47, the sterilizable enclosure 100 includes a hermetically sealed connector, generally indicated at 124, which is operatively attached to the base 110 and which is configured to facilitate electrical communication between the connection port 122 of the portable electronic device 102 and a cable 126 external to the sterilizable enclosure 100 and secured portable electronic device 102, which may advantageously be sterilizable. In the embodiment illustrated in FIG. 46, the portable electronic device 102 can be releasably attached directly to the sealed connector 124. In the embodiment illustrated in FIG. 47, the portable electronic device 102 can be releasably attached to a harness, generally indicated at 128, which, in turn, can be releasably (or, permanently) attached to the sealed connector 124. In this embodiment, the harness 128 further comprises an auxiliary cable, generally indicated at 130, which may be disposed in electrical communication with the sealed connector 124 and/or the connection port 122. Here, the auxiliary cable 130 may be adapted for connection to other components which may be operatively attached to or otherwise integrated with the sterilizable enclosure 100, such as one or more sensors, data transmission modules, power sources or batteries, inductive-charging modules, cameras, scanners (for example, a barcode scanner or an RFID scanner), and the like. Like the sealed connector 124, the harness 128 and the auxiliary cable 130 are similarly arranged to be isolated from the outside environment when the portable electronic device 102 is secured in the sterilizable enclosure 100 when locked in the closed position 100A, as is described in greater detail below.

Figure 19:
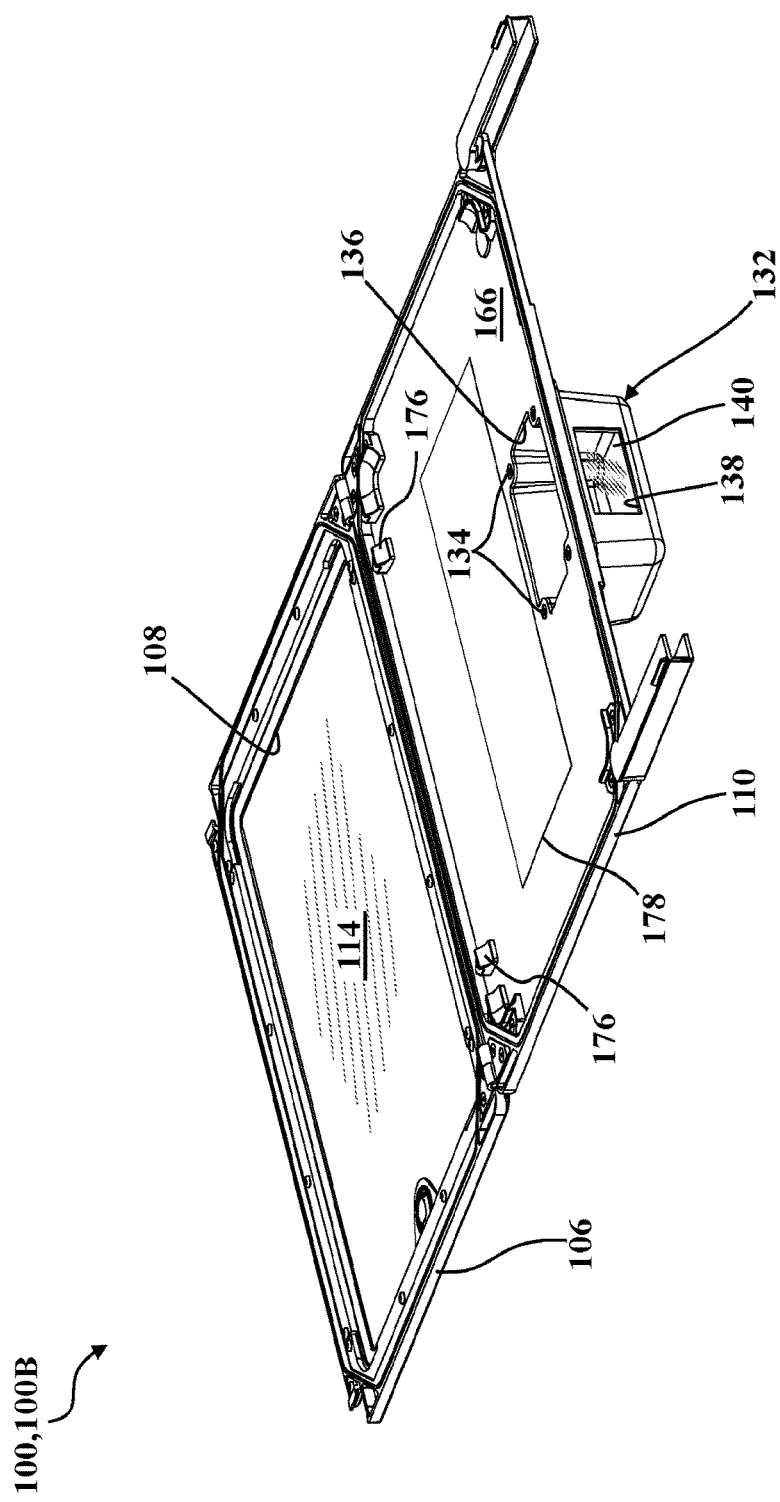
FIG. 19 is a top-side perspective view of another embodiment of the sterilizable enclosure depicted in FIGS. 1-18E, shown with an auxiliary housing operatively attached to and in communication with the base.

In the embodiment illustrated in FIG. 19, the sterilizable enclosure 100 further comprises an auxiliary housing, generally indicated at 132, which may be employed to accommodate one or more of the components noted above in connection with the auxiliary cable 130. The auxiliary housing 132 has a generally hollow configuration, is operatively attached to the base 110 via fasteners 134, and is disposed in communication with an auxiliary aperture 136 defined in the base 110. An auxiliary seal (not shown) may be provided to facilitate connection of the auxiliary housing 132 to the base 110 and to prevent ingress and/or egress of contaminants adjacent the auxiliary housing 132. It will be appreciated that the auxiliary housing 132 could alternatively be formed integrally with the housing 132.

As illustrated in FIG. 19, in one embodiment, the auxiliary housing 132 defines a sensor window 138 in which a sensor panel 140 is supported. Here, the sensor panel 140 is configured to allow light transmission thereacross, which may be advantageous for certain applications, such as where the auxiliary housing 132 accommodates a barcode scanner. The sensor panel 140 could be manufactured from any suitable material sufficient to transmit light, such as glass, sapphire, quartz, plastic, and the like, and also withstand conditions of the various decontamination procedures described herein. In certain embodiments, the auxiliary housing 132 may comprise materials that allow various forms of electromagnetic communication to pass therethrough, such as ultraviolet radiation, infrared radiation, and the like. It will be appreciated that the sensor panel 140 and the auxiliary housing 132 could be secured to any suitable portion of the sterilizable enclosure 100 in any way sufficient to prevent ingress and egress of contaminants to and from the secured portable electronic device 102. Moreover, it will be appreciated that the auxiliary housing 132, sensor panel 140, sealed connector 124, cable 126, harness 128, and/or auxiliary cable 130 could be used in connection with other embodiments described herein without limitation.

In the representative embodiments depicted throughout the drawings, the touchscreen interface 104 of the portable electronic device 102 is realized as a so-called "capacitive touch" interface (not shown in detail, but generally known in the related art). Here, in one embodiment, the glass panel 114 is arranged such that external tactile engagement by a user on an outwardly facing side of the glass panel 114 is at least partially translated to an electrostatic field of the portable electronic device 102 via interaction with a conductive object (not shown, but generally known in the art), such as a finger or stylus, when the sterilizable enclosure 100 is locked in the closed position 100A. It will be appreciated that the portable electronic device 102 itself is not a component of the sterilizable enclosure 100 and, thus, could employ any suitable type of touchscreen interface 104. Similarly, it will be appreciated that the portable electronic device 102 could be of any suitable size, type, or configuration sufficient to be secured by the sterilizable enclosure 100. By way of non-limiting example, the portable electronic device 102 could be an iPad®, a tablet computer, a cell phone, or any other type of portable electronic device that employs a touchscreen interface 104. Furthermore, in some alternative embodiments, the portable electronic device 102 may include other types of user interfaces.

Referring again to FIGS. 1-20C, as noted above, the lock mechanism 112 is provided for selectively locking the sterilizable enclosure 100 in the closed position 100A. To this end, in one embodiment, the lock mechanism 112 includes a first lock element 142 rotatably coupled to one of the base 110 and the frame 106, and a second lock element 144 operatively attached to the other of the base 110 and the frame 106. As is best illustrated in FIGS. 18A-18E, rotation of the first lock element 142 from a first position 142A (see FIGS. 18A and 18B) to a second position 142B (see FIG. 18E; compare with FIGS. 18A-18D) urges the base 110 and the frame 106 towards each other to enable a capacitive coupling between the glass panel 114 and the touchscreen interface 104 of the secured portable electronic device 102, and to engage the seal 116 so as to prevent ingress and egress of contaminants to and from the secured portable electronic device 102.

In the representative embodiment illustrated herein, the first lock element 142 and the second lock element 144 of the lock mechanism 112 cooperate to selectively lock the sterilizable enclosure 100 in the closed position 100A. To this end, the first lock element 142 comprises a latch 146 and a cam 148, and the second lock element 144 comprises a catch 150. Here, the latch 146 has an elongated, generally C-shaped profile and is rotatably coupled to the base 110 via a fastener 134 with a washer 152 arranged between the latch 146 and the base 110 (see FIGS. 17A and 17B). Those having ordinary skill in the art will appreciate that the C-shaped profile of the latch 148 helps promote engagement of the seal 116 when locked in the closed position 100A, as noted above. In the representative embodiment illustrated herein, the first lock element 142 is realized as a unitary, one-piece component such that the cam 148 and the latch 146 are integrally formed and, thus, rotate concurrently between the first position 142A (see FIGS. 17A and 18A) and the second position 142B (see FIGS. 17B and 18B). The catch 150, in turn, is operatively attached to the frame 106 via a fastener 134 and is shaped so as to engage the cam 148 of the first lock element 142 such that rotation of the first lock element 142 towards the second position 142B urges the frame 106 towards the base 110 as a result of the engagement between the cam 148 and the catch 150. As is best shown in FIGS. 18A-18D, a recess 154 is defined in the frame 106 adjacent to the catch 150 and is shaped complimentarily to the latch 146 of the first lock element 142. It will be appreciated that this configuration affords the sterilizable enclosure 100 with a substantially contiguous external surface 156 when locked in the closed position 100A (see FIGS. 1 and 2). It will be appreciated that other configurations of the lock mechanism 112 may be used with various embodiments of the sterilizable enclosure 100.

In the embodiments of the sterilizable enclosure 100 depicted herein which utilize the hinge 118 to pivotally couple the base 110 and the frame 106, both the first lock element 142 and the second lock element 144 are disposed outside of the seal 116 so that the seal 116 is positioned between the lock mechanism 112 and the secured portable electronic device 102. It will be appreciated that this configuration reduces the number of available leak paths to the secured portable electronic device 102 from the outside environment, or vice versa. In other words, the seal 116 is not interrupted by the lock mechanism 112 or the hinge 118. It will be appreciated that the hinges 118 and/or lock mechanisms 112 could be configured in a number of different ways. In the embodiments depicted with hinges 118, the sterilizable enclosure 100 is provided with a pair of first lock elements 142 and a corresponding pair of second lock elements 144, whereby the cams 148 cooperate with the respective catches 150 to selectively lock the sterilizable enclosure 100 in the closed position 100A. However, as will be appreciated from the subsequent description below, the lock mechanism 112 could have any suitable configuration sufficient to secure the base 110 and the frame 106 in the closed position 110A to effect the capacitive coupling and seal 116 engagement described above and, thus, the lock mechanism 112 could be operatively attached to or otherwise formed integrally with the base 110 and/or the frame 106 in any suitable way.

Figure 17A:
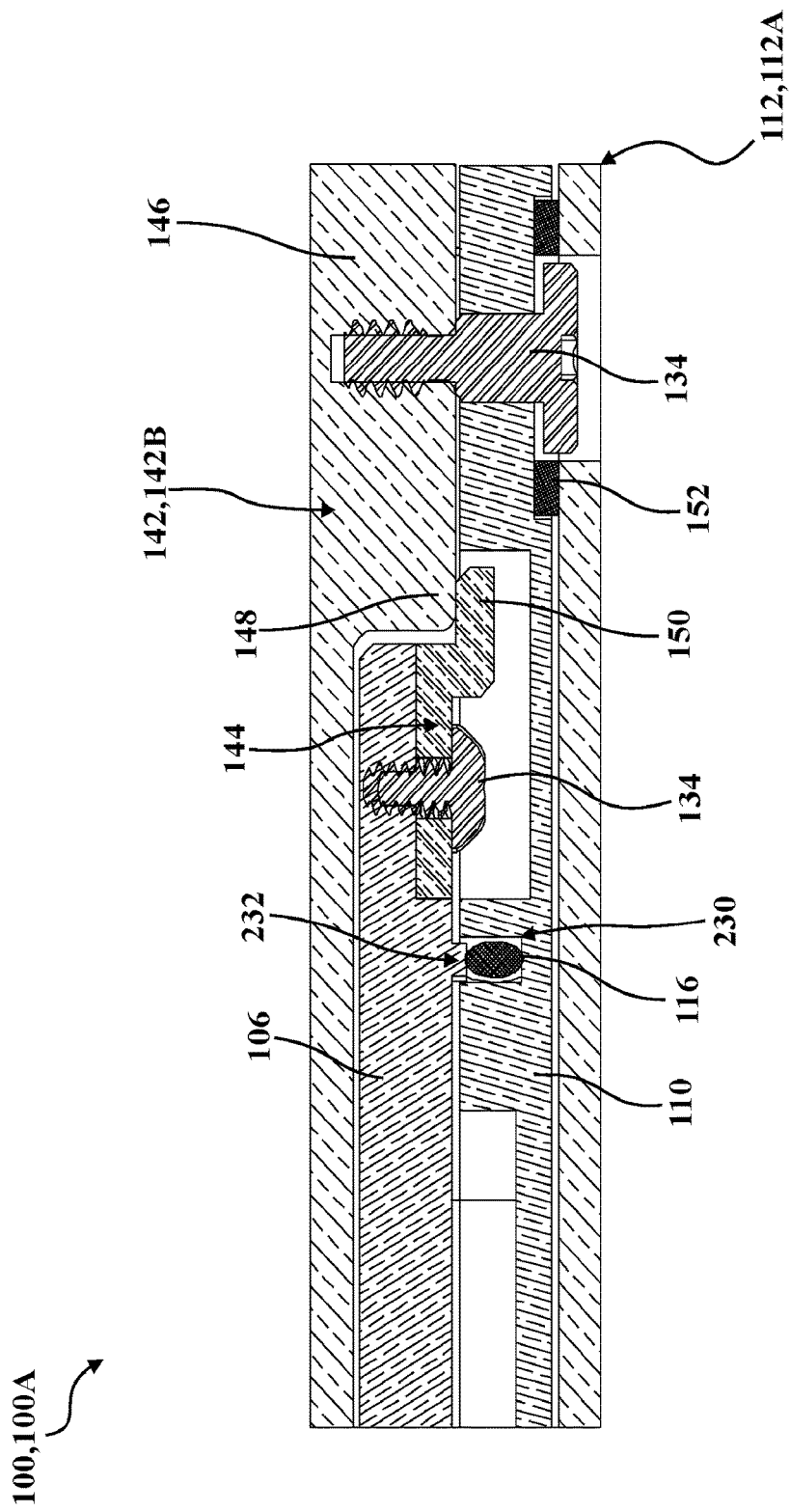
FIG. 17A is an offset sectional view taken along line 17A-17A of FIG. 11, shown with the lock mechanism in the locked configuration.
Figure 17B:
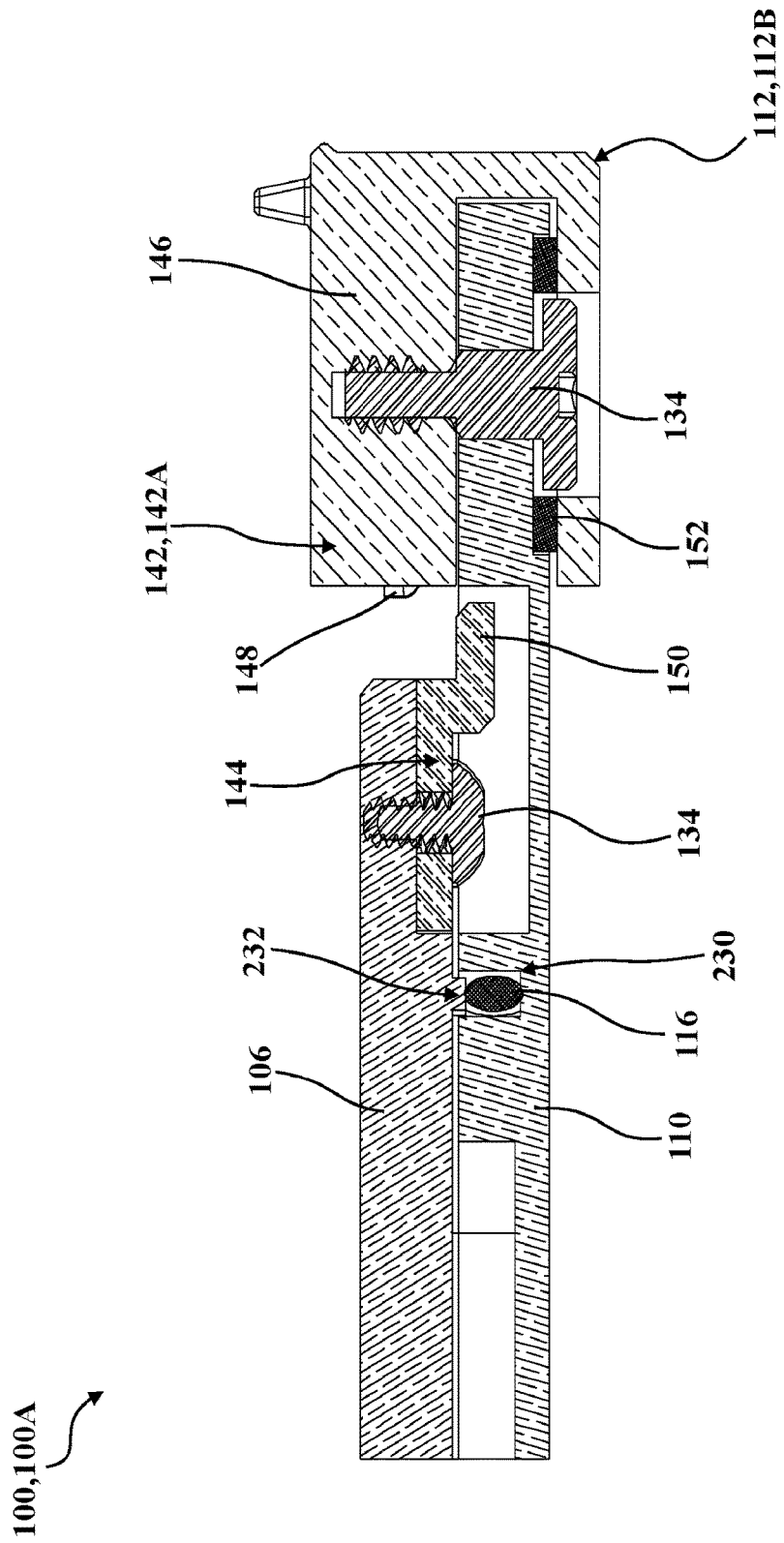
FIG. 17B is an offset sectional view of the sterilizable enclosure of FIG. 17A showing the lock mechanism in the unlocked configuration.
Figure 18A:
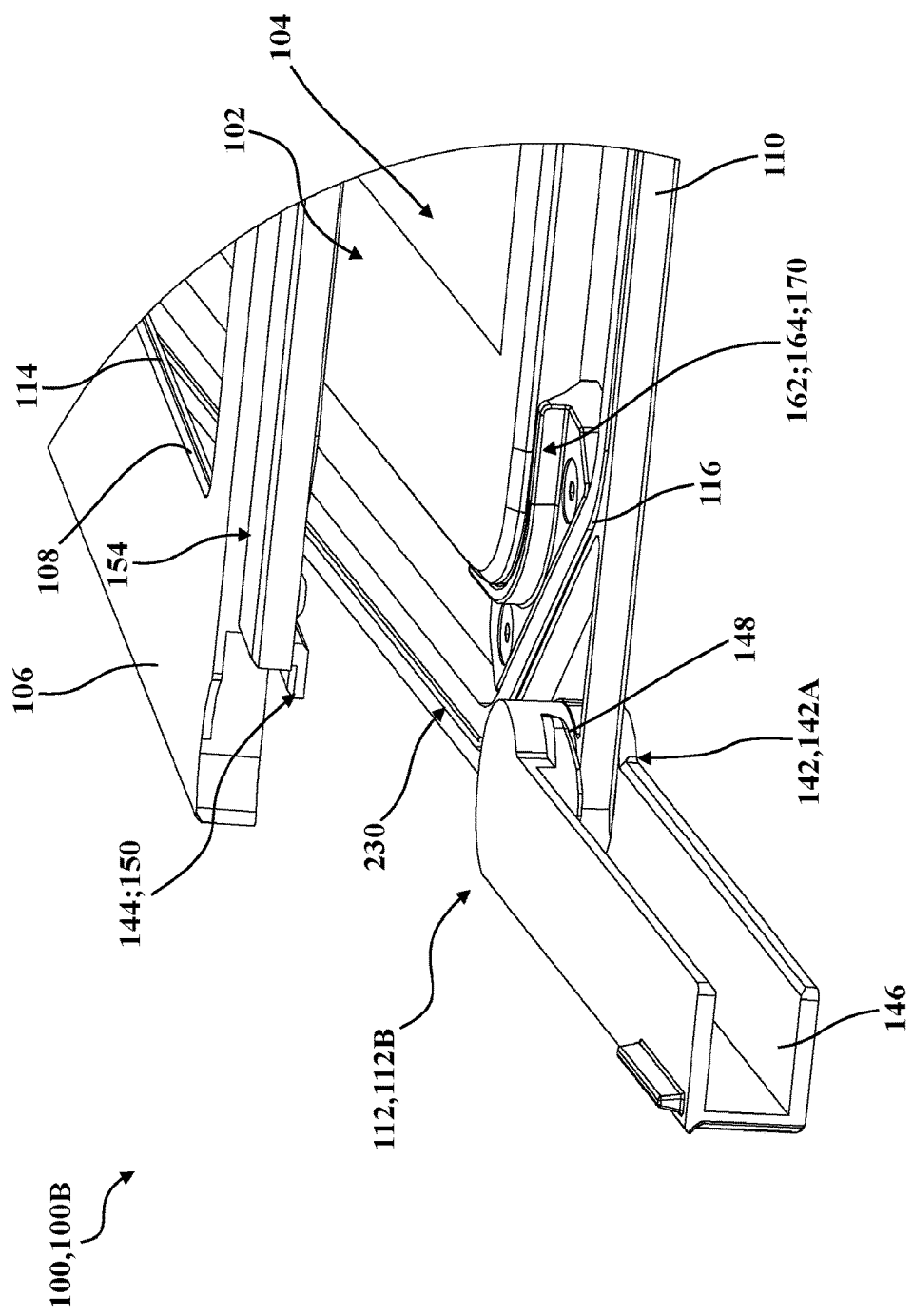
FIG. 18A is a partial perspective view of the portable electronic device seated in the base of the sterilizable enclosure of FIG. 6, shown with the lock mechanism in the unlocked configuration and with the frame spaced from and adjacent to the base, the lock mechanism depicted with a catch and with a lock element shown in a first position.
Figure 18B:
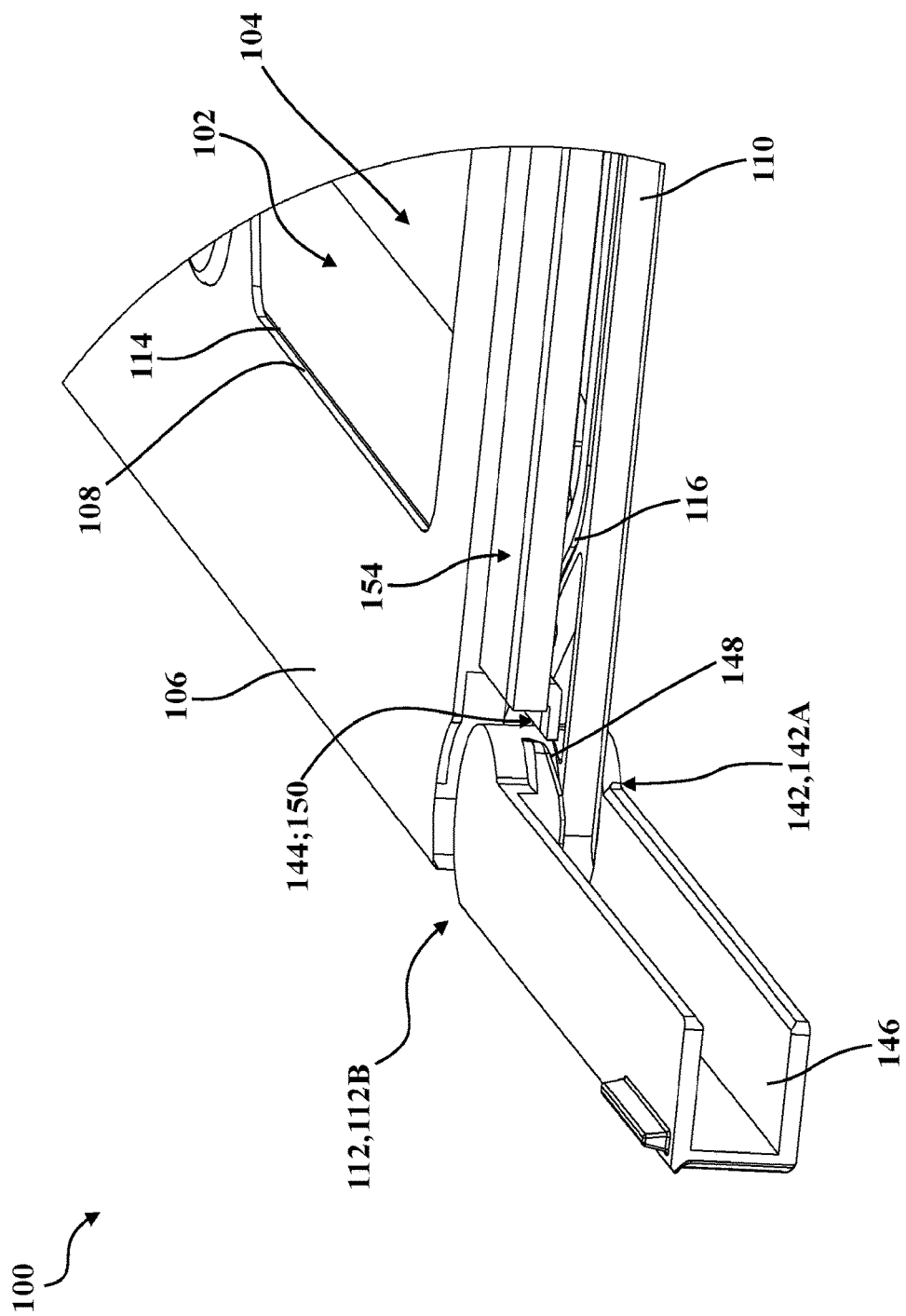
FIG. 18B is another partial perspective view of the portable electronic device and sterilizable enclosure of FIG. 18A, shown with the frame spaced closer to the base than as depicted in FIG. 18A.
Figure 18C:
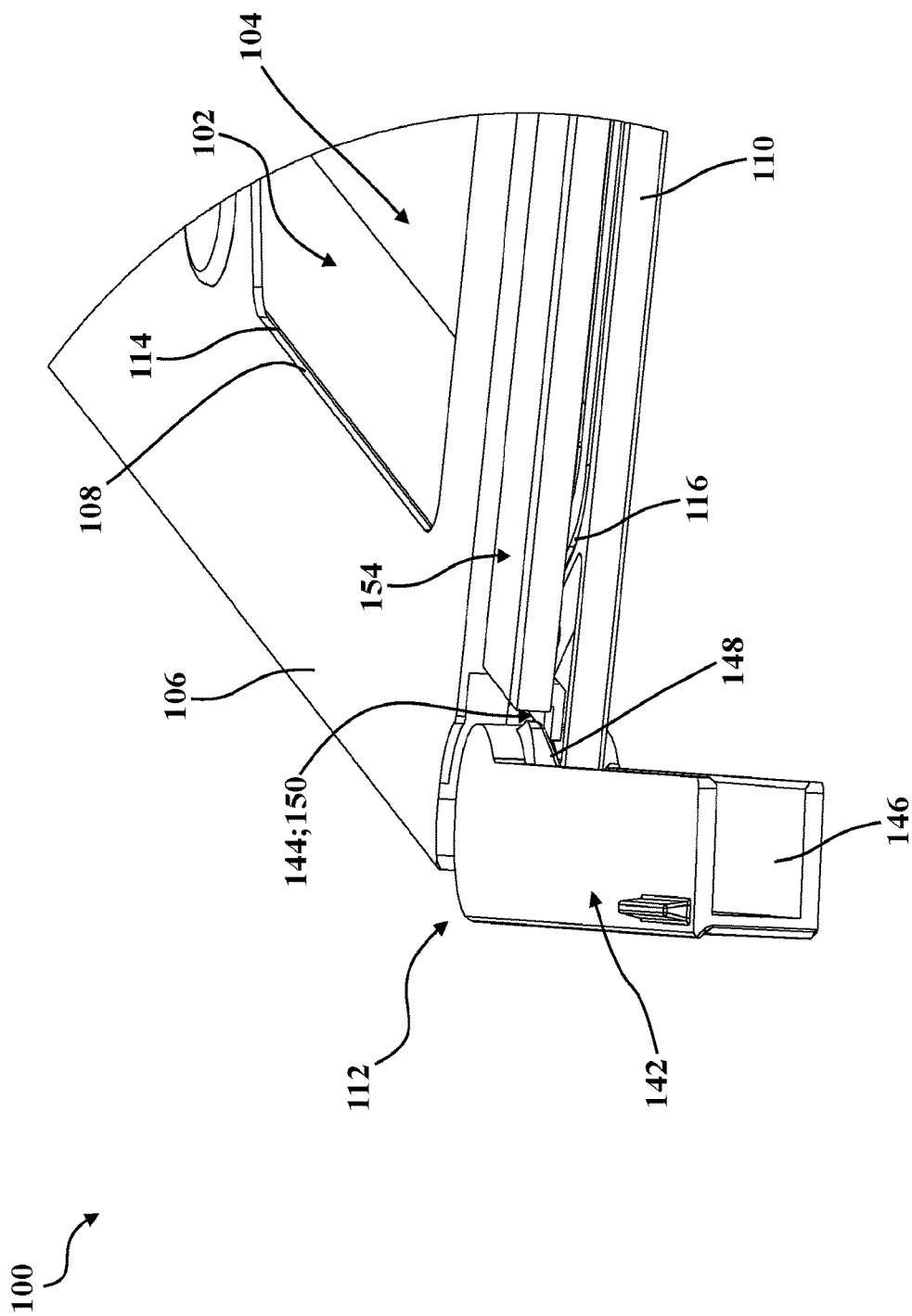
FIG. 18C is another partial perspective view of the portable electronic device and sterilizable enclosure of FIGS. 18A-18B, shown with the lock element rotated away from the first position as depicted in FIGS. 18A-18B.
Figure 18D:
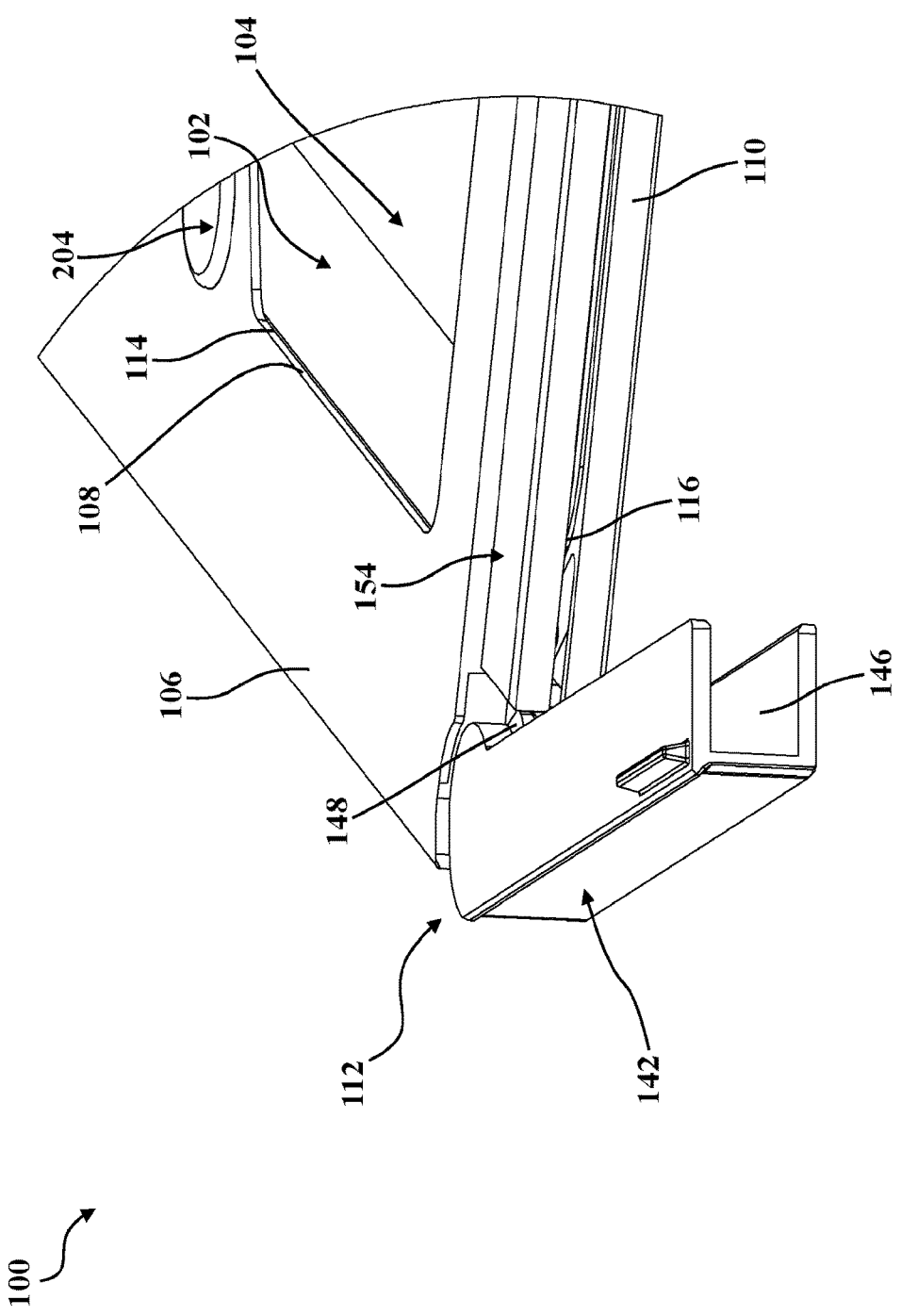
FIG. 18D is another partial perspective view of the portable electronic device and sterilizable enclosure of FIGS. 18A-18C, shown with the lock element rotated further away from the first position than as depicted in FIG. 18C.
Figure 18E:
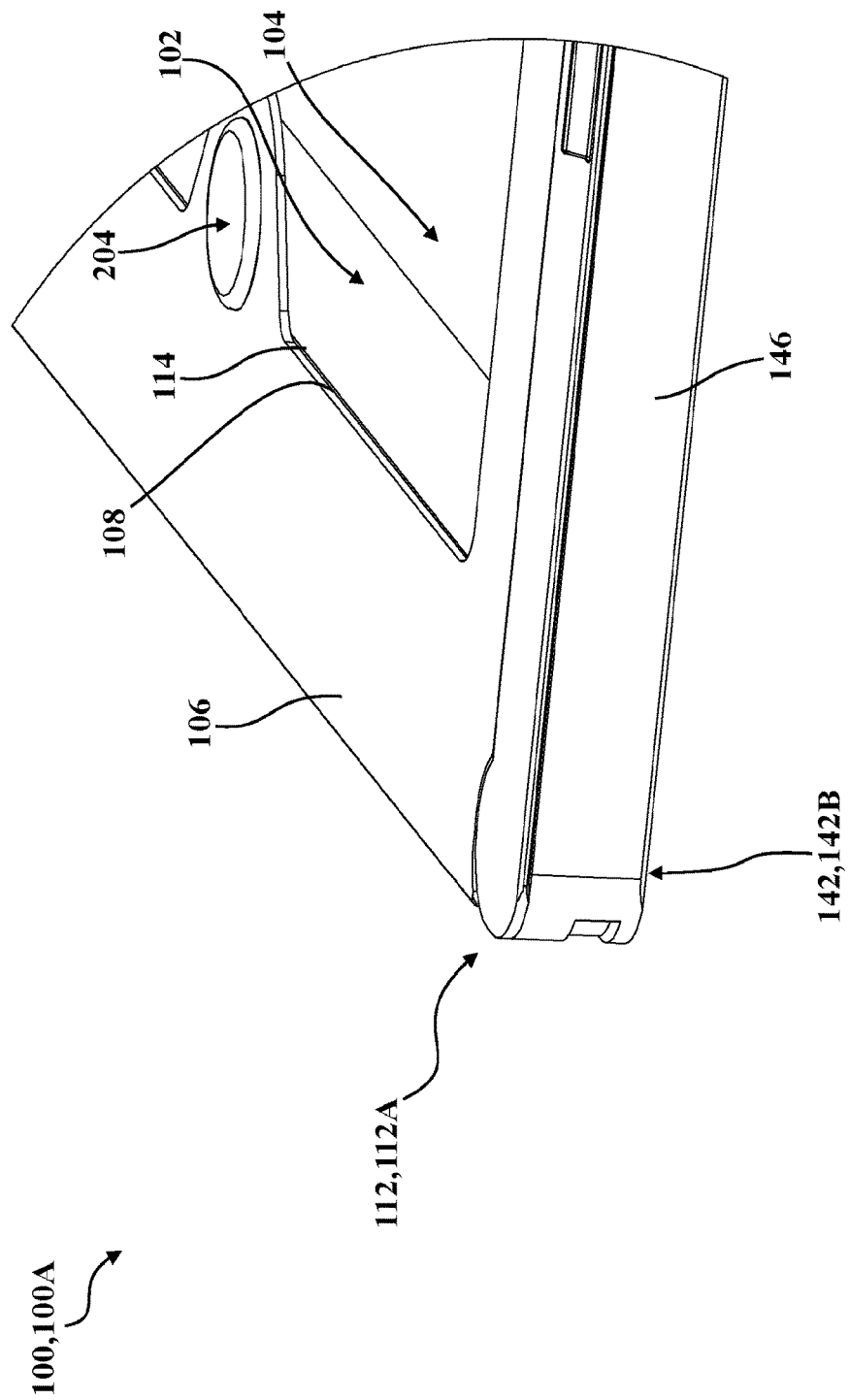
FIG. 18E is another partial perspective view of the portable electronic device and sterilizable enclosure of FIGS. 18A-18D, shown in the closed position with the lock mechanism in the unlocked configuration and with the lock element in a second position.
Figure 44A:
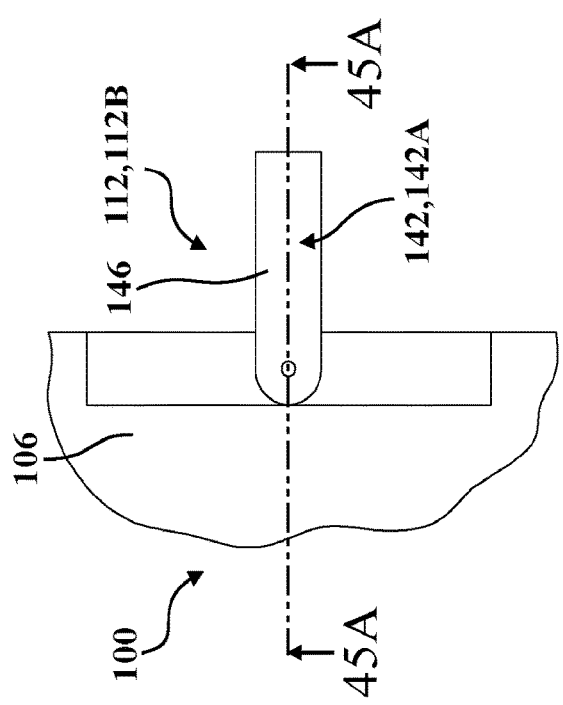
FIG. 44A is a partial top-side view of a sterilizable enclosure according to one embodiment, shown having a lock mechanism in an unlocked neutral configuration.
Figure 45A:
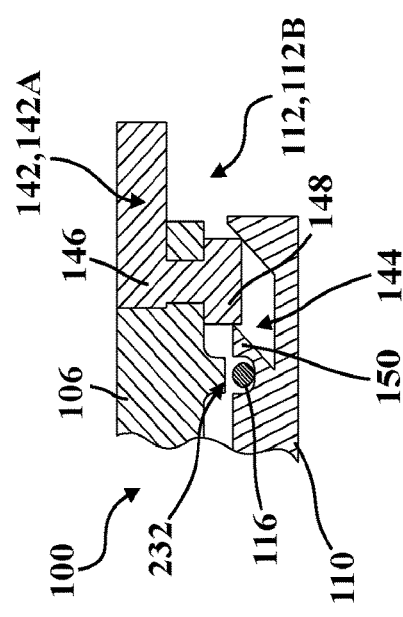
FIG. 45A is a partial section view taken along line 45A-45A in FIG. 44A.
Figure 44B:
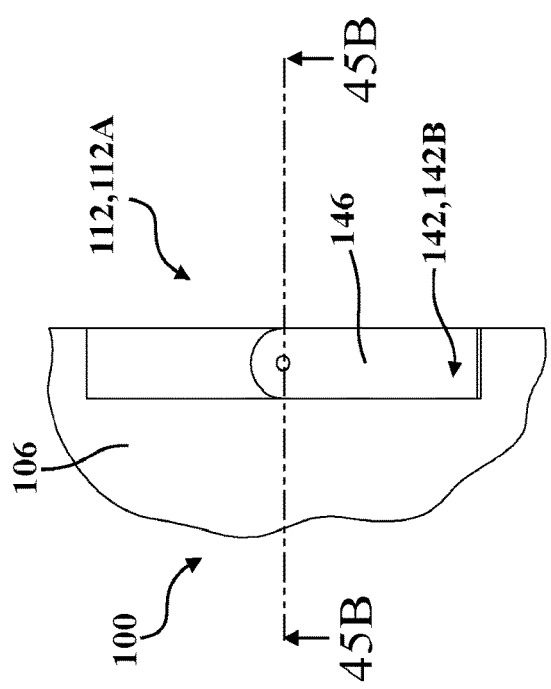
FIG. 44B is another partial top-side view of the sterilizable enclosure of FIG. 44A, shown with the lock mechanism in a locked configuration.
Figure 45B:
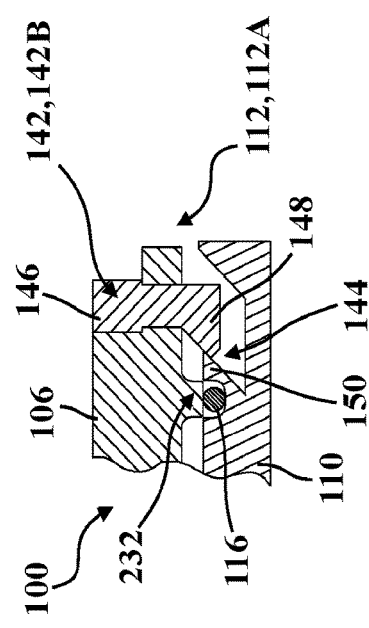
FIG. 45B is a partial section view taken along line 45B-45B in FIG. 44B.

In the representative embodiment illustrated throughout the drawings, rotation of the first lock element 142 from the first position 142A to the second position 142B causes corresponding movement of the lock mechanism 112 between a locked configuration 112A (see FIGS. 17A and 18A; see also FIGS. 44A and 45A) and an unlocked configuration 112B (see FIGS. 17B and 18B; see also FIGS. 44B and 45B). In the locked configuration 112A, the cam 148 engages the catch 150 such that the base 110 and the frame 106 are maintained in abutment locked in the closed position 100A of the sterilizable enclosure 100. In the unlocked configuration 112B, the cam 148 is disengaged from the catch 150 such that the base 110 and the frame 106 can be moved out of abutment to an opened position 100B of the sterilizable enclosure 100.

As is depicted in FIGS. 44C and 45C, the lock mechanism 112 may also have an autoclave configuration 112C, where rotation of the first lock element 142 to a third position 142C urges the base 110 and the frame 106 out of abutment with each other. Here, when in the autoclave configuration 112C with the first lock element 142 in the third position 142C, the cam 148 ensures that the sterilizable enclosure 100 remains in the opened position 100B until the first lock element 142 is subsequently rotated out of the third position 142C. As will be appreciated from the subsequent description below, this configuration could advantageously be utilized during an autoclave sterilization process, where the sterilizable enclosure 100 is placed in a pressurized chamber and is subjected to relatively-high temperature saturated steam which, during the sterilization process, could create a pressure differential across the sterilizable enclosure 100 significant enough to damage the glass panel 114, depending on the specific configuration, arrangement, sealed state, and geometry of the various components of the sterilizable enclosure 100. Nevertheless, the sterilizable enclosure 100 could omit a discrete autoclave configuration 112C.

In one embodiment, the sterilizable enclosure 100 could include a valve 158 (shown schematically in phantom in FIG. 2) operatively attached to the base 110 and/or the frame 106 for equalizing pressure of the sterilizable enclosure 100 locked in the closed position 100A under predetermined environmental conditions. It will be appreciated that the valve 158 could remain closed during conventional operation of the secured portable electronic device 102 and could be configured to open or otherwise equalize pressure with the environment in response to reaching a predetermined pressure differential threshold, such as during an autoclave sterilization cycle as described above. Moreover, it will be appreciated that the valve 158 could open automatically, or could be manually-actuated, such as with a button (not shown, but generally known in the art). Further, the valve 158 could be configured to operate in different ways depending on whether or not the portable electronic device 102 is installed or otherwise secured in the sterilizable enclosure 100.

Figure 8:
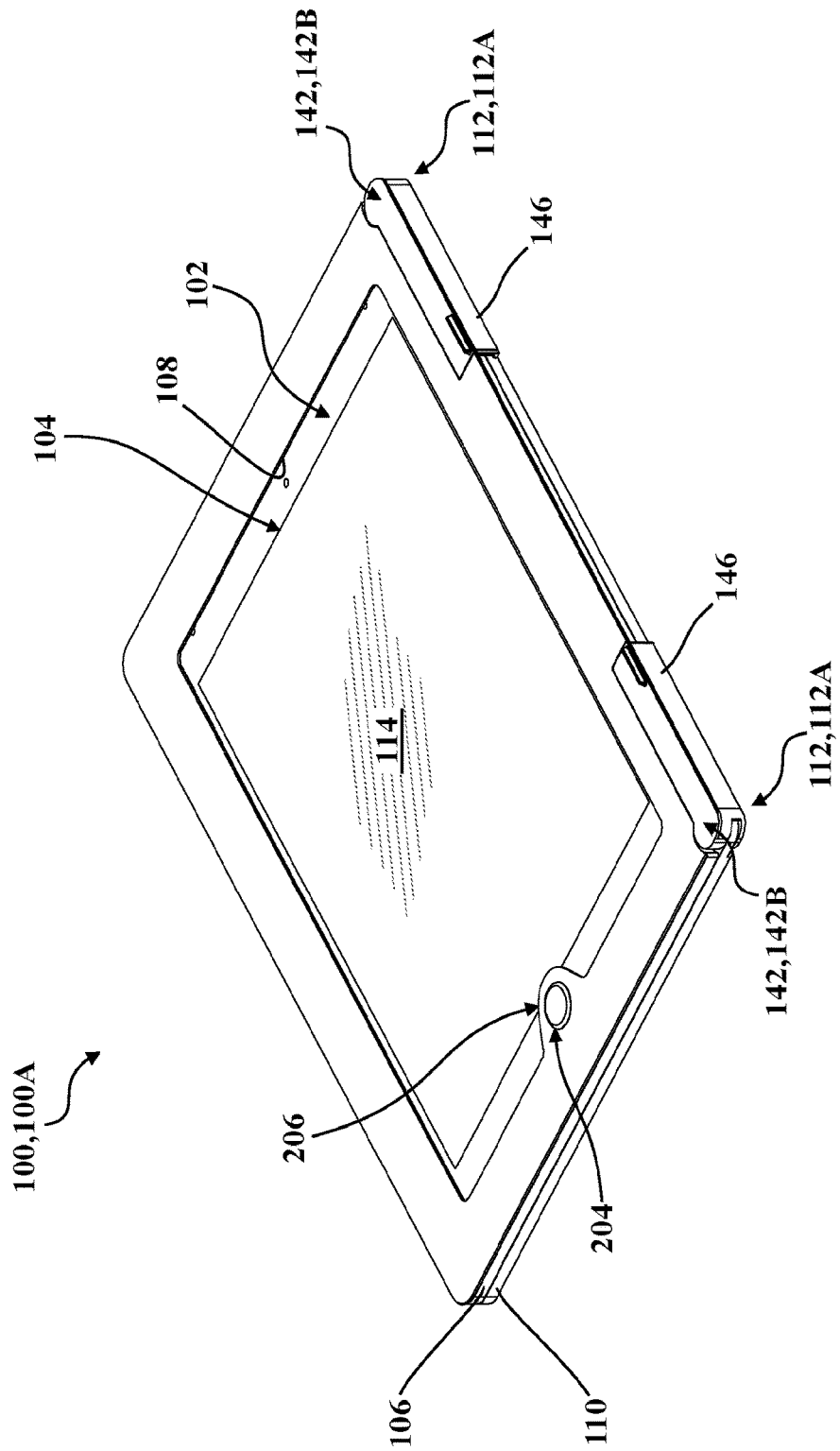
FIG. 8 is a top-side perspective view of the portable electronic device and sterilizable enclosure of FIG. 7, shown in the closed position with the lock mechanism in the locked configuration.
Figure 38:
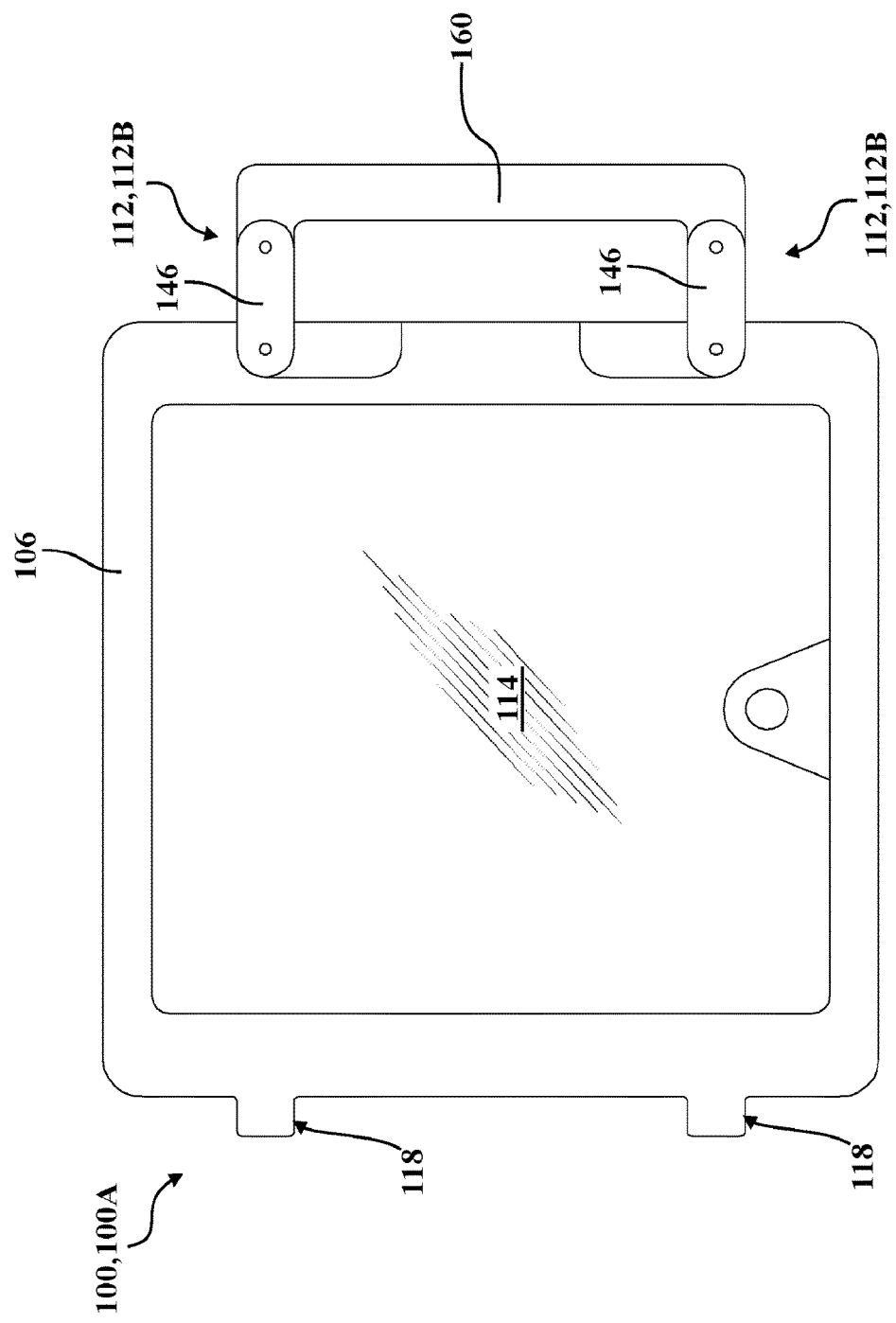
FIG. 38 is a top-side plan view of another embodiment of the sterilizable enclosure, shown with a link for actuating a lock mechanism.
Figure 39:
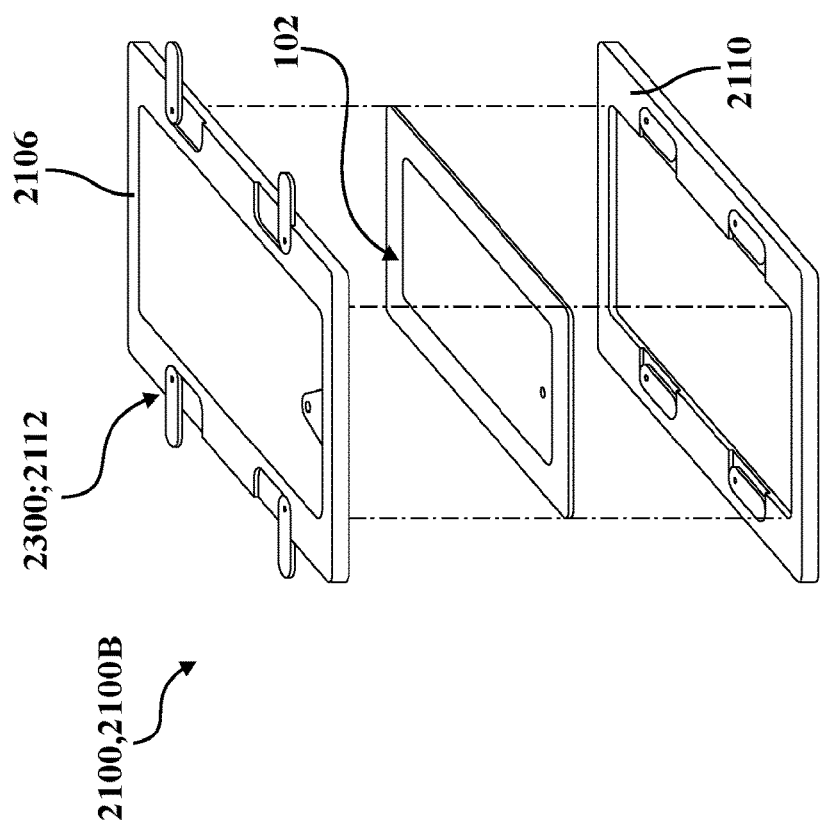
FIG. 39 is a partially exploded perspective view of another embodiment of the sterilizable enclosure, shown in an opened position with a portable electronic device spaced between a base and a frame.
Figure 40:
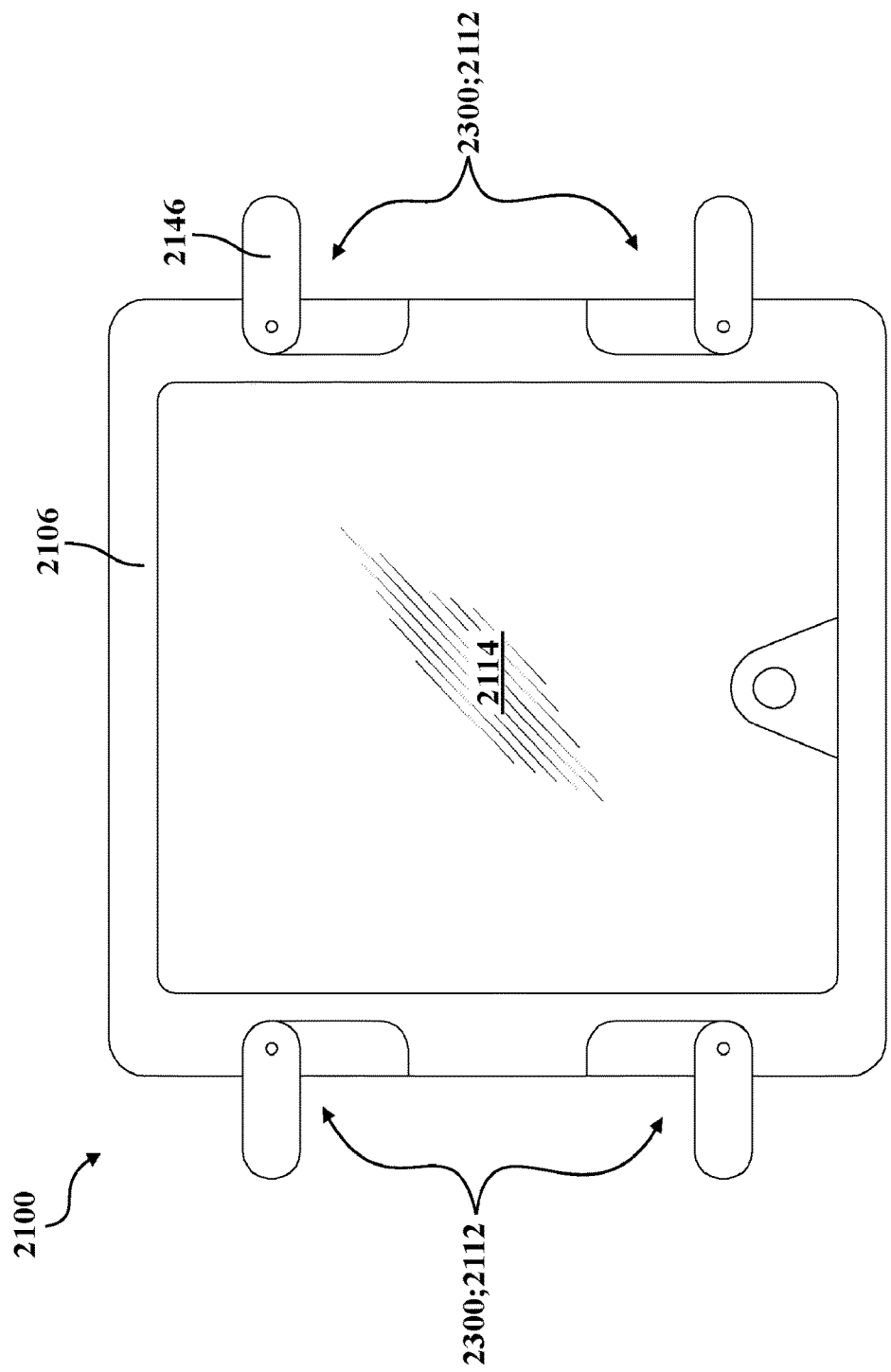
FIG. 40 is a top-side plan view of the frame of the sterilizable enclosure of FIG. 39, showing a lock mechanism in an unlocked configuration.

In the embodiment of the sterilizable enclosure 100 depicted in FIGS. 1-20C, the first lock elements 142 are mirrored such that the latches 146 are generally parallel with each other when in the first position 142A (see FIG. 7), and generally face towards each other when in the second position 142B (see FIG. 8). However, it will be appreciated that other configurations could be implemented, such as where the first lock elements 142 are also generally parallel when in the second position 142B, as depicted by the embodiment illustrated in FIG. 38. In this embodiment, the sterilizable enclosure 110 further comprises a link, generally indicated at 160, which is operatively attached to both of the first lock elements 142 for concurrent movement therewith to selectively move both of the first lock elements 142 simultaneously.

As noted above, the base 110 and the frame 106 cooperate to secure the portable electronic device 102 therebetween when the sterilizable enclosure 100 is locked in the closed position 100A to engage the seal 116 and to effect the capacitive coupling between the glass panel 114 and the touchscreen interface 104 of the portable electronic device 102. In order to promote the capacitive coupling, in one embodiment, the sterilizable enclosure 100 further comprises a bias mechanism, generally indicated at 162, operatively attached to the base 110 and/or the frame 106 (see FIGS. 4, 9, and 16). The bias mechanism 162 urges the touchscreen interface 104 of the portable electronic device 102 into abutment with the glass panel 114 with a predetermined force to enable the capacitive coupling between the glass panel 114 and the touchscreen interface 104 of the secured portable electronic device 102 when the sterilizable enclosure 100 is locked in the closed position 100A.

Figure 4:
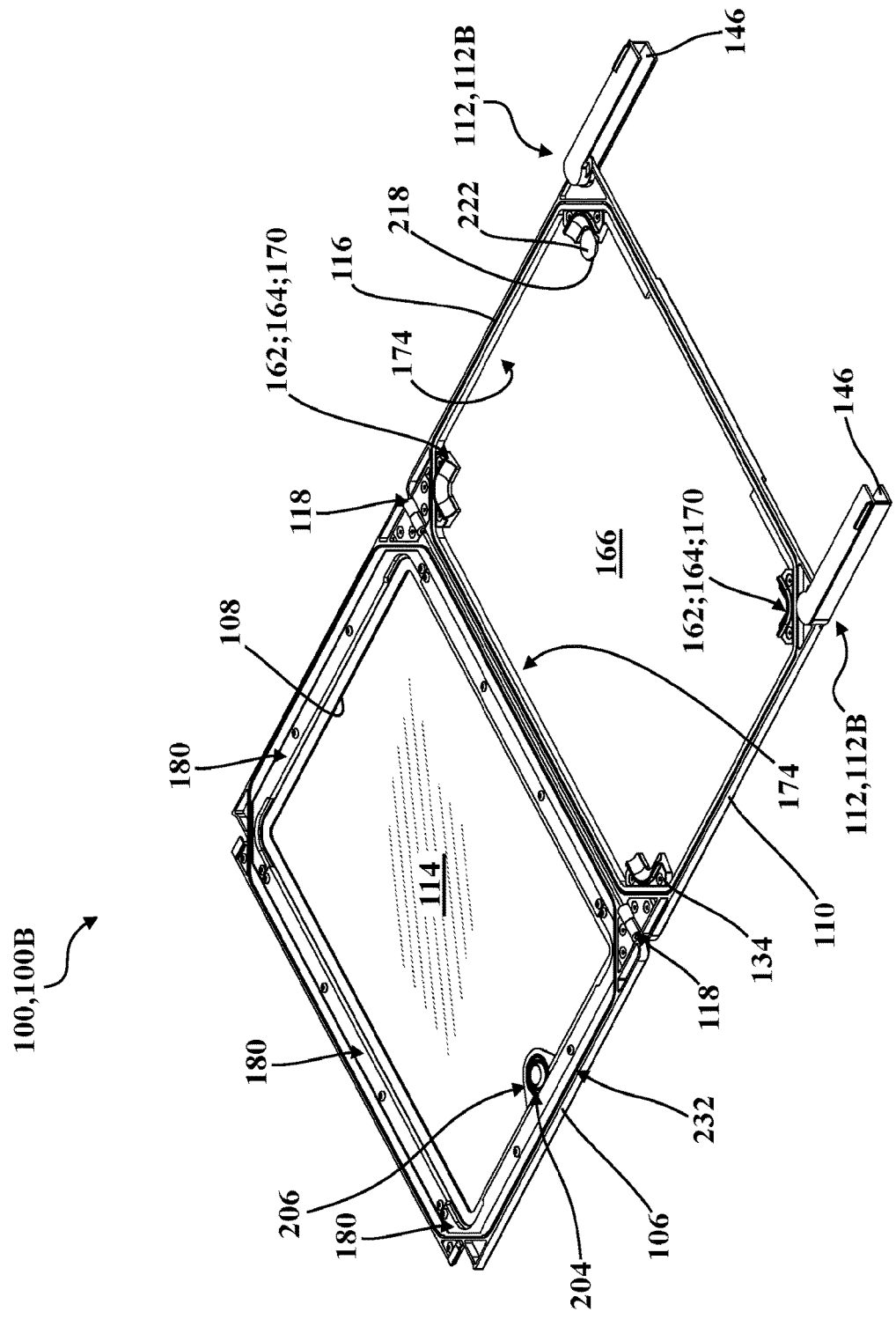
FIG. 4 is a top-side perspective view of the sterilizable enclosure of FIGS. 1-3, shown in a fully opened position.
Figure 9:
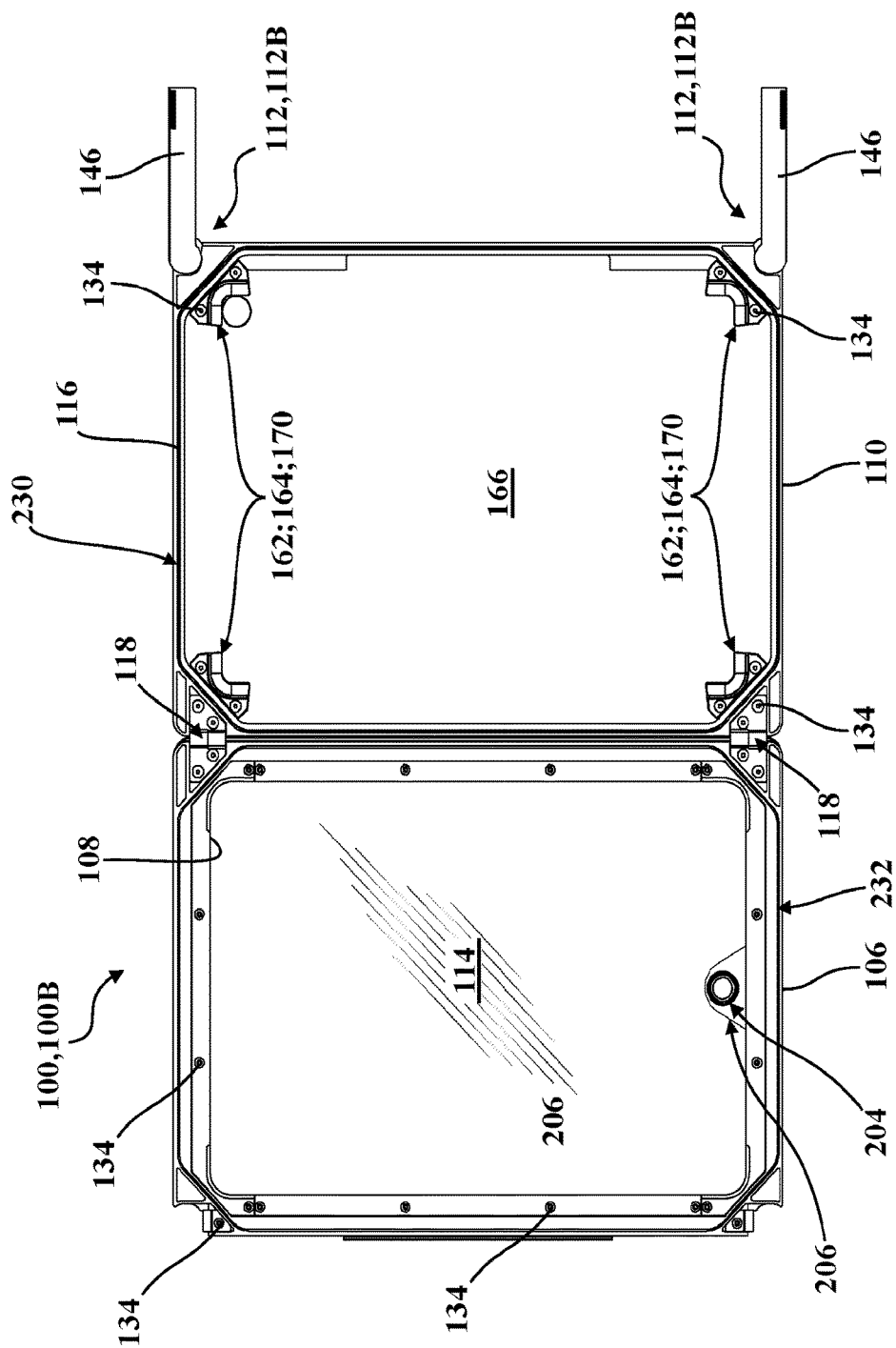
FIG. 9 is a top-side plan view of the sterilizable enclosure of FIG. 4, shown in the opened position with the lock mechanism in the unlocked configuration.
Figure 10:
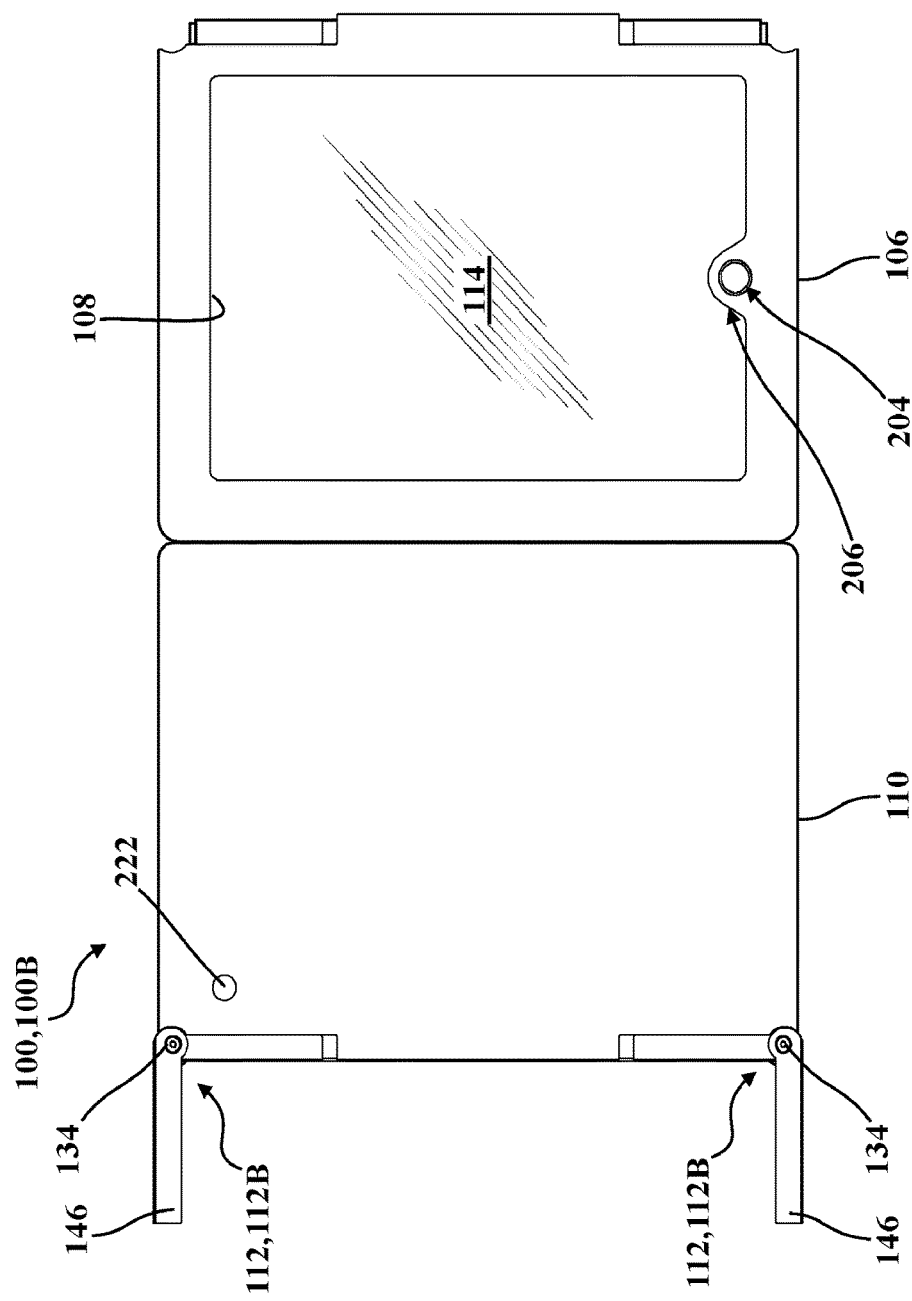
FIG. 10 is a bottom-side plan view of the sterilizable enclosure of FIG. 9, shown in the opened position with the lock mechanism in the unlocked configuration.
Figure 11:
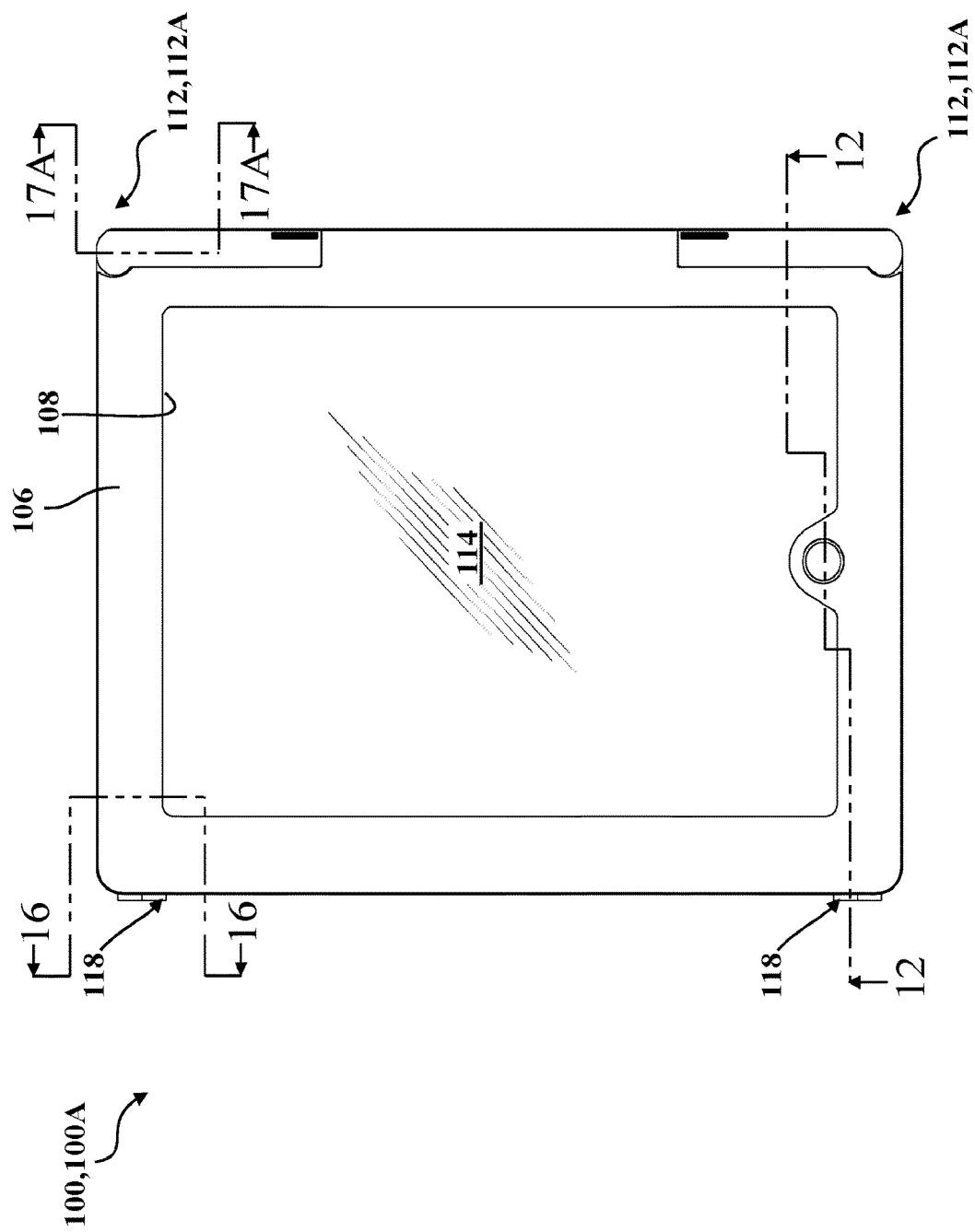
FIG. 11 is a top-side plan view of the sterilizable enclosure of FIG. 1, shown in the closed position with the lock mechanism in the locked configuration.
Figure 12:
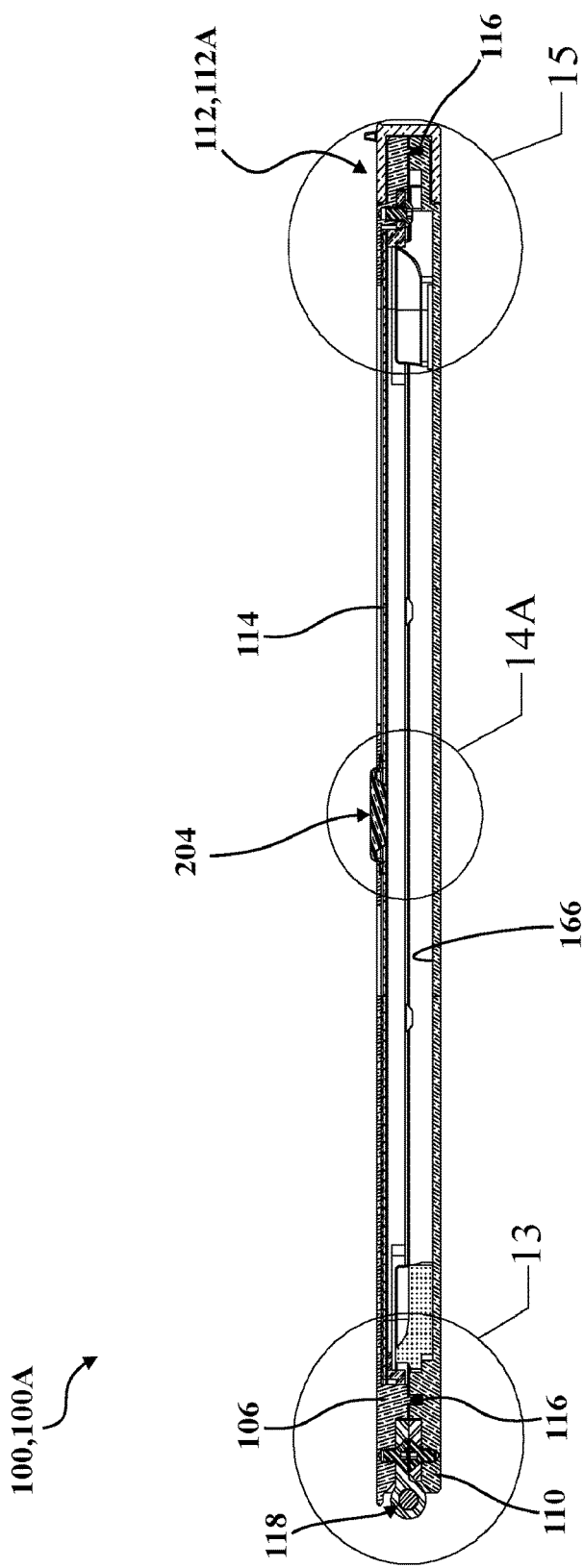
FIG. 12 is an offset sectional view taken along line 12-12 of FIG. 11.
Figure 13:
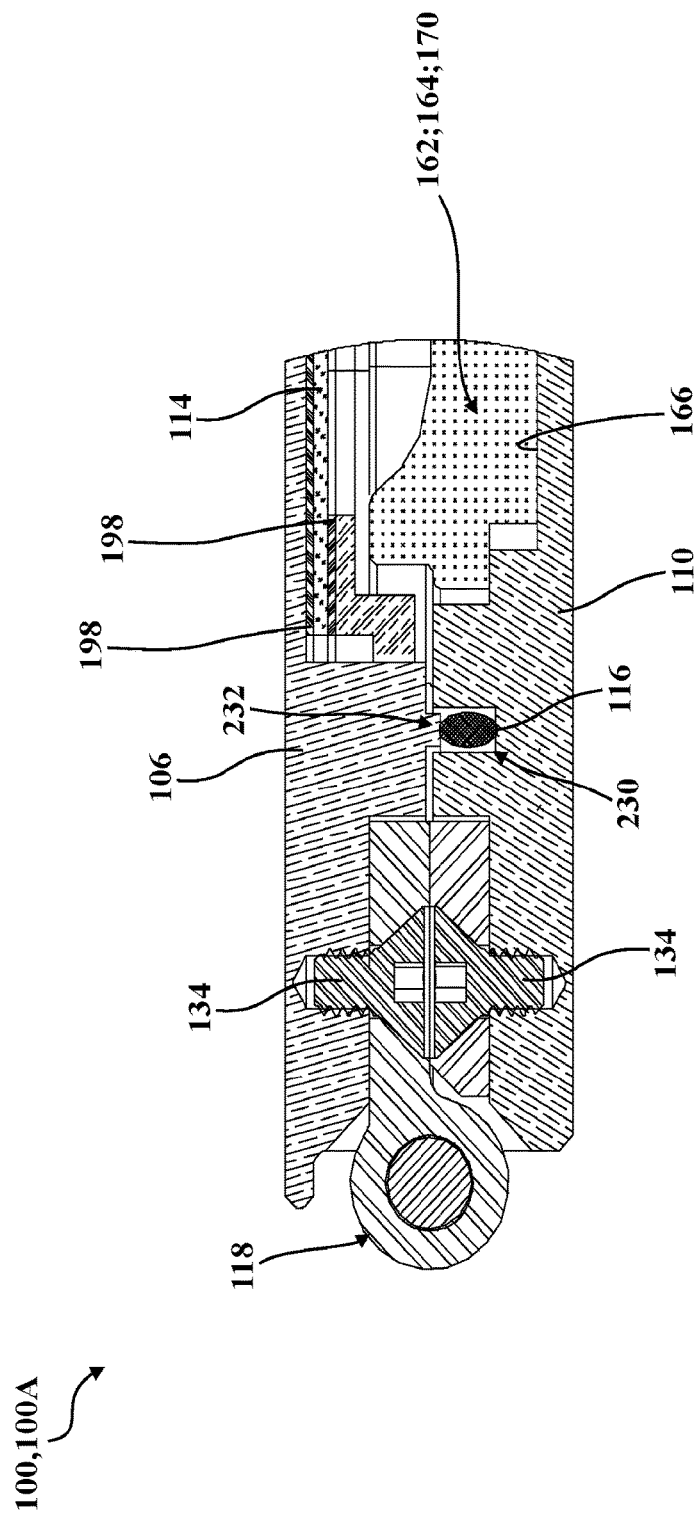
FIG. 13 is an enlarged partial sectional view of the sterilizable enclosure taken from indicia 13 of FIG. 12.
Figure 15:
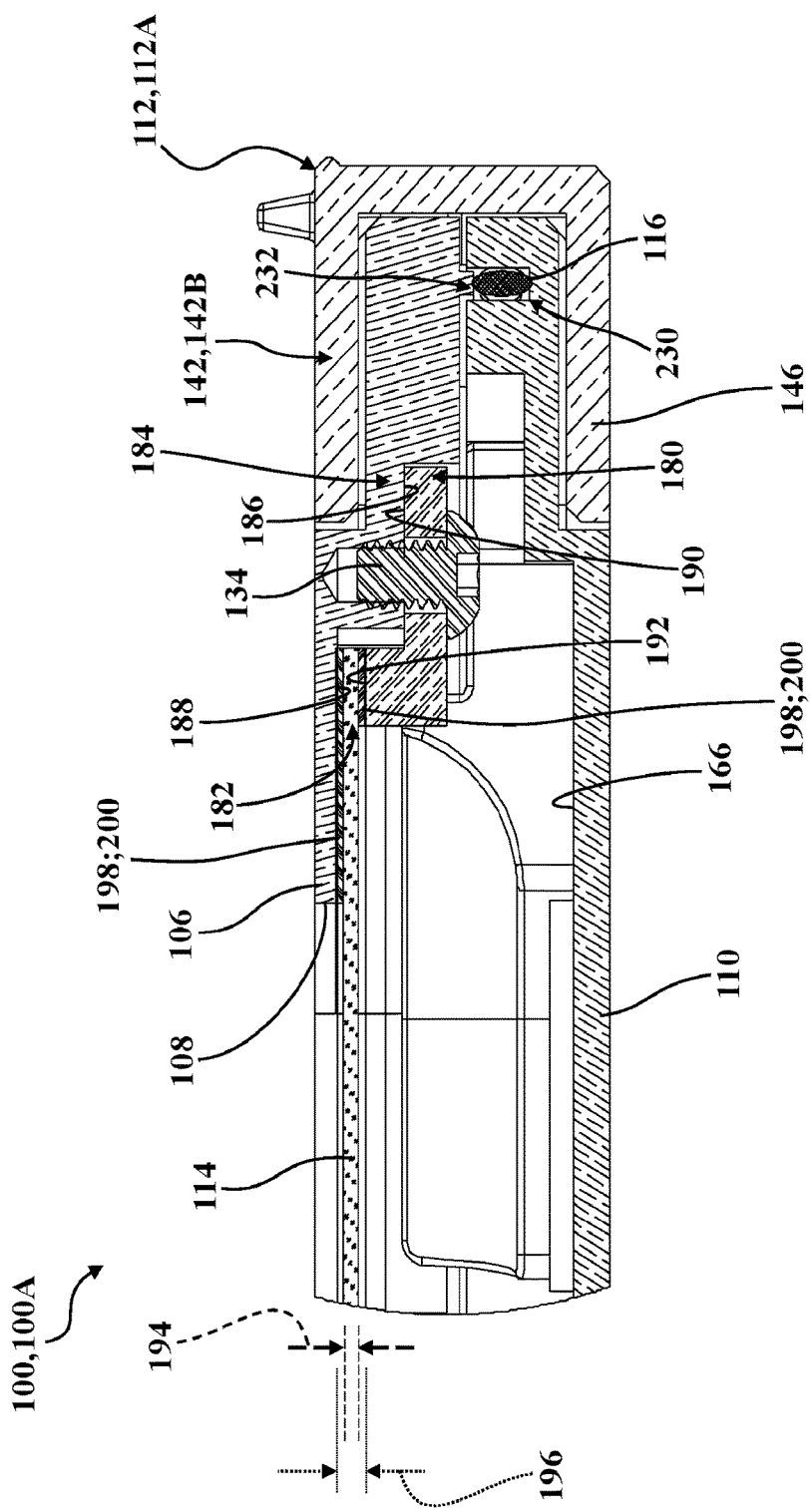
FIG. 15 is an enlarged partial sectional view of the sterilizable enclosure taken from indicia 15 of FIG. 12.
Figure 16:
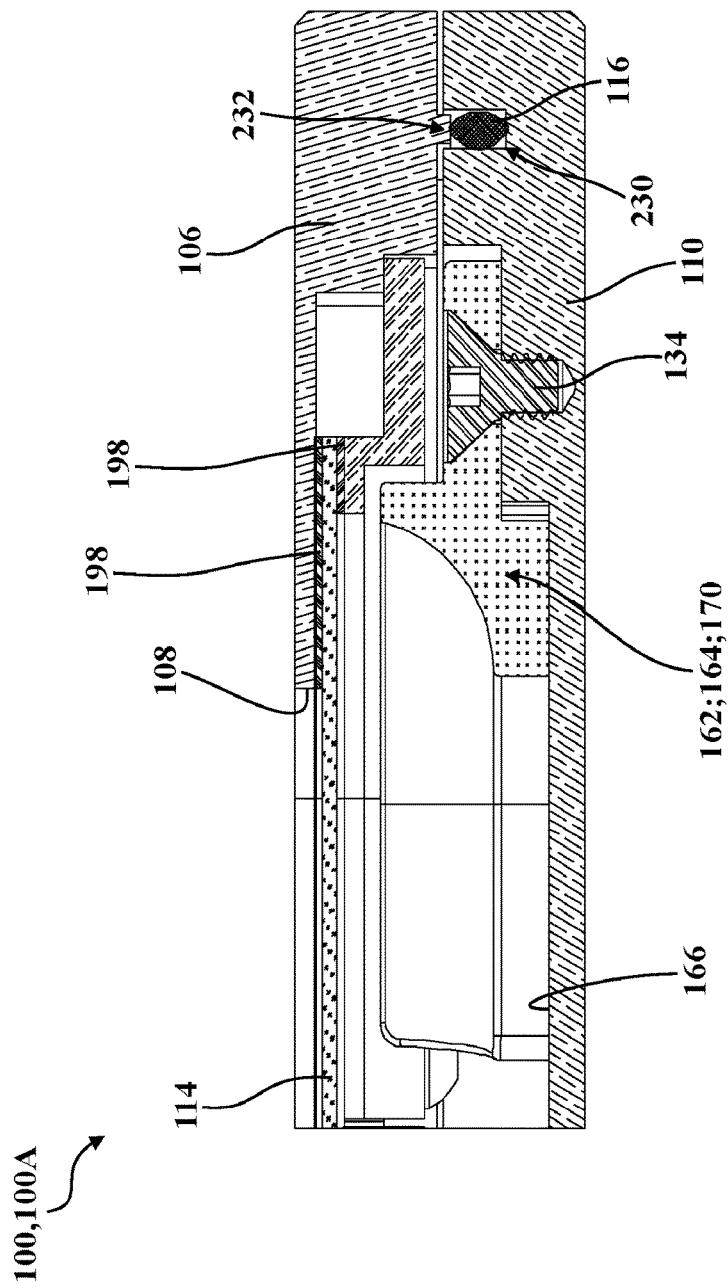
FIG. 16 is an offset sectional view taken along line 16-16 of FIG. 11.

In the representative embodiment illustrated in FIGS. 1-20C, the bias mechanism 162 is realized as four bias elements 164, each of which are operatively attached to a support surface 166 of the base 110 via fasteners 134 (see FIGS. 4, 9, and 16). The bias elements 164 are shaped and arranged to support the portable electronic device 102 and to urge the portable electronic device 102 towards the glass panel 114. The bias elements 164 are positioned at respective corners of the portable electronic device 102 and, in one embodiment, the bias elements 164 are shaped and arranged so as to align the portable electronic device 102 with respect to the glass panel 114. The specific shape and configuration of the support surface 166 and the bias elements 164 can be adjusted to effect proper alignment with one or more correspondingly-shaped portable electronic devices 102.

It will be appreciated that the bias mechanism 162 could comprise any suitable number of bias elements 164. By way of non-limiting example, a single bias element 164 could be provided. In one embodiment, the bias mechanism 162 comprises a resilient material, such as foam or rubber.

Figure 37:
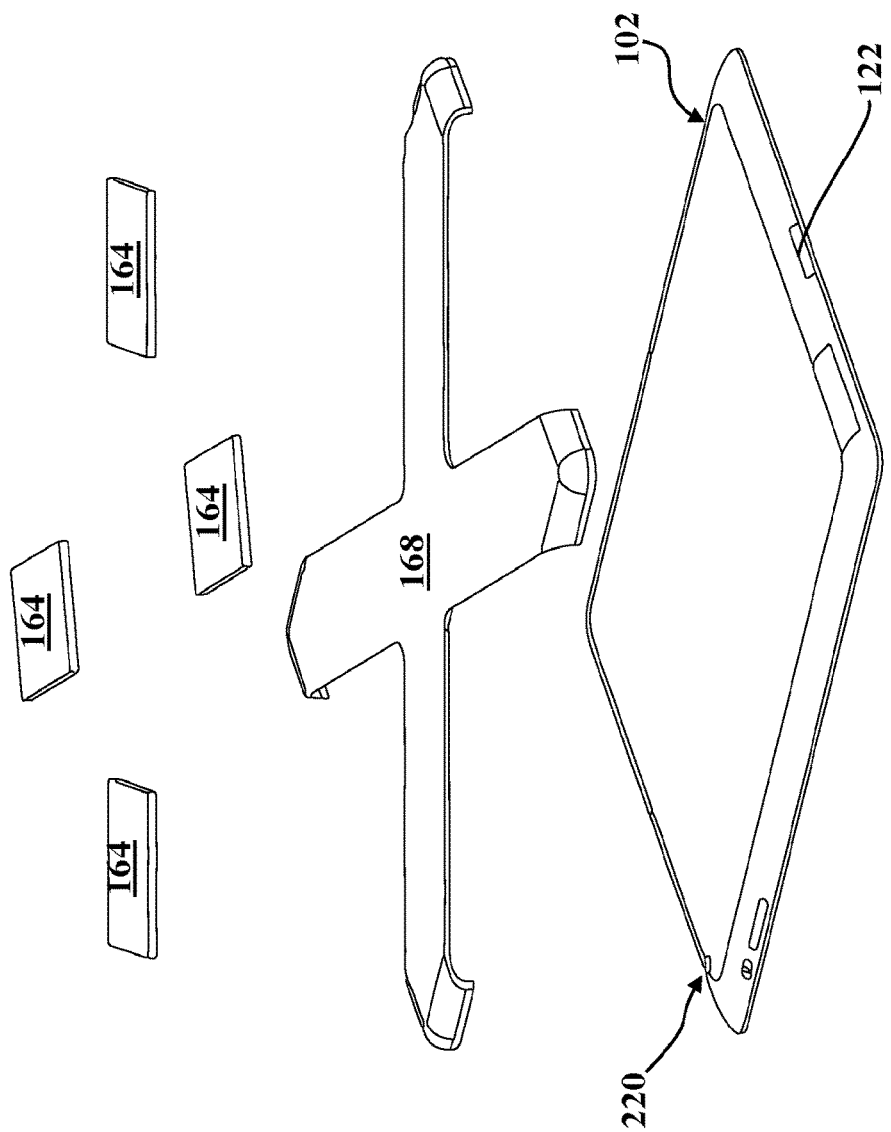
FIG. 37 is an exploded perspective view showing an alternate portable electronic device shown spaced from an intermediate device adaptor and bias elements of a bias mechanism for use with sterilizable enclosures according to one embodiment.

However, those having ordinary skill in the art will appreciate that the bias mechanism 162 could be realized in a number of different ways and could be manufactured from a number of different components and/or materials. By way of non-limiting example, the bias elements 164 could be implemented as one or more replaceable foam pads secured directly to the base 110, a spring, or another actuator configured to urge the portable electronic device 102 towards the glass panel 114. Similarly, as shown in FIG. 37, one or more bias elements 164 could be operatively attached to an intermediate device adaptor 168 which, in turn, could be configured to cooperate with the base 110 so as to receive and align different types or models of portable electronic devices 102 within the sterilizable enclosure 100 while, at the same time, urging the glass panel 114 into abutment with the touchscreen interface 104 when the sterilizable enclosure 100 is locked in the closed position 100A.

In some embodiments, the touchscreen interface 104 may be spaced from the glass panel 114, but spaced less than a predetermined distance from the glass panel 114 so that the capacitive coupling is effected so as to ensure that the touchscreen interface 104 is operable through deflection of the glass panel 114.

As noted above, in the representative embodiment of the bias mechanism 162 depicted in FIGS. 1-20C, the four bias elements 164 arranged at the respective corners of the portable electronic device 102 help align the portable electronic device 102 with respect to the glass panel 114. Further to this end, in one embodiment, at least one of the base 110 and the frame 106 includes a tray, generally indicated at 170, for aligning the portable electronic device 102 with respect to the sterilizable enclosure 100. The alignment afforded by the tray 170 ensures proper orientation of the portable electronic device 102 with the glass panel 114 without necessitating excessive position manipulation during installation into the sterilizable enclosure 100, thereby contributing to ease in conforming to sterile protocol by requiring less handling of the sterilizable enclosure 100 and/or the portable electronic device 102. In the embodiment of the sterilizable enclosure 100 depicted in FIGS. 1-20C, the tray 170 is realized by the four bias elements 164 of the bias mechanism 162.

It will be appreciated that the alignment afforded by the tray 170 could be provided independent of the biasing afforded by the bias mechanism 162 in certain embodiments. By way of example, the embodiment of the sterilizable enclosure 100 depicted in FIGS. 26 and 27 comprises a tray 170 which is formed integrally with the base 110. Here, biasing is afforded independently of the tray 170, such as by one or more bias elements 164 operatively attached to the intermediate device adaptor 168 (see FIG. 37) or attached to the base 110 (not shown). Moreover, in this embodiment, the tray 170 is realized by the support surface 166 of the base 110 and by four corner braces 172 which extend from the support surface 166. It will be appreciated that the specific shape and configuration of the support surface 166 and corner braces 172 can be adjusted to effect proper alignment with one or more correspondingly-shaped portable electronic devices 102.

In one embodiment, the sterilizable enclosure 100 further comprises at least one relief, generally indicated at 174, arranged to help facilitate proper removal of the portable electronic device 102 from the sterilizable enclosure 100 while in the opened position 100B, which contributes to further minimization of handling of the unsecured portable electronic device 102. It will be appreciated that the relief 174 can be defined in a number of different ways depending on the specific configuration of the sterilizable enclosure 100, such as by an area adjacent to the support surface 166 extending between pairs of bias elements 164 (see FIG. 4) or pairs of corner braces 172 (see FIG. 27). The relief 174 may be sized so as to correspond to the dimensions of the user's finger.

As shown in FIG. 19, the sterilizable enclosure 100 may include at least one magnet, generally indicated at 176, for cooperating with a corresponding magnet or ferrous object of the portable electronic device, such as a so-called iPad® "smart cover" magnet (not shown, but generally known in the related art) to further promote alignment of the portable electronic device 102 with respect to the sterilizable enclosure 100 during installation. While a pair of magnets 176 are depicted in FIG. 19 as being coupled to support surface 166 of the base 110, such as by fasteners (not shown), one or more magnets 176 could be operatively attached to any suitable part of the sterilizable enclosure 100, or could be omitted entirely. Further, it will be appreciated that the base 110 and/or the frame 106 could include additional magnets and/or a ferrous plate 178 (shown schematically in FIG. 19) for attaching the sterilizable enclosure 100 to an external magnetic support stand or mount (not shown). While the magnet 176 and the ferrous plate 178 are specifically depicted in the embodiment illustrated in FIG. 19, those having ordinary skill in the art will appreciate that other embodiments described and illustrated herein could similarly incorporate magnets 176 and/or ferrous plates 178.

As noted above, the glass panel 114 of the sterilizable enclosure 100 is configured to abut the touchscreen interface 104 of the portable electronic device 102 when locked in the closed position 100A. In one embodiment, the glass panel 114 is manufactured from a chemically-strengthened aluminosilicate material, such as Corning® Gorilla® glass, which affords increased durability compared to conventional soda-lime glass. The glass panel 114 could comprise any suitable type of glass. In other embodiments, the glass panel 114 or another type of transparent panel could be formed of other materials capable of withstanding repeated steam sterilization in an autoclave, in which the transparent panel is subjected to a temperature of 134 degrees Celsius for 3 minutes or to a temperature of 121 degrees Celsius for 15 minutes. These materials have also been distinctively chosen due to their resistance to commonly used disinfectants.

In the representative embodiments illustrated throughout the drawings, the glass panel 114 is removably secured to the frame 106, as noted above. However, the glass panel 114 could be selectively secured to the base 110 via the lock mechanism 112 and without a discrete frame 106, or could be attached to the frame 106 such as with an adhesive.

Referring now to FIGS. 4 and 15, in one embodiment, the sterilizable enclosure 100 further includes a retainer, generally indicated at 180, removably attached to the frame 106 and cooperating with the frame 106 to define a gap 182 for removably securing the glass panel 114 therein. As shown best in FIG. 15, the frame 106 has a stepped ledge 184 disposed adjacent to the window 108 which defines an upper shelf 186 and a lower shelf 188 at least partially supporting the glass panel 114. Here, the lower shelf 188 extends into the window 108 and is shaped complimentarily to the portable electronic device 102 such that the lower shelf 188 of the frame 106 supports the glass panel 114 adjacent to the periphery of the portable electronic device 102 without obscuring the touchscreen interface 104 when in the closed position 100A. It will be appreciated that this arrangement helps effect the capacitive coupling via the bias mechanism 162 while, at the same time, promoting loading of the glass panel 114 between the lower shelf 118 of the frame 106 and the portable electronic device 102 along the outer periphery of the portable electronic device 102, optionally aligned with a frame member of the portable electronic device. This arrangement helps distribute force more evenly across the glass panel 114 without bending or bowing the center of the glass panel 114 or the center of the touchscreen interface 104, which could otherwise create gaps between the glass panel 114 and the touchscreen interface 104, the presence of which may be detrimental to the sensitivity and operation of the touchscreen interface 104 in use.

allow the glass panel 114 to properly contact and engage the touchscreen interface 104 to effect the capacitive coupling, as noted above.

With continued reference to FIGS. 4 and 15, the retainer 180 is removably secured to the upper shelf 186 of the stepped ledge 184 of the frame 106 using fasteners 134. As best shown in FIG. 15, the retainer 180 defines an interface surface 190 for abutting the upper shelf 186 of the frame 106, and a compression surface 192 for at least partially supporting the glass panel 114. It will be appreciated that the sterilizable enclosure 100 could employ any suitable number of retainers 180 to secure the glass panel 114. In the representative embodiment illustrated in FIG. 4, the sterilizable enclosure 100 employs four retainers 180 spaced about the window 108 of the frame 106 and secured thereto. It will be appreciated that the retainer 180 and the frame 106 cooperate to facilitate replacement or servicing of the glass panel 114. However, the glass panel 114 could be operatively attached to the frame 106 in other ways, such as with an adhesive capable of withstanding repeated steam sterilization in an autoclave, as previously discussed.

Referring now to FIG. 15, in one embodiment, the glass panel 114 has a first thickness 194, and the gap 182 defines a first distance 196 greater than the first thickness 194. In FIG. 15, the first thickness 194 and the first distance 196 are illustrated by respective phantom lines positioned adjacent to the sterilizable enclosure 100. The lower shelf 188 of the frame 106 is spaced from the compression surface 192 at the first distance 196. In one embodiment, the sterilizable enclosure 100 further includes at least one gasket 198 abutting the glass panel 114 and at least one of the lower shelf 188 and the compression surface 192. In the representative embodiment illustrated herein, two gaskets 198 are provided: one disposed between the glass panel 114 and the compression surface 192; and one disposed between the glass panel 114 and the lower shelf 188. The gasket 198 disposed between the glass panel 114 and the compression surface 192 extends from an outer edge of the glass panel 114 across the entire compression surface 192, but could only partially extend across the compression surface 192 in other embodiments. The gasket 198 disposed between the lower shelf 188 and the glass panel 114 extends from the outer edge of the glass panel 114 to an inner edge of the lower shelf 188, but could terminate short of the inner edge of the lower shelf 188 in other embodiments.

Each gasket 198 has a second thickness 200 measured prior to attaching the retainer 180 to the frame 106, and a sum of the first thickness 194 of the glass panel 114 and the second thickness 200 of the gaskets 198 is greater than the first distance 196 of the gap 182. Thus, the gaskets 198 compress against the glass panel 114 during attachment of the retainer 180. It will be appreciated that this configuration promotes even loading against the glass panel 114 and "bottoms out" the retainer 180 against the upper shelf 186 to prevent over-tightening of the retainer 180 which could otherwise shatter the glass panel 114 during assembly of the frame 106.

In some embodiments, when the portable electronic device 102 is secured in the sterilizable enclosure 100 in the closed position 100A, the lower shelf 188 of the frame 106 extends over an outer peripheral edge of the portable electronic device 102 such that the lower shelf 188 helps hold the portable electronic device 102 in the sterilizable enclosure 100.

It will be appreciated that the thickness 194 of the glass panel 114 can be adjusted to accommodate different sizes and/or types of portable electronic devices 102, depending on specific application requirements. Further, it will be appreciated that a substantial balance needs to be struck between the strength of the glass panel 114, which increases with increasing glass panel 114 thickness 194, and consistent translation of input to the touchscreen interface 104, which decreases with increasing glass panel 114 thickness 194. Moreover, it will be appreciated that the thickness 194 of the glass panel 114 can be adjusted to correspond to changes in the surface area of the touchscreen interface 104 of certain sizes and types of portable electronic devices 102. In one embodiment, the glass panel 114 has a thickness 194 of between 0.1 mm and 1.9 mm facilitates translation of input to the touchscreen interface 104 of conventional portable electronic devices 102, with a thickness 194 of between 0.75 mm and 1.25 mm being advantageous in certain applications, and a thickness 194 of between 0.33 mm and 1.5 mm being acceptable in certain applications.

Figure 5:
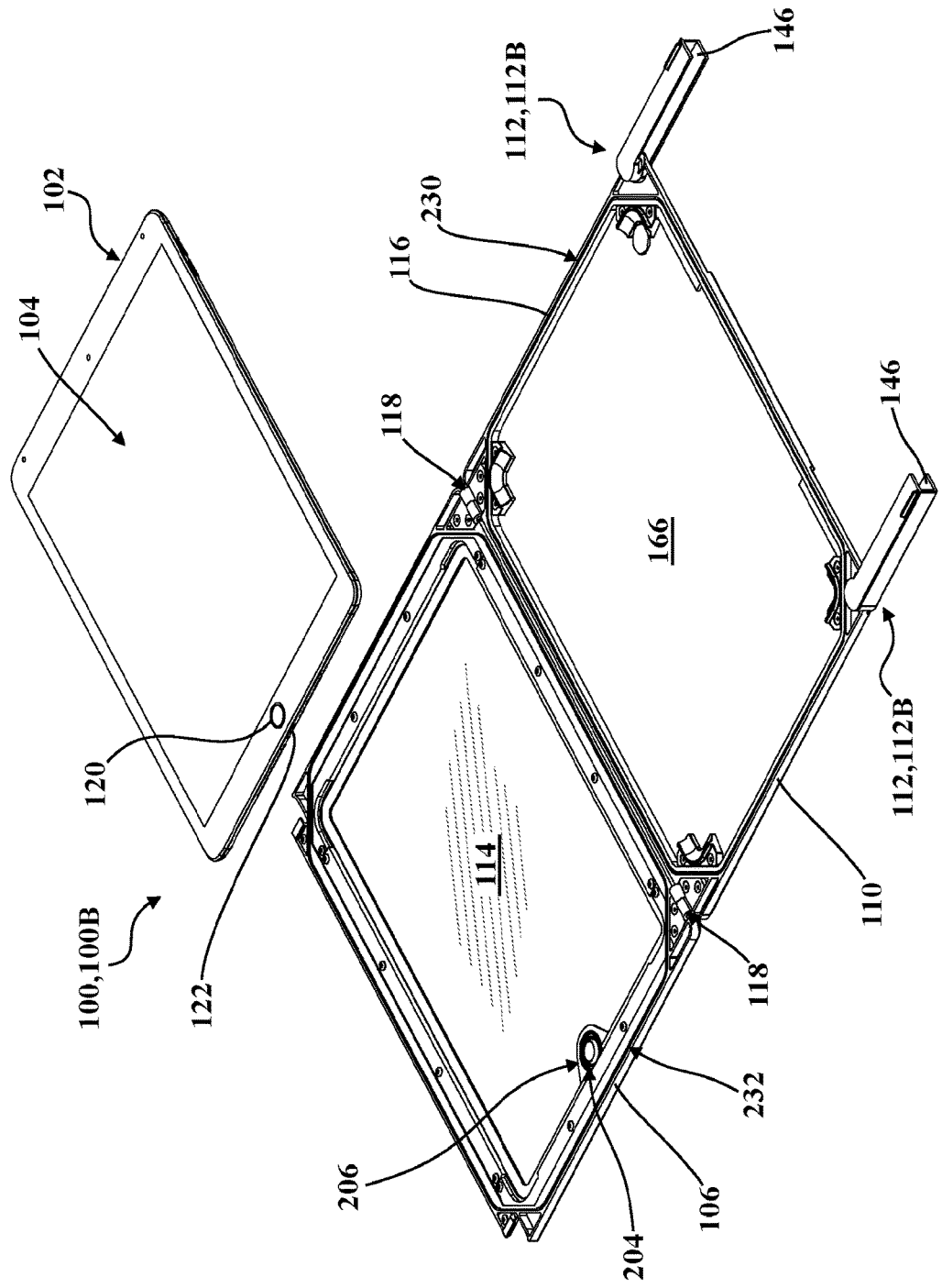
FIG. 5 is a top-side perspective view of a portable electronic device spaced from the base of the sterilizable enclosure of FIG. 4.

Referring now to FIGS. 1-5 and 14A-14C, as noted above, the portable electronic device 102 may include an input control 120 adjacent to the touchscreen interface 104 for facilitating additional selective control of the portable electronic device 102 (see FIG. 5). In one embodiment, the glass panel 114 of the sterilizable enclosure 100 includes a through-hole 202 (see FIGS. 14A-14C) defined therein disposed adjacent to the input control 120 of the portable electronic device 102 in the closed position 100A. Here, the sterilizable enclosure 100 further includes a button, generally indicated at 204, engaging the glass panel 114 adjacent to the through-hole 202 for selectively translating force to the input control 120 of the secured portable electronic device 102. More specifically, the button 204 is movable such that force applied to the button 204 is translated to the input control 120 of the secured portable electronic device 102. In certain embodiments, the button 204 could comprise a capacitive material.

Figure 14A:
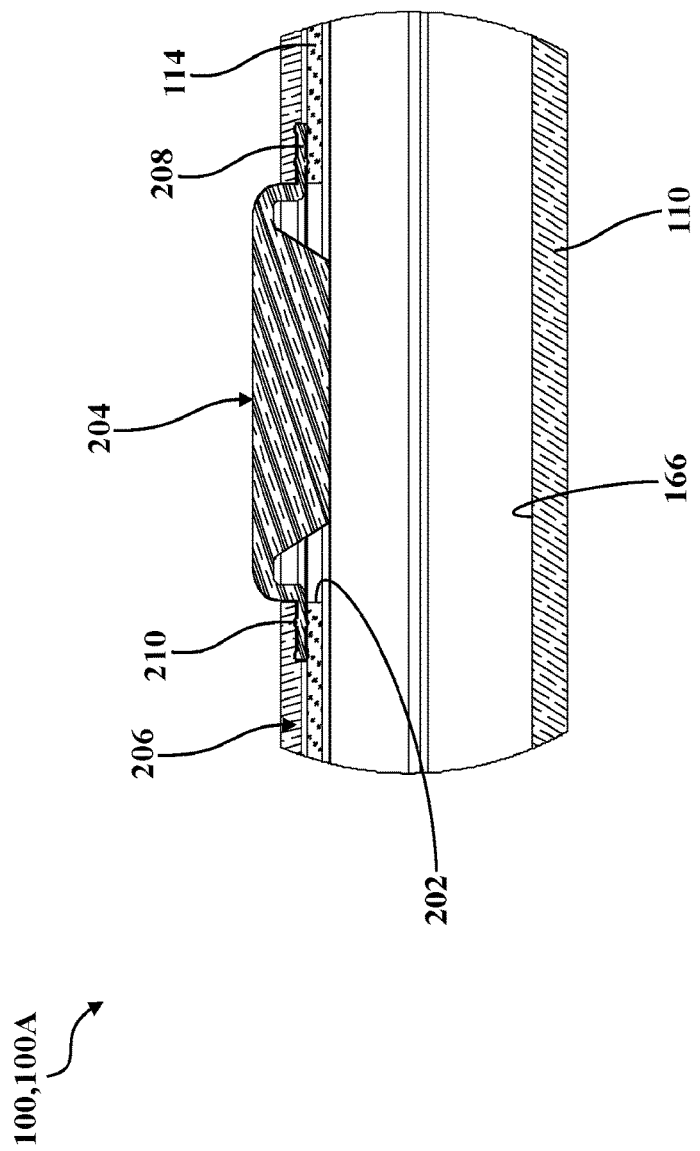
FIG. 14A is an enlarged partial sectional view of the sterilizable enclosure taken from indicia 14A of FIG. 12, showing a button arrangement according to one embodiment.
Figure 14B:
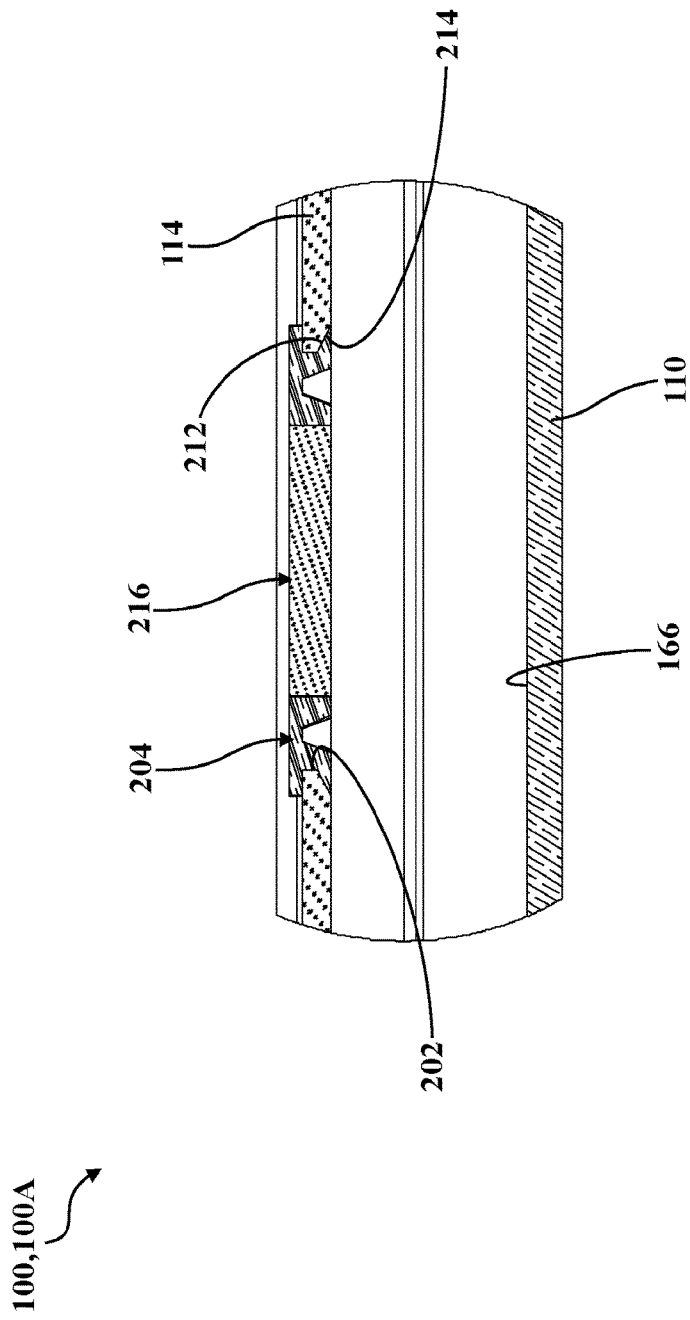
FIG. 14B is an enlarged partial sectional view of another button arrangement alternate to the button arrangement of FIG. 14A.
Figure 14C:
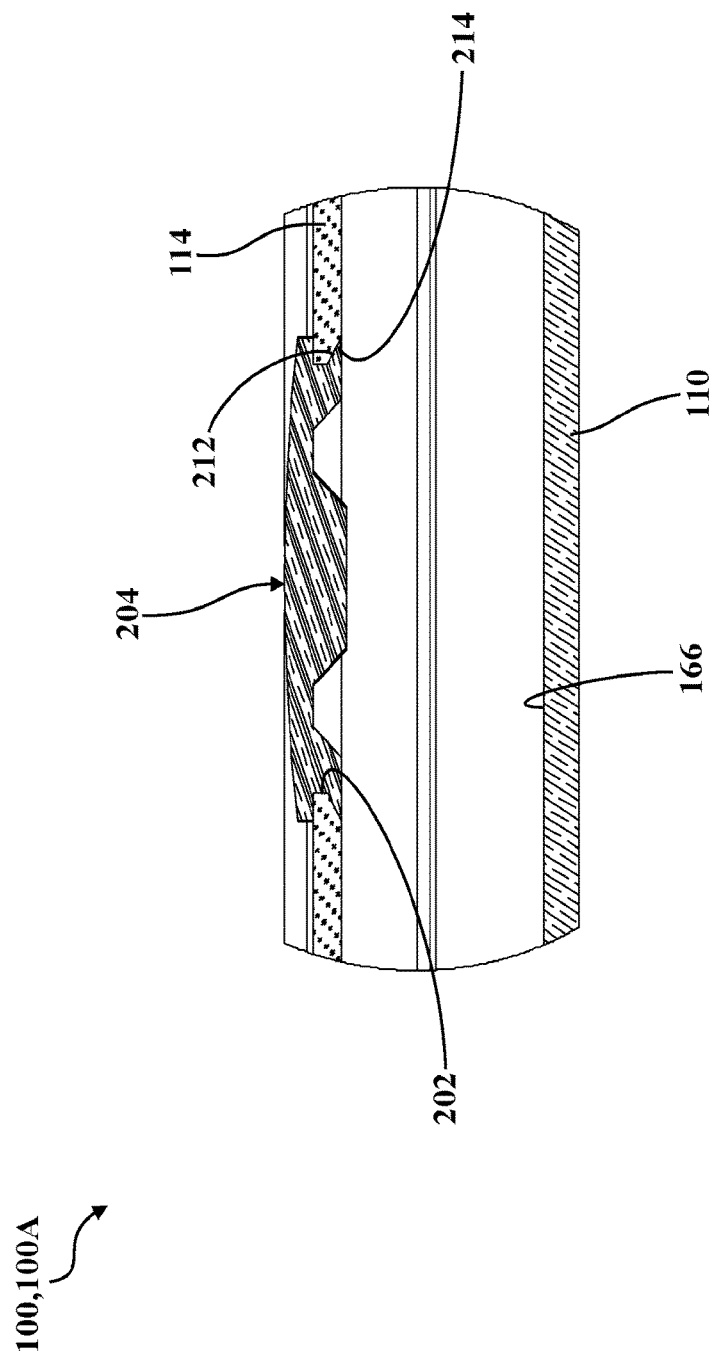
FIG. 14C is an enlarged partial sectional view of another button arrangement alternate to the button arrangements of FIGS. 14A and 14B.

In one embodiment, the frame 106 of the sterilizable enclosure 100 includes a brace, generally indicated at 206, extending into the window 108 and at least partially supporting the button 204 against the glass panel 114 adjacent to the through-hole 202 (see FIG. 1). It will be appreciated that the brace 206 may also help support the glass panel 114 in the frame 106. Moreover, it will be appreciated that the gasket 198 could be shaped complimentarily to the brace 206 (not shown in detail in this embodiment). In the embodiment of the button 204 illustrated in FIGS. 1-4, and as is shown in FIG. 14A, a button lip 208 may be provided with at least one rib 210 extending therefrom for compressing against the brace 206 and/or the glass panel 114. Here, the button lip 208 includes ribs 210 for compressing against both the brace 206 and the glass panel 114 (see FIG. 14A). In the embodiment of the button 204 illustrated in FIGS. 14B and 14C, the brace 206 is omitted from the frame 106 and the button 204 includes a flange 212 at least partially supporting the button 204 against the glass panel 114 (see FIGS. 14B and 14C). Here, the through-hole 202 of the glass panel 114 may include a tapered edge 214 complimentarily shaped to and at least partially abutting the flange 212 of the button 204. The button 204 may further include a transparent insert, such as a glass insert 216 supported therein (see FIG. 14B) adjacent to the input control 120 of the secured portable electronic device 102 when in the closed position 100A. The glass insert 216 is at least partially transparent and is configured to transmit light therethrough to one or more sensors of the portable electronic device 102 adjacent to or otherwise integrated into the input control 120, such as a so-called "fingerprint reader" or "touch identification sensor". As noted above, one or more portions of the button 204 could comprise a capacitive material.

Similarly, as shown in FIGS. 1-4, in one embodiment, one of the base 110 and the frame 106 may define an aperture 218 for being disposed adjacent to a camera 220 (see FIG. 29; not shown in detail, but generally known in the related art) on a back of the secured portable electronic device 102, with a transparent insert 222 supported in the aperture 218 for facilitating transmission of light to the camera of the secured portable electronic device 102. The insert 222 could be manufactured from any suitable material sufficient to transmit light, such as glass, sapphire, quartz, plastic, and the like. Here, the base 110 of the sterilizable enclosure 100 defines the aperture 218 supporting the insert 222, and both the aperture 218 and insert 222 each have a frustoconical profile, which helps keep the insert 222 secured to the base 110 in operation (not shown in detail). The insert 222 could be secured to the base 110 by press-fit, adhesive, fasteners, or other suitable methods. In other embodiments, the aperture could have a counterbore configuration for receiving a cylindrical insert. Other shapes, arrangements, and configurations of the aperture 218 and insert 222 are also contemplated.

Figure 41:
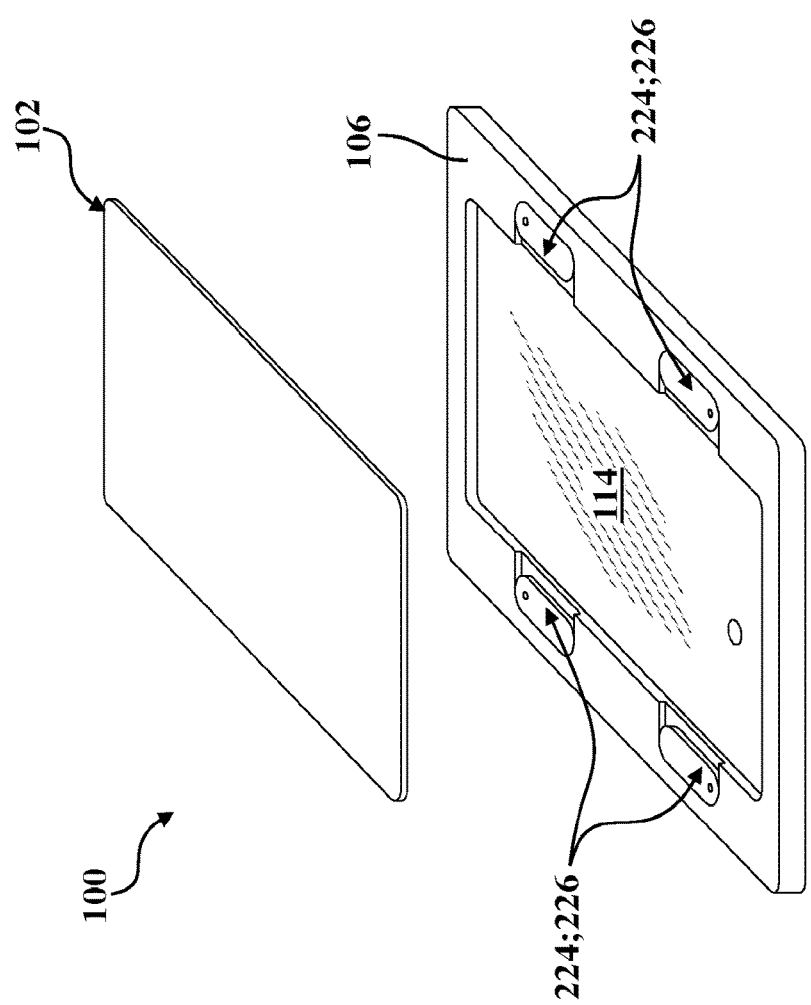
FIG. 41 is a perspective view of a portable electronic device spaced from a frame of a sterilizable enclosure having a preassembly mechanism according to one embodiment.
Figure 42:
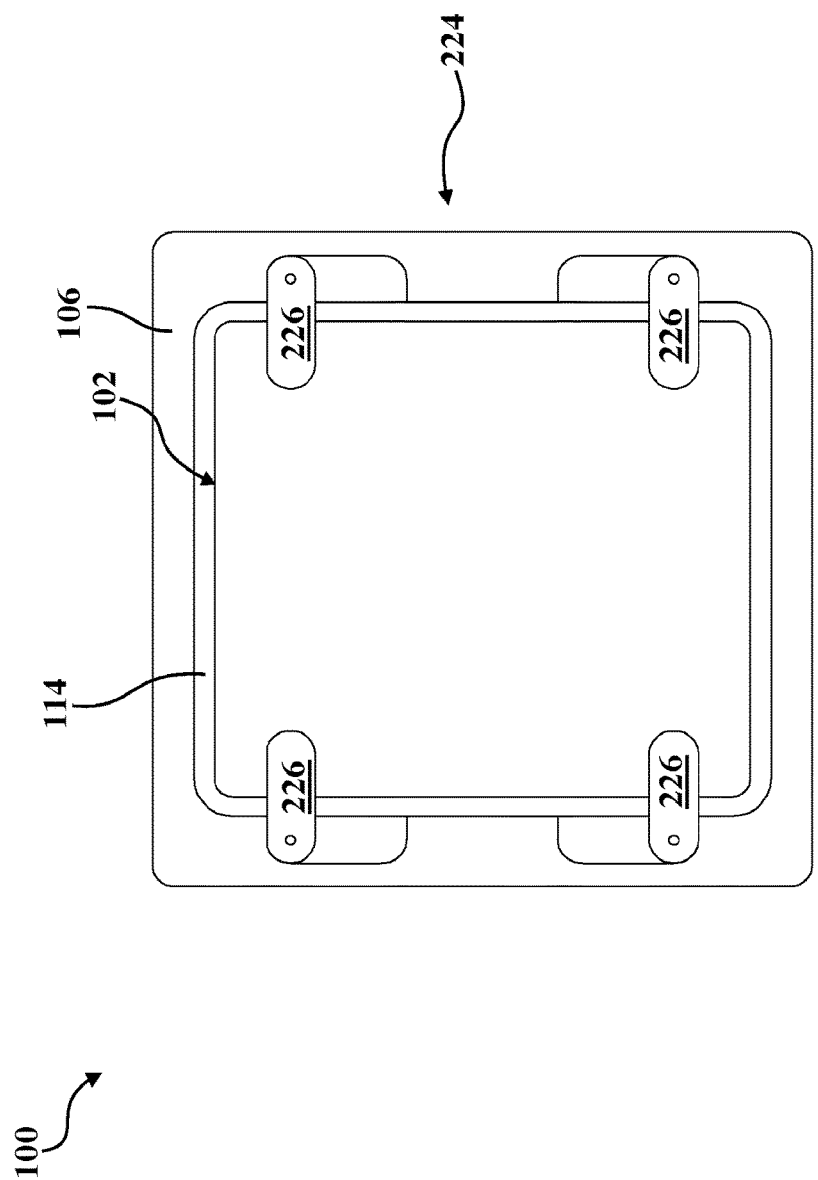
FIG. 42 is a bottom-side plan view of the portable electronic device engaged by the preassembly device of the frame of FIG. 41.
Figure 43:
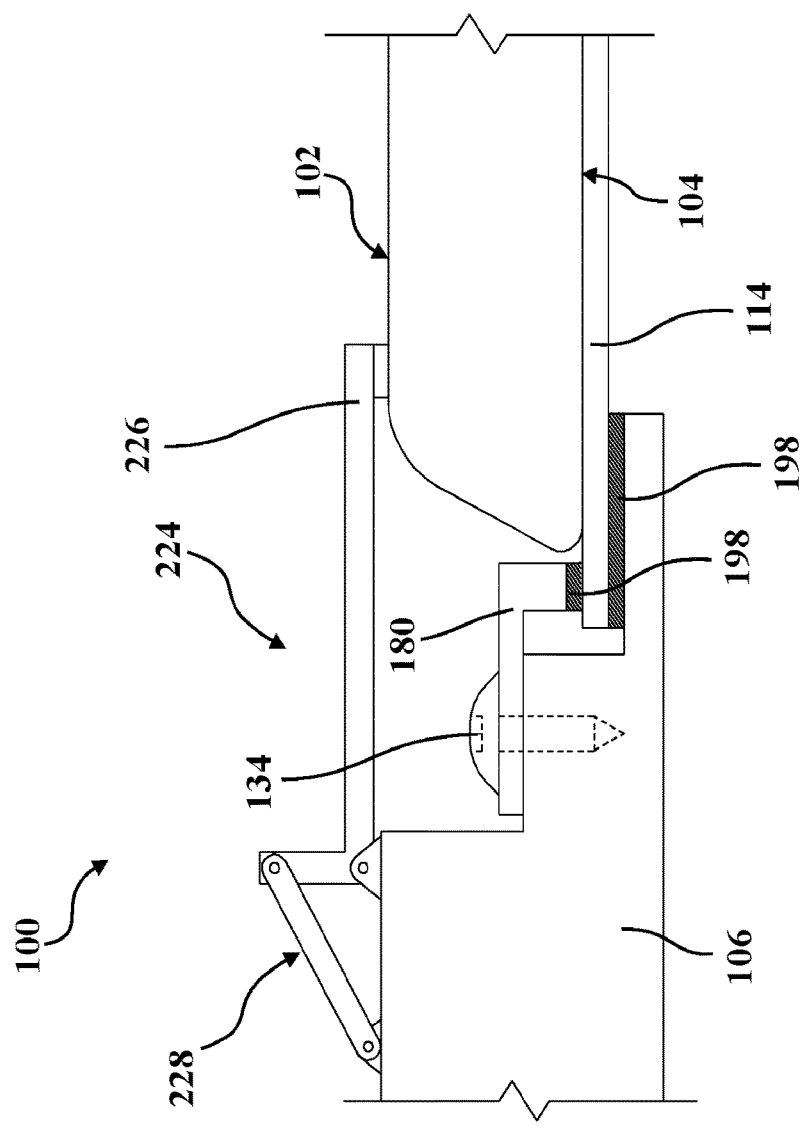
FIG. 43 is a partial sectional view of a portable electronic device engaged by a preassembly device alternate to the preassembly device of FIG. 42.

As noted above, in one embodiment, movement of the lock mechanism 112 to the locked configuration 112A urges the glass panel 114 into abutment with the touchscreen interface 104 of the portable electronic device 102 and, at the same time, locks the sterilizable enclosure 100 in the closed position 100A. However, the sterilizable enclosure 100 could urge the glass panel 114 into abutment with the touchscreen interface 104 of the portable electronic device 102 independent of movement of the lock mechanism 112. By way of non-limiting example, as shown in the embodiments illustrated in FIGS. 41-43, the frame 106 could include at least one preassembly mechanism, generally indicated at 224, for urging the glass panel 114 into abutment with the touchscreen interface 104 when the sterilizable enclosure 100 is in either the closed position 100A or the opened position 100B (FIGS. 41-43 are shown with the base 110 omitted for clarity). Moreover, the preassembly mechanism 224 could cooperate with the lock mechanism 112 and/or the bias mechanism 162 to ensure proper abutment between the glass panel 114 and the touchscreen interface 104, as noted above. To that end, the preassembly mechanism 224 could include one or more arms 226 that secure the portable electronic device 102 to the frame 106 independent of the base 110. The arms 226 could be rotatably actuated to engage the portable electronic device 102 (see FIGS. 41 and 42), could be actuated with a linkage system, generally indicated at 228 (see FIG. 43), or could otherwise be actuated in any suitable way.

Referring again to FIGS. 1-20C, as noted above, the sterilizable enclosure 100 employs the seal 116 for engaging between the base 110 and the frame 106 so as to prevent ingress and egress of contaminants to and from the secured portable electronic device 102 when the sterilizable enclosure 100 is locked in the closed position 100A. As best shown in FIGS. 5, 13, 15, and 16, in one embodiment, at least one of the base 110 and the frame 106 includes a channel, generally indicated at 230, for at least partially receiving the seal 116 therein. In the representative embodiment illustrated herein, the channel 230 is defined in the base 110 of the sterilizable enclosure 100, has a generally rectangular profile, and is shaped complimentarily to the seal 116.

In one embodiment, at least one of the base 110 and the frame 106 includes an engagement element, generally indicated at 232, which is shaped to engage the seal 116 when the sterilizable enclosure 100 is in the closed position 100A. In the representative embodiment illustrated herein, the engagement element 232 is formed integrally with the frame 106, has a generally rectangular profile, and is shaped complimentarily to the seal 116. The shape, configuration, and arrangement of the seal 116, the channel 230, and the engagement element 232 advantageously defines a tortuous path from the outside environment toward the seal 116 when the sterilizable enclosure 100 is locked in the closed position 100A. It will be appreciated that the tortuous path contributes to increased opportunities to prevent contamination of the portable electronic device 102 and/or prevent contamination of the operating room, thereby making it difficult for pathogens, contaminants, and the like to traverse to and/or from the seal 116 and the outside environment. Nevertheless, as will be appreciated from the subsequent description below, the channel 230 and/or the engagement element 232 could have any suitable profile, shape, or configuration sufficient to engage the seal 116, as noted above. By way of non-limiting example, the engagement element 232 could be defined by one or more surfaces arranged to engage the seal 116. Moreover, while the channel 230 is formed in the base 110 and the engagement element 232 is depicted as being operatively attached to the frame 106, it will be appreciated that this arrangement could be interchanged.

Figure 27:
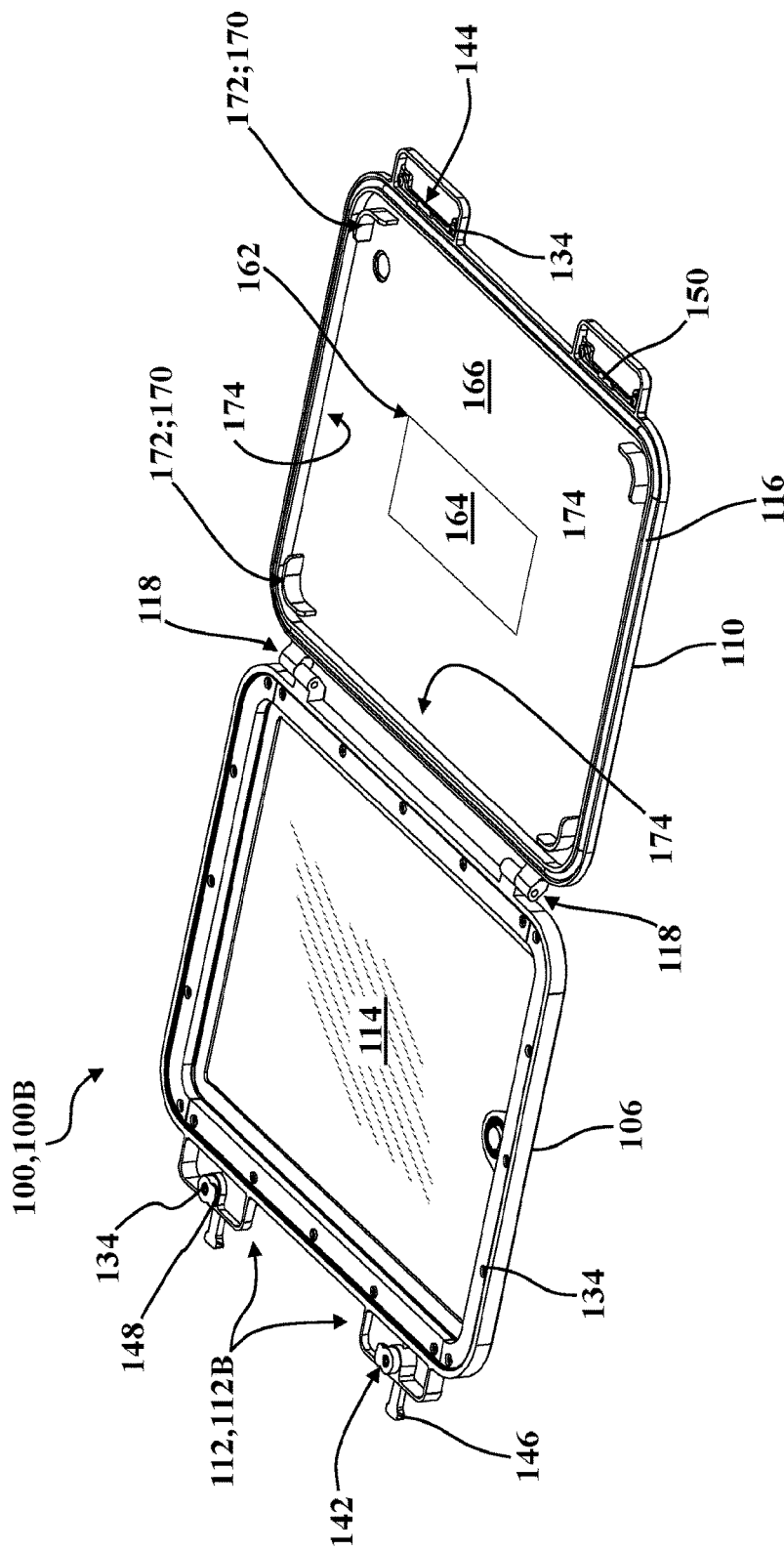
FIG. 27 is a bottom-side perspective view of the sterilizable enclosure of FIG. 26.
Figure 28:
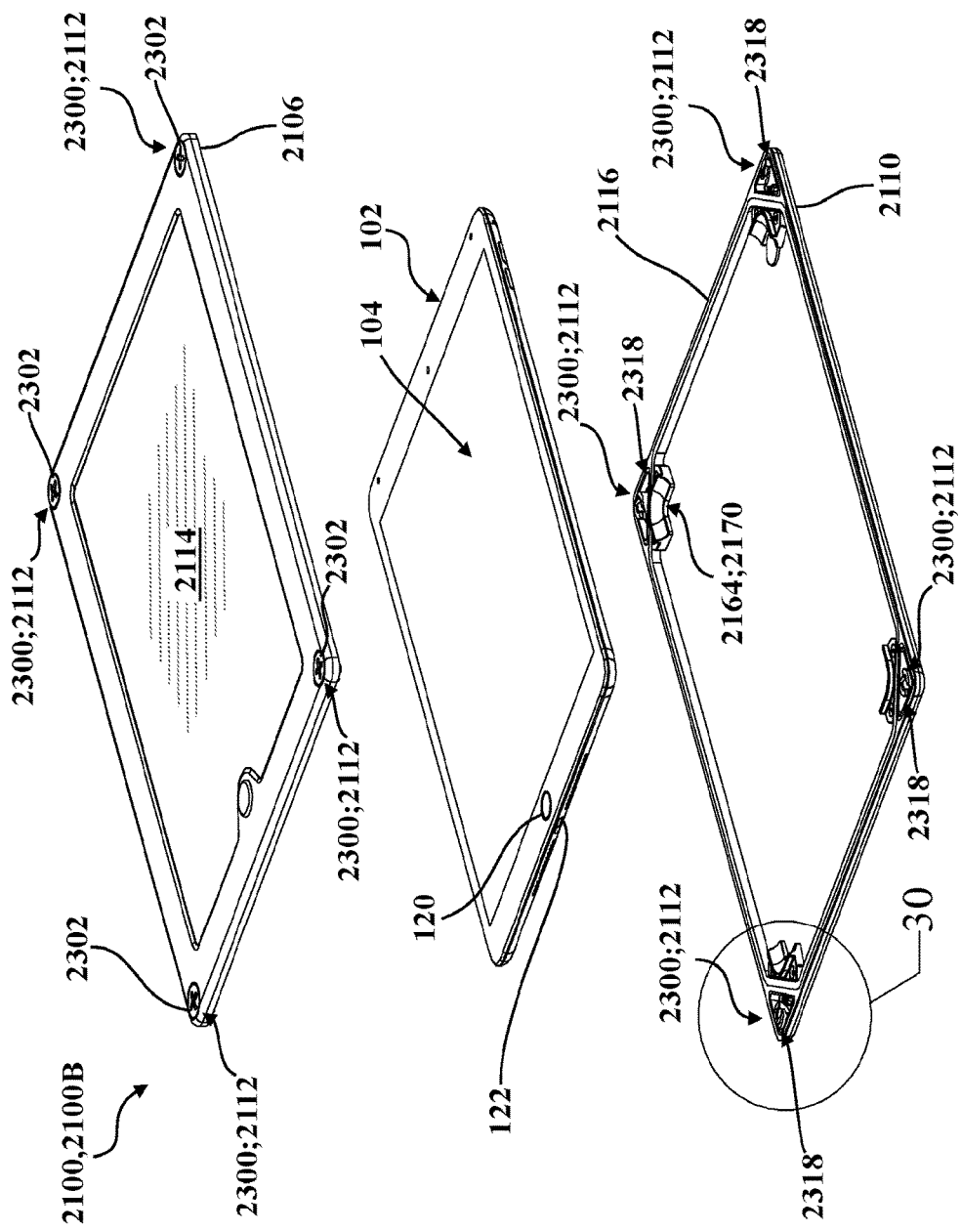
FIG. 28 is a top-side partially-exploded perspective view of a sterilizable enclosure according to another embodiment, showing a base and a frame spaced from each other with a portable electronic device arranged between the base and the frame.
Figure 29:
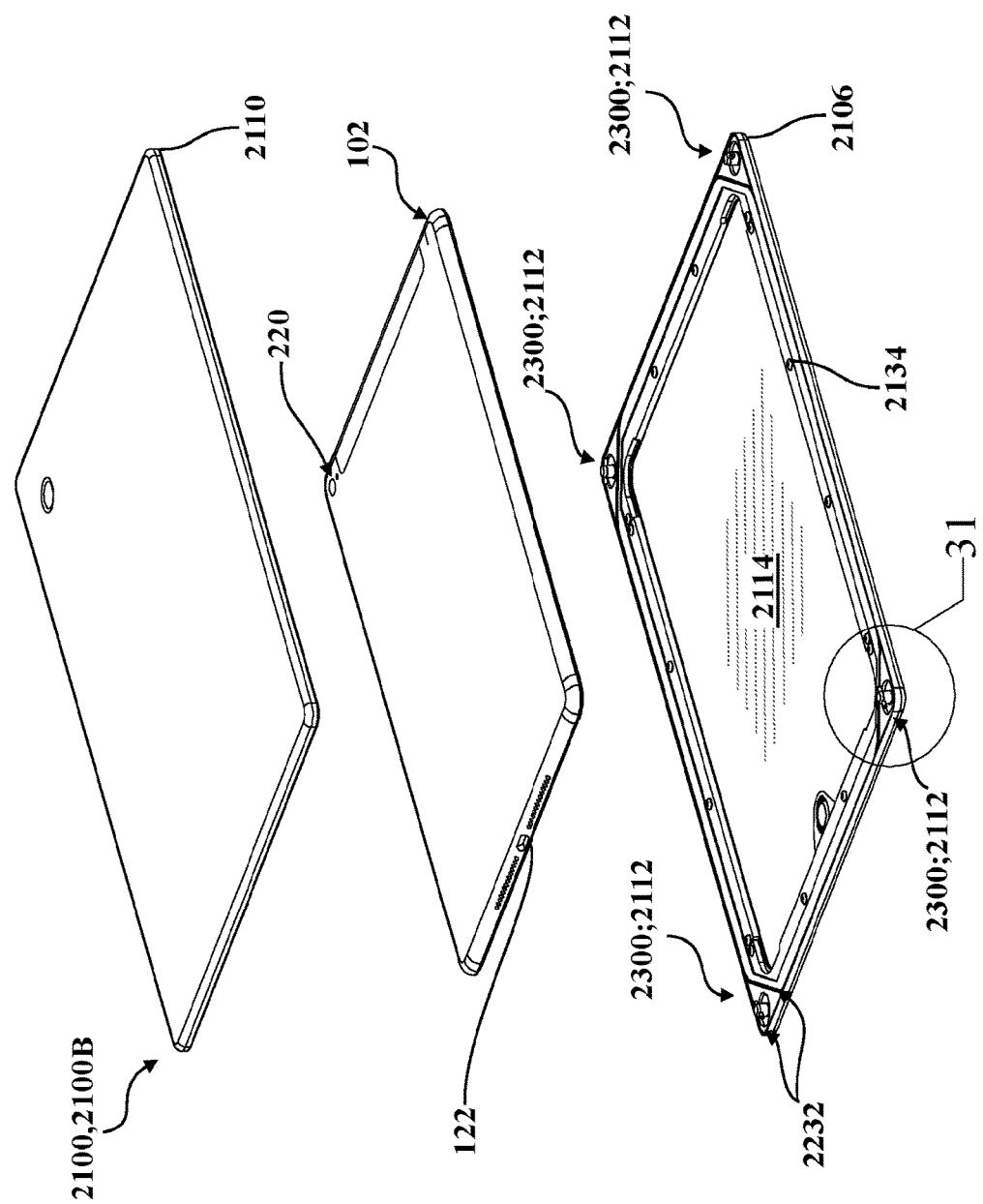
FIG. 29 is a bottom-side partially-exploded perspective view of the sterilizable enclosure and portable electronic device of FIG. 28.

In the representative embodiment, the seal 116 is advantageously realized as a unitary, one-piece, endless component, and may have a generally oval-shaped cross-sectional profile, as shown in FIGS. 15-17B. The gasket 116 may also be provided with structural features which promote retention of the gasket 116, such as spaced-apart ribs (not shown in detail). It will be appreciated that the seal 116 could have other profiles, such as an annular profile as depicted in FIG. 27, or another profile as is described in greater detail below in connection with the embodiment depicted in FIGS. 28-36. In one embodiment, the seal 116 is formed of silicon rubber. The seal 116 is capable of withstanding repeated steam sterilization in an autoclave, in which the seal 116 is subjected to a temperature of 134 degrees Celsius for 3 minutes or subjected to a temperature of 121 degrees Celsius for 15 minutes. In one embodiment, the seal 116 comprises a material with a melting point greater than 130 degrees Celsius, such as 150 degrees Celsius. The seal 116 may be configured to withstand all known decontamination methods for medical equipment, or only specific decontamination methods. The seal 116 could be arranged, configured, or otherwise realized from any suitable number of components, could be manufactured from any suitable material, and could have any suitable profile and/or shape sufficient to prevent ingress and egress of contaminants in a sterile, medical/surgical environment. Similarly, it will be appreciated that the seal 116 could be configured to be replaced or serviced after a predetermined amount of time and/or use, depending on the specific design and configuration of the sterilizable enclosure 100.

Figure 23:
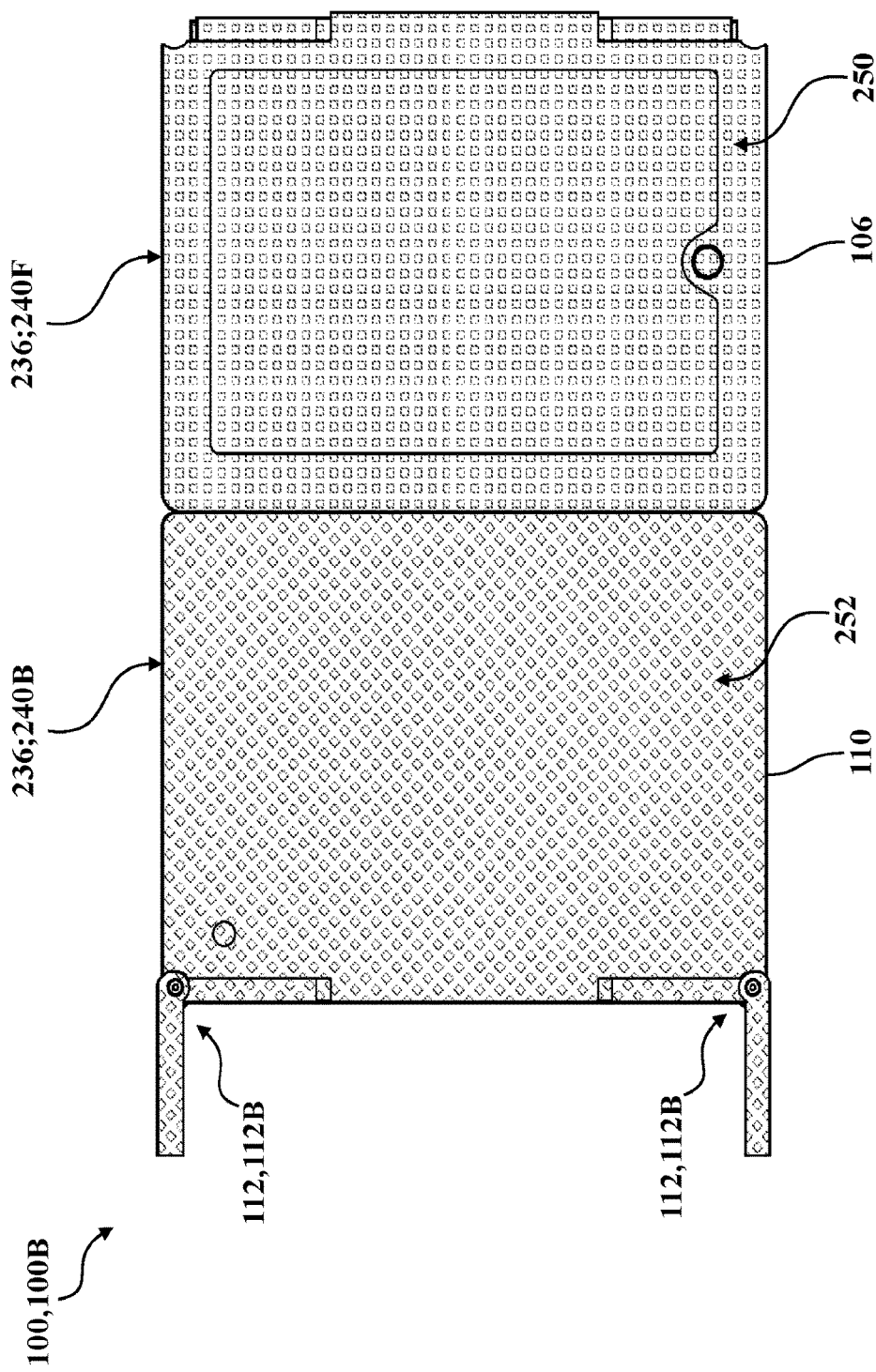
FIG. 23 is a bottom-side plan view of the sterilizable enclosure of FIG. 10, shown in the opened position with the lock mechanism in the unlocked configuration, and depicting a no-touch zone of the sterilizable enclosure.
Figure 24:
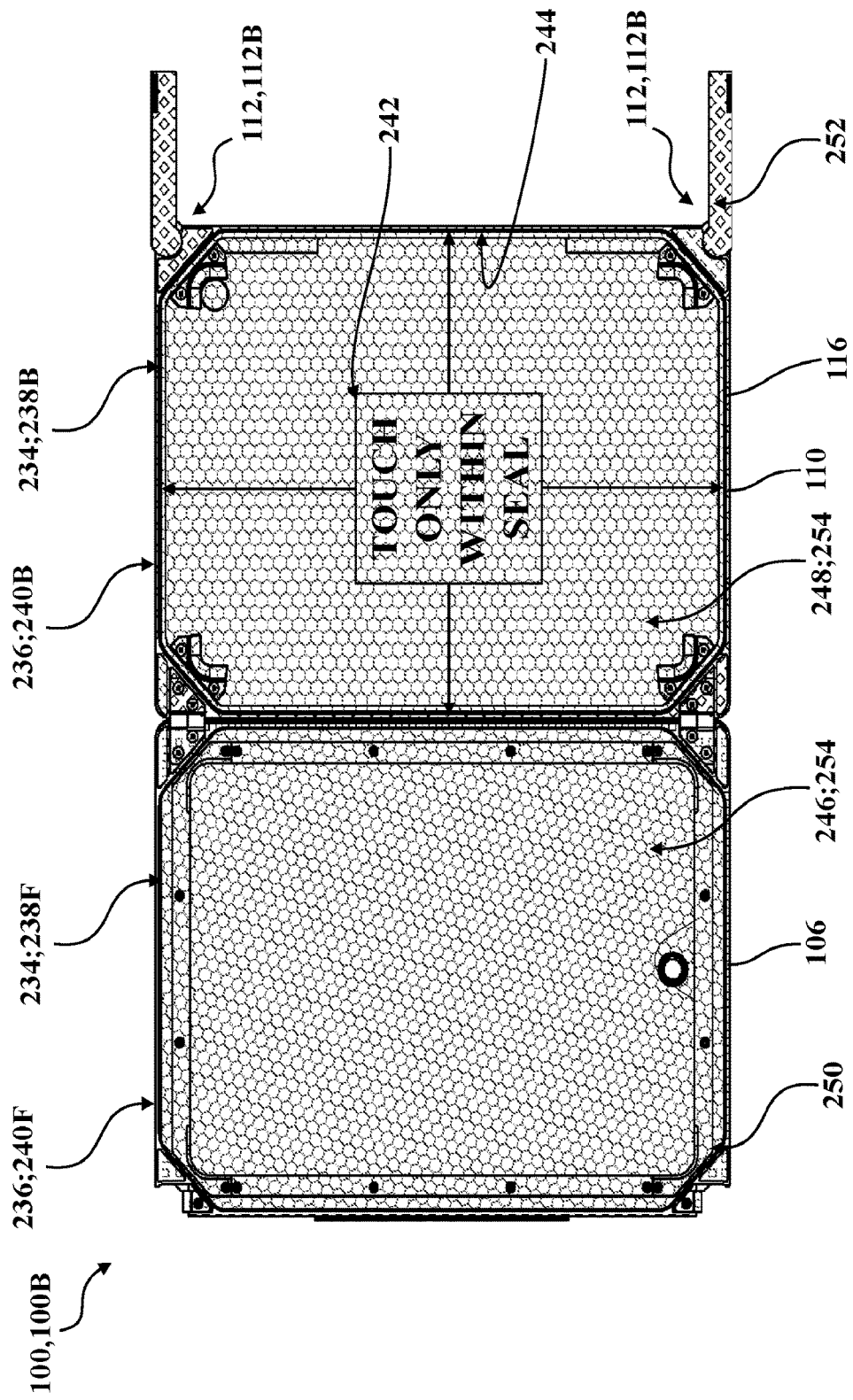
FIG. 24 is a top-side plan view of the sterilizable enclosure of FIG. 23, depicting portions of the no-touch zone of the sterilizable enclosure, and depicting an indicia within a touch zone of the sterilizable enclosure.
Figure 25:
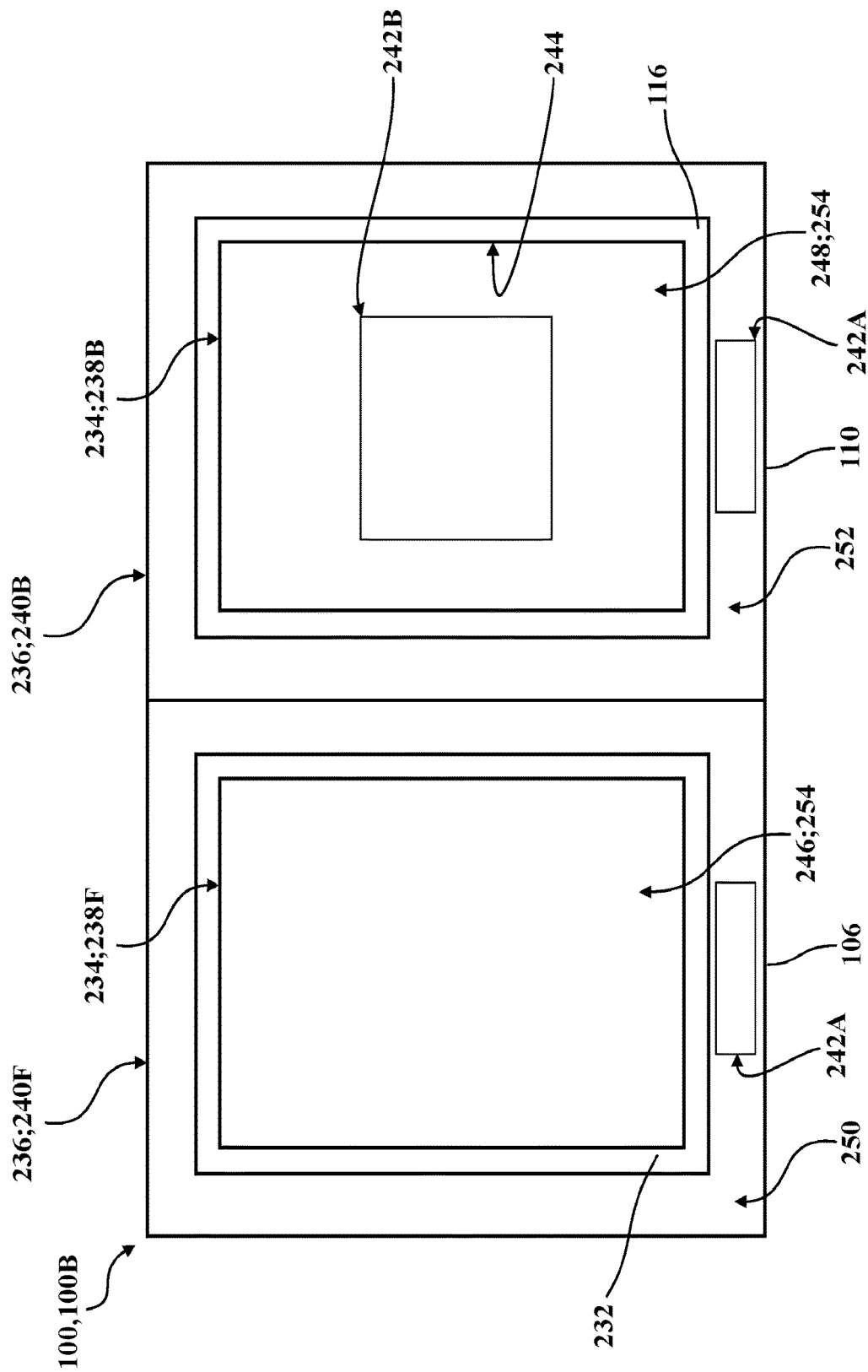
FIG. 25 is a schematic representation of one embodiment of the sterilizable enclosure, depicting a base and a frame arranged in an opened position with each of the base and the frame having an indicia.
Figure 26:
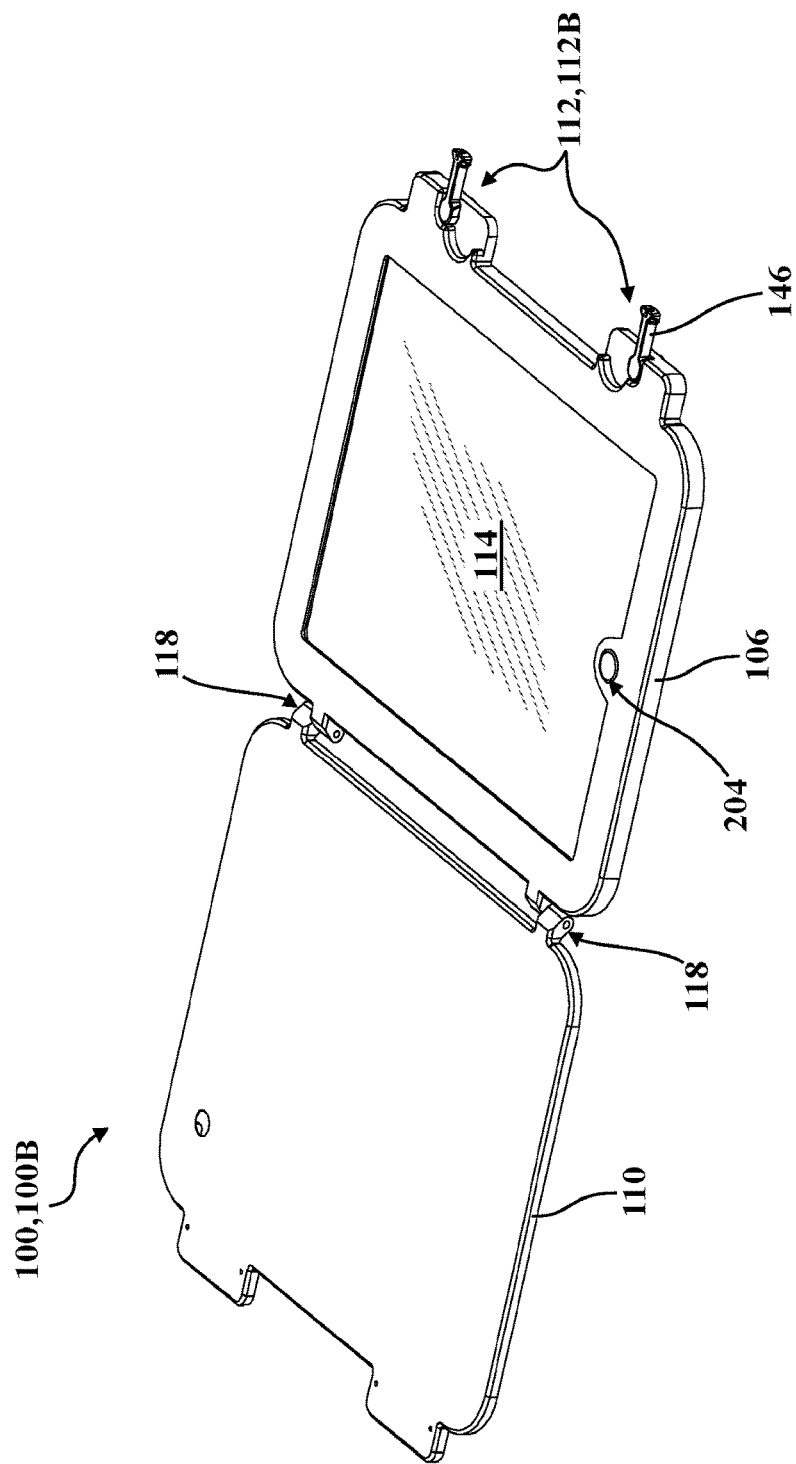
FIG. 26 is a top-side perspective view of a sterilizable enclosure according to another embodiment, showing a base pivotally coupled to a frame with the base and the frame arranged in an opened position, and a lock mechanism shown in an unlocked configuration.

Referring now to FIGS. 23-25, in one embodiment, the seal 116 and the engagement element 232 each define a boundary between a touch zone 234 and a no-touch zone 236. As will be appreciated from the subsequent description below, the touch zone 234 and the no-touch zone 236 are provided so as to encourage proper handling of the sterilizable enclosure 100 during loading of the portable electronic device 102, as well as during removal of the portable electronic device 102. Here, the touch zone 234 comprises first portions of the base 238B and first portions of the frame 238F, and the no-touch zone 236 comprises second portions of the base 240B and second portions of the frame 240F. In the representative embodiment shown in FIGS. 23 and 24, for the purposes of clarity, consistency, and illustration, the touch zone 234 is depicted as a repeating hexagon-shaped pattern (see FIG. 24) and the no-touch zone 236 is depicted as a repeating square-shaped pattern (see FIGS. 23 and 24). More specifically, the first portions of the base 238B and the first portions of the frame 238F are each depicted with a repeating hexagon-shaped pattern and are differentiated in that the repeating hexagon-shaped pattern of the first portions of the frame 238F is rotated at 45-degrees with respect to the repeating hexagon-shaped pattern of the first portions of the base 238B (see FIG. 24). Similarly, the second portions of the base 240B and the second portions of the frame 240F are each depicted with a repeating square-shaped pattern and are differentiated in that the repeating square-shaped pattern of the second portions of the frame 240F is rotated at 45-degrees with respect to the repeating square-shaped pattern of the second portions of the base 240B (see FIGS. 23 and 24).

In this embodiment, the sterilizable enclosure 100 further comprises a visual indicia, generally indicated at 242 (see FIG. 25), which is configured to differentiate the first portions 238B, 238F of the touch zone 234 from the second portions 240B, 240F of the no-touch zone 236 so as to promote contact only within the first portions 238B, 238F of the base 110 and the frame 106 of the sterilizable enclosure 100.

As noted above, the sterilizable enclosure 100 is configured to allow the portable electronic device 102, which is considered non-sterile, to be secured in the sterilizable enclosure 100 in such a way that sterility of the no-touch zone 236 of the sterilizable enclosure 100 is not compromised, thereby allowing the secured portable electronic device 102 to be subsequently used in sterile and/or aseptic environments. Moreover, as is described in detail below, the sterilizable enclosure 100 is further configured such that after the sterilizable enclosure 100 has been used in a contaminated environment, the secured portable electronic device 102 can be removed from the sterilizable enclosure 100 without subsequently exposing the portable electronic device 102, or the user handling the portable electronic device 102, to contaminants. To these ends, and by way of illustration, when the sterilizable enclosure 100 is used, sterilization or other types of decontamination are employed to ensure that both the first portions 238B, 238F and the second portions 240B, 240F of the touch zone 234 and the no-touch zone 236, respectively, have a desired level of sterility assurance or log reduction of micro-organisms, as described in greater detail below. Next, the portable electronic device 102, which is considered non-sterile at all times, is placed within the touch zone 234 with the sterilizable enclosure 100 in the fully opened position 100B (see FIG. 24; see also FIG. 5). Here, as is described in greater detail below, the indicia 242 are advantageously provided to direct a non-sterile user to only touch within the touch zone 234 and, conversely, not to touch the no-touch zone 236. The sterilizable enclosure 100 can then be moved to the closed position 100A to secure the portable electronic device 102 within the touch zone 234. Here, when the sterilizable enclosure 100 is first locked in the closed position 100A (see FIG. 8), the no-touch zone 236 of sterilizable enclosure 100 remains sterile until use subsequently potentially exposes the no-touch zone 236 to contaminants. Nevertheless, contaminants are prevented both from leaving the touch zone 234 and from entering the touch zone 246 via the seal 116 and/or the tortious path described above.

Conversely, the portions of the no-touch zone 236 which are exposed to the outside environment may be exposed to contaminants, such as micro-organisms, pathogens, blood, tissue, and the like, during use of the sterilizable enclosure 100, such as in an operating room. However, as noted above, the engagement of the seal 116 when locked in the closed position 100A prevents these contaminants from reaching the secured portable electronic device 102. When the user desires to remove the secured portable electronic device 102, the sterilizable enclosure 100 may be decontaminated, after which the sterilizable enclosure 100 may be moved into the opened position 100B (see FIG. 6). Here too, the indicia 242 are advantageously provided to direct the user to only touch within the touch zone 234 during removal of the portable electronic device 102. Thus, by avoiding contact with the potentially contaminated no-touch zone 236, the portable electronic device 102 can be removed from the sterilizable enclosure 100 without contaminating the portable electronic device 102 from exposure to contaminants, such as may be present in the operating room.

Figure 6:
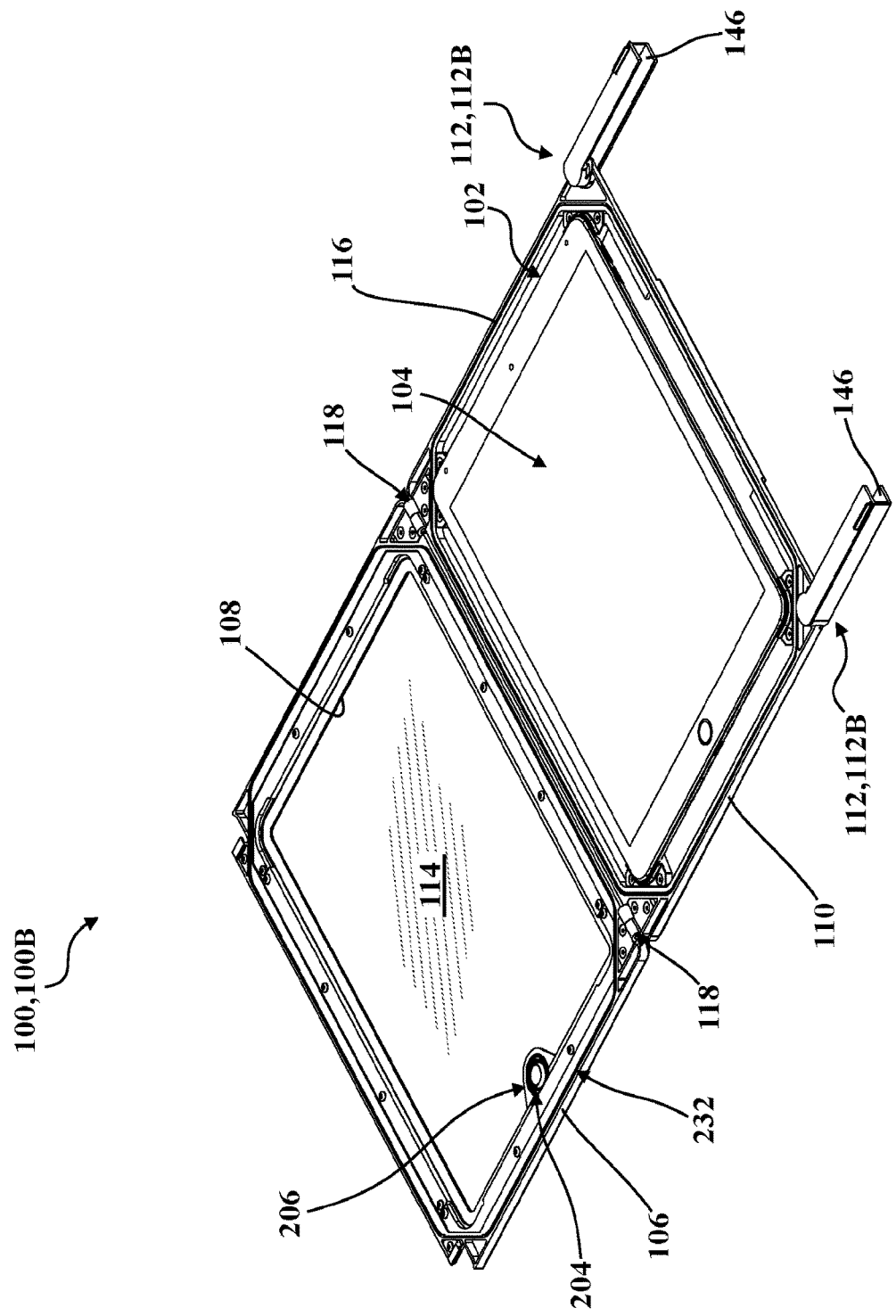
FIG. 6 is a top-side perspective view of the portable electronic device and sterilizable enclosure of FIG. 5, shown with the portable electronic device seated in the base.
Figure 7:
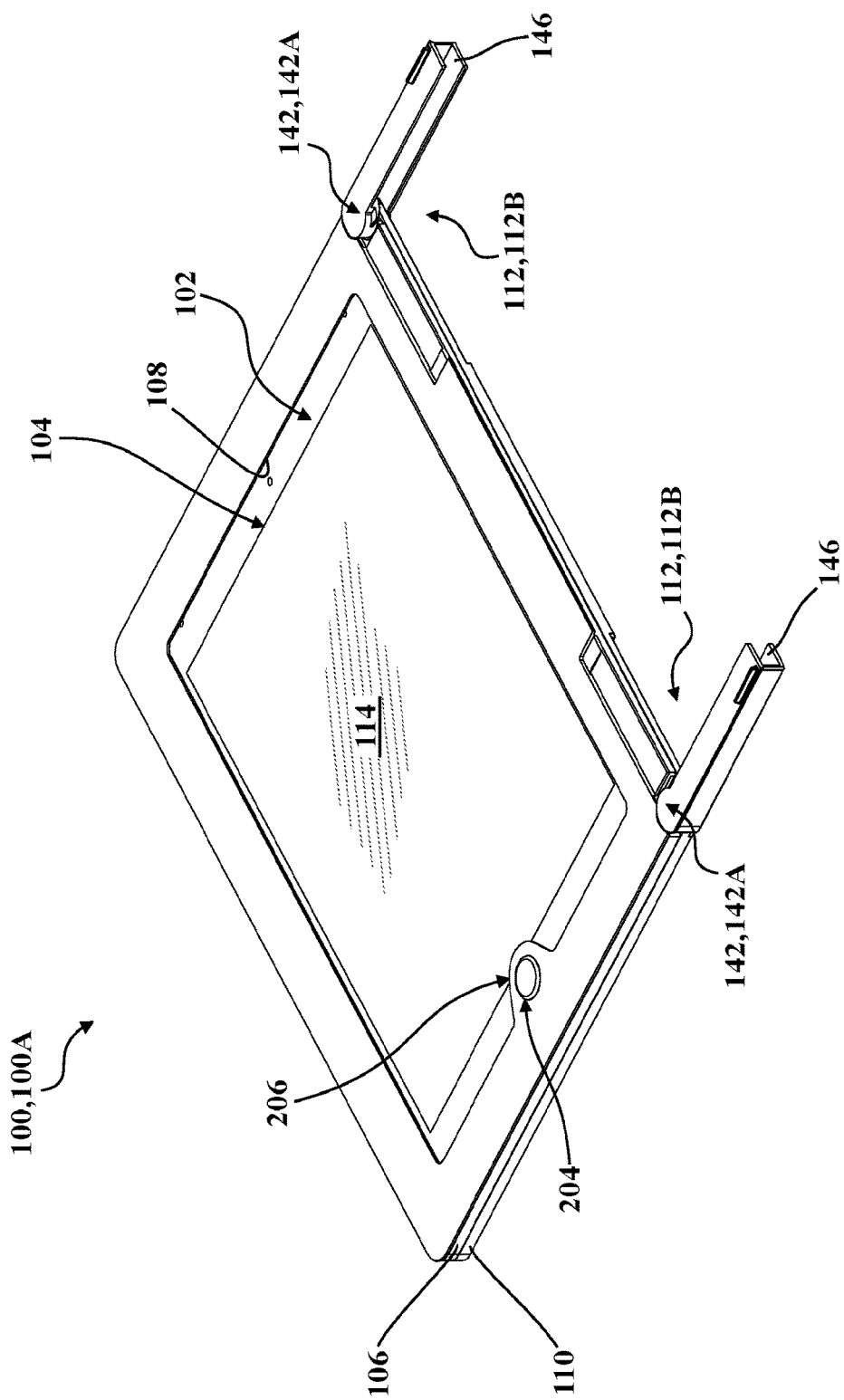
FIG. 7 is a top-side perspective view of the portable electronic device and sterilizable enclosure of FIG. 6, shown in the closed position with the lock mechanism in the unlocked configuration.

As shown best in FIG. 6, the tray 170, defined in this embodiment by the bias elements 164 of the bias mechanism 162 as noted above, is advantageously spaced inwardly from the seal 116 at a predetermined distance. It will be appreciated that this configuration contributes to ease in conforming to sterile protocol by providing handling room within the touch zone 234 (compare FIG. 6 to FIG. 24) to help prevent inadvertent contact within the no-touch zone 236 during both installation and removal of the portable electronic device 102. While the predetermined distance between the seal 116 and the tray 170 is substantially equidistant, it will be appreciated that different arrangements may be utilized in certain embodiments. For instance, left and right sides could be spaced so as to provide handling room for fingers, while top and bottom sides could be spaced differently, such as less than the spacing of the left and right sides.

With continued reference to FIGS. 23-25, in one embodiment, the indicia 242 is disposed on at least one of the first portions 238B, 238F of the base 110 and the frame 106 defining the touch zone 234. Put differently, one or both of the first portions 238B, 238F could be provided with indicia 242. In the representative embodiment illustrated in FIG. 24, the first portion 238B of the base 110 is provided with indicia 242 comprising text reading "TOUCH ONLY WITHIN SEAL", a box surrounding the text, and arrows extending from the box to the seal 116.

In the schematic representation depicted in FIG. 25, a first indicia 242A is disposed on at least one of the second portions 240B, 240F of the base 110 and the frame 106 defining the no-touch zone 236, and a second indicia 242B is disposed on at least one of the first portions 238B, 238F of the base 110 and the frame 106 defining the touch zone 234. Put differently, one or both of the second portions 240B, 240F could be provided with first indicia 242A of the same or different type, and one or both of the first portions 238B, 238F could be provided with second indicia 242B of the same or different type. The first indicia 242A provided within the no-touch zone 236 are configured to discourage contact within the no-touch zone 236 and may be configured to differentiate the no-touch zone 236 from the touch zone 234. The second indicia 242B provided within the touch zone 234 are configured to encourage contact within the touch zone 234 and may be configured to differentiate the touch zone 234 from the no-touch zone 236. In one embodiment, the first indicia 242A disposed on the second portions 240B, 240F of the base 110 and/or the frame 106 within the no-touch zone 236 are a first color (for example, red), and the second indicia 242B disposed on the first portions 238B, 238F of the base 110 and/or the frame 106 within the touch zone 234 are a second color (for example, green).

It will be appreciated that the indicia 242 could be provided in a number of different ways and with a number of different configurations. By way of non-limiting example, the indicia 242 could be realized by coloring applied only within the first portion 238B of the base 110 within the touch zone 234. Similarly, the indicia 242 could be realized a sticker, label, and the like. Furthermore, the indicia 242 could be realized as a texture, coating, paint, and the like. Further still, the indicia 242 may comprise one or more electronic devices that illuminate certain portions of the sterilizable enclosure that are present within the touch zone 234 or no-touch zone 236. It should be appreciated that the indicia 242 may include any modality that is visually detectable by a user.

In one embodiment, an inner periphery 244 of the seal 116 defines the boundary between the touch zone 234 and the no-touch zone 236. However, those having ordinary skill in the art will appreciate that components, structures, and the like, other than the seal 122 could be employed to differentiate the touch zone 234 from the no-touch zone 236 in certain embodiments. According to one embodiment, the touch zone 234 comprises a frame touch surface area 246 associated with the frame 106, and a base touch surface area 248 associated with the base 110; and the no-touch zone 236 comprises a frame no-touch surface area 250 associated with the frame 106, and a base no-touch surface area 252 associated with the base 110. Here, the frame touch surface area 246 and the base touch surface area 248 are defined by the surfaces of each of the components of the sterilizable enclosure 100 which are isolated from the outside environment by the seal 116 when the sterilizable enclosure 100 is locked in the closed position 100A, and the frame no-touch surface area 250 and the base no-touch surface area 252 are defined by the surfaces of each of the components of the sterilizable enclosure 100 which do not form part of the frame touch surface area 246 or the base touch surface area 248. Here, when the sterilizable enclosure 100 is locked in the closed position 100A, the frame touch surface area 246 and the base touch surface area 248 define a sealed volume 254 in which the secured portable electronic device 102 is accommodated.

In operation, in one embodiment, the portable electronic device 102 is prepared for use inside a sterile field during a surgical procedure. First, the sterilizable enclosure 100, which has previously been sterilized in a steam autoclave or other decontamination process, is located in a sterile area to receive the portable electronic device 102. The sterilizable enclosure 100 may be provided in the opened position 100B so that the portable electronic device 102 merely needs to be placed in the tray 170. In order to maintain sterility, this is done without allowing the portable electronic device 102 (or anyone touching the portable electronic device 102) to contact any surface of the sterilizable enclosure 100 outside of the touch zone 234, as described above. In some cases, non-sterile personnel are not allowed to reach over or carry any non-sterile object over any sterile surface, so shielding or covering of areas of the sterilizable enclosure 100 outside of the seal 116 may be utilized during loading. The sterilizable enclosure 100 is then moved to the closed position 100A. The sterilizable enclosure 100 is preferably closed without requiring any contact of the portable electronic device 102. Accordingly, contaminants on the portable electronic device 102 are contained within the sealed volume 254 of the sterilizable enclosure 100. The sterilizable enclosure 100 may be closed by someone that has taken steps to maintain sterility, e.g., such as scrubbed-in surgical staff or other personnel.

Figure 20A:
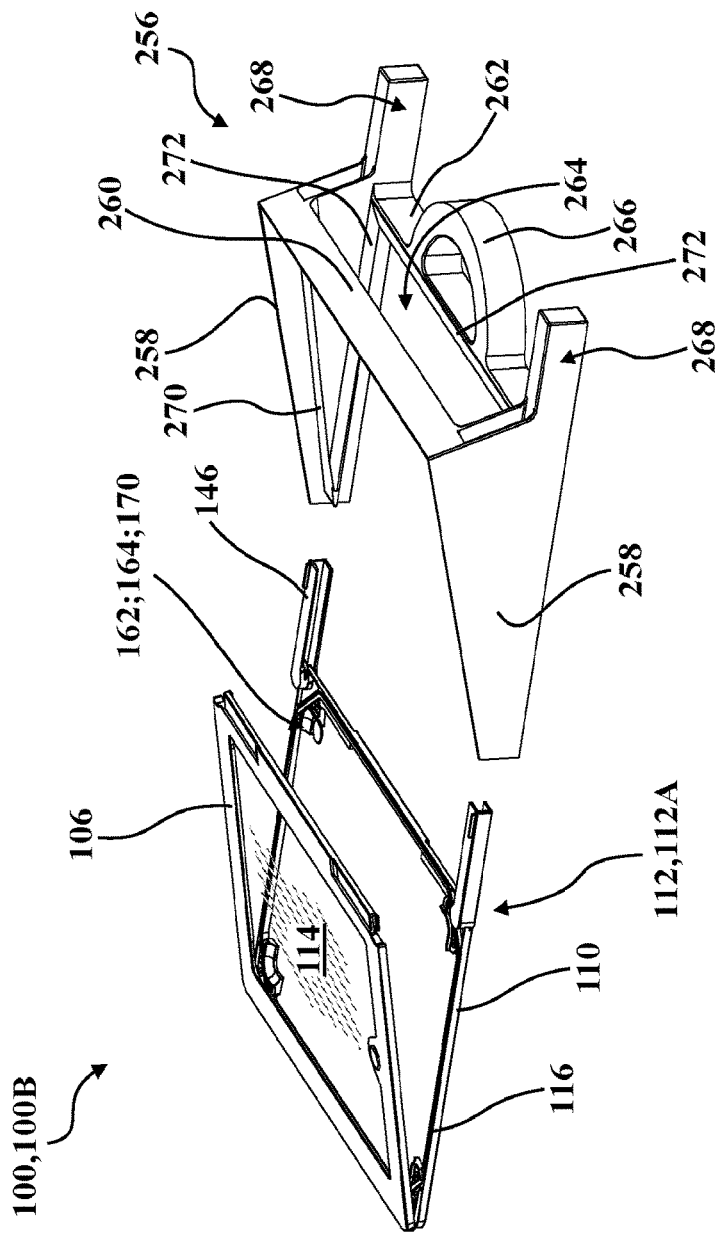
FIG. 20A is a perspective view of a transfer device according to one embodiment shown positioned adjacent to the sterilizable enclosure depicted in FIGS. 1-18E.
Figure 20B:
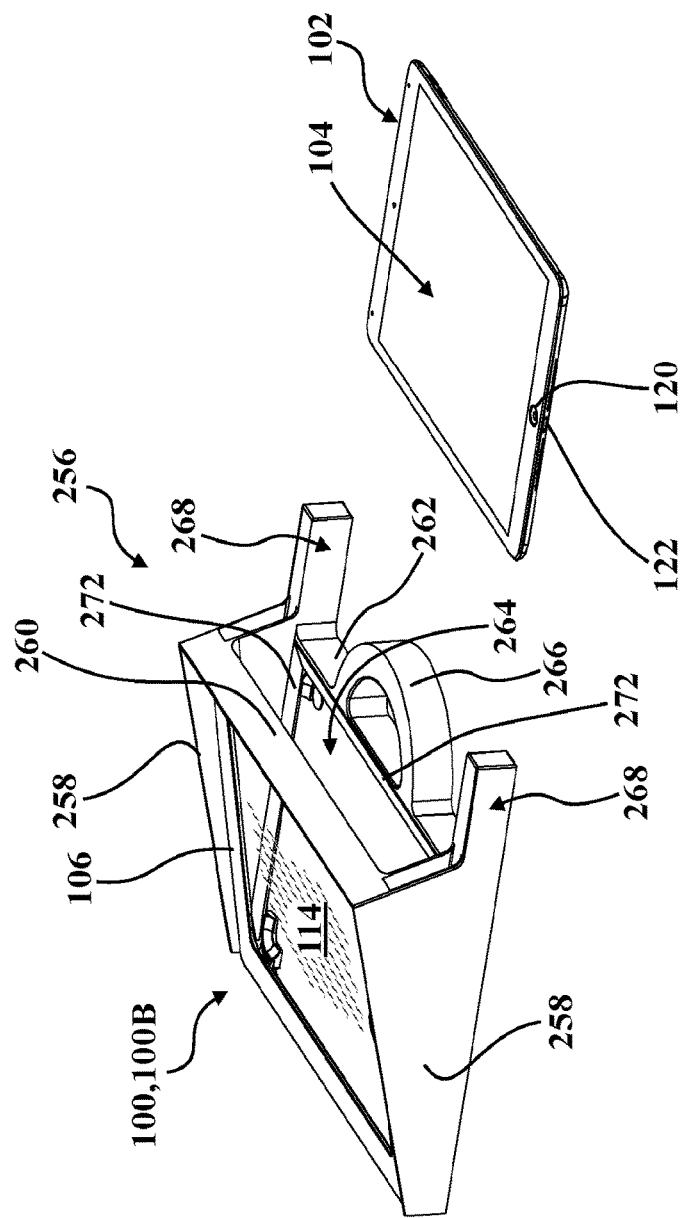
FIG. 20B is another perspective view of the transfer device and sterilizable enclosure of FIG. 20A, shown positioned adjacent to the portable electronic device of FIG. 5, with the sterilizable enclosure held open by the transfer device.
Figure 20C:
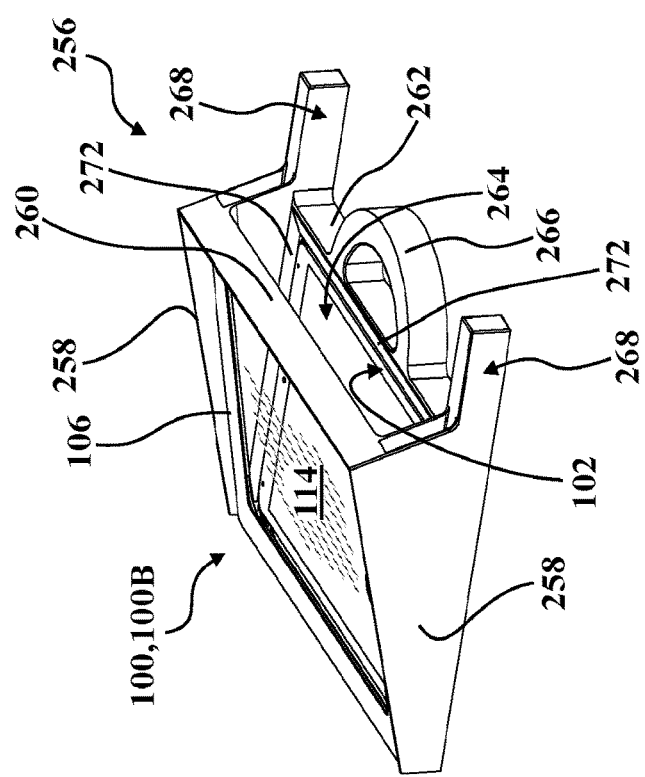
FIG. 20C is another perspective view of the transfer device, sterilizable enclosure, and portable electronic device of FIG. 20B, shown with the portable electronic device seated in the base of the sterilizable enclosure held open by the transfer device.
Figure 21:
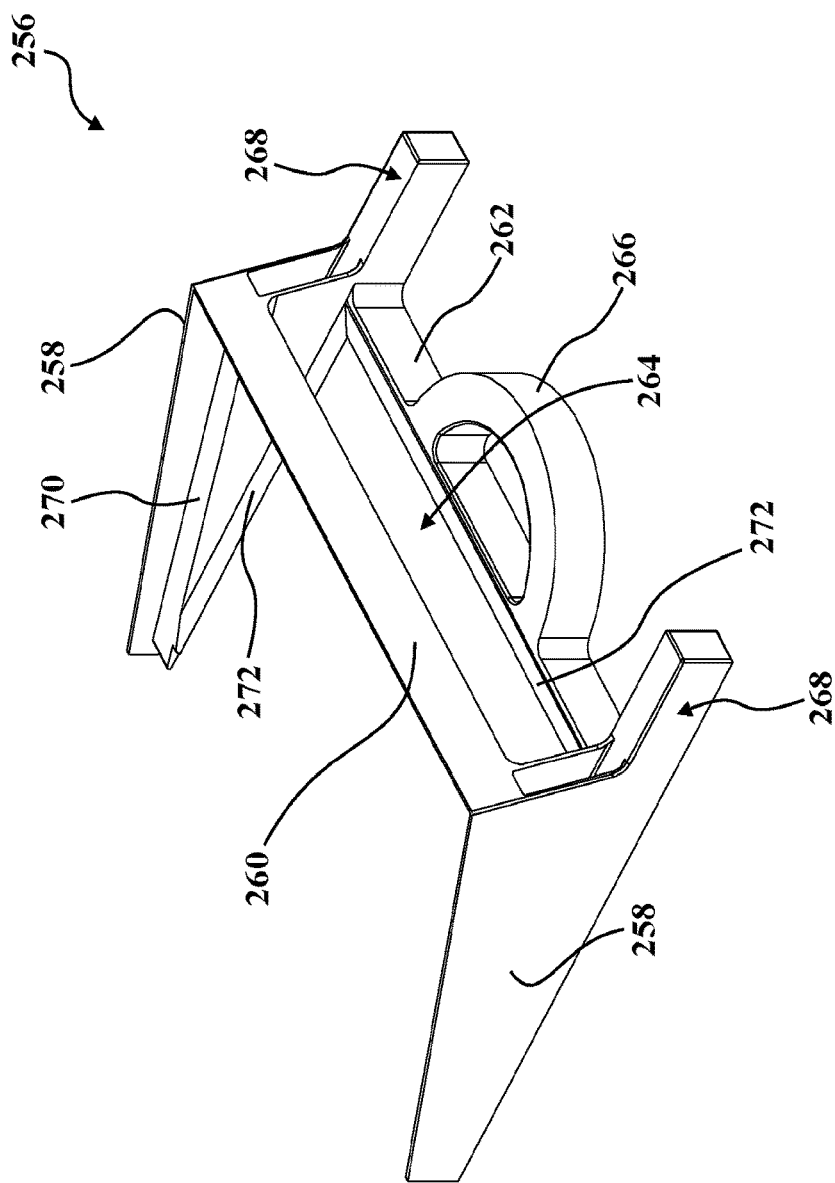
FIG. 21 is a top-side perspective view of the transfer device of FIGS. 20A-20C.
Figure 22:
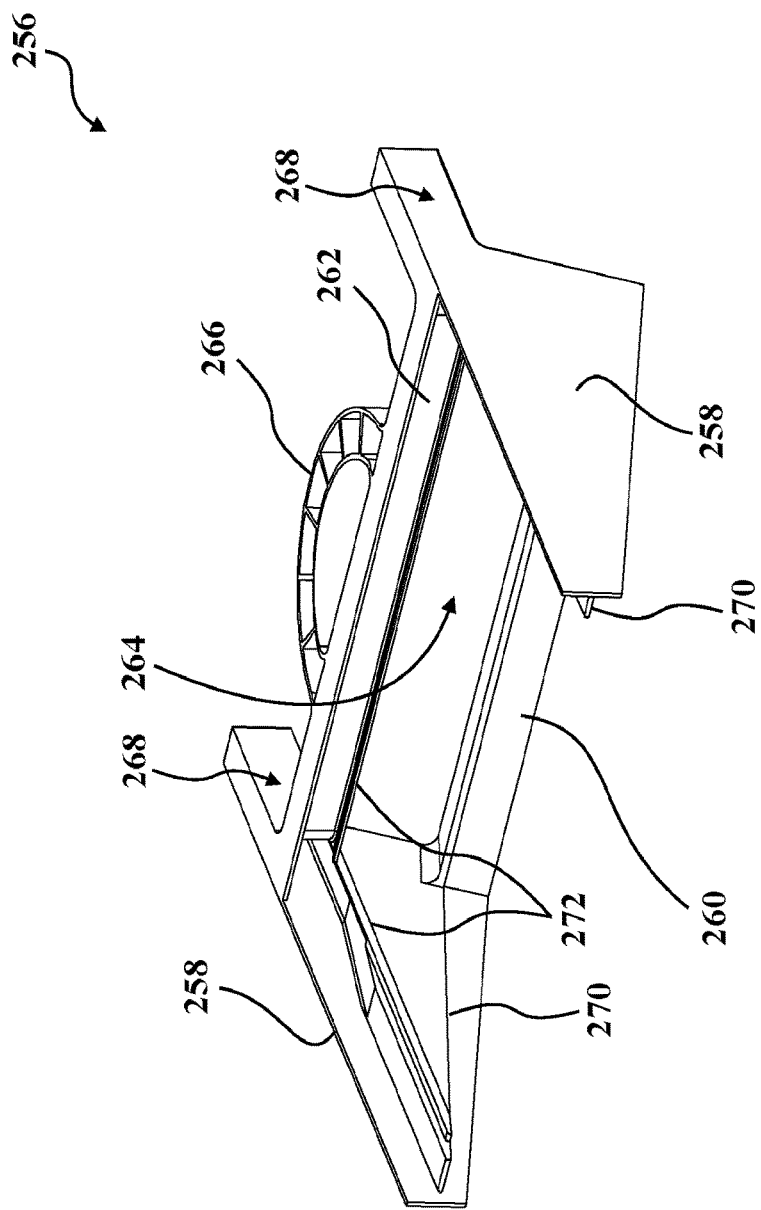
FIG. 22 is a bottom-side perspective view of the transfer device of FIGS. 20A-21.

Referring now to FIGS. 20A-22, in one embodiment, a transfer device 256 is provided for shielding at least a portion of the sterilizable enclosure 100 while holding the sterilizable enclosure 100 in the partially opened position 100B with the frame 106 pivoted away from the base 110. As is best shown in FIGS. 21 and 22, the transfer device 256 generally comprises a pair of outer walls 258, an upper wall 260 extending between and merging with the outer walls 258, and a lower wall 262 extending between and merging with the outer walls 258 spaced from the upper wall 260 to define a passage 264. A handle 266 is provided on the lower wall 262. A pair of hollow receptacles 268 are arranged adjacent to the handle 266 and are shaped to receive the latches 146 of the lock mechanism 112, as described in greater detail below. A pair of ramps 270 are provided on the outer walls 258 and extend inwardly towards each other. The ramps 270 are arranged to abut the frame 106 of the sterilizable enclosure 100, as described in greater detail below. Three cover elements 272 are provided, two of which extend towards each other from the outer walls 258 spaced below the ramps 270, and one of which extends from the lower wall 262 away from the handle 266. Those having ordinary skill in the art will appreciate that other configurations of the transfer device 256 are contemplated herein.

In use, the transfer device 256 is provided to hold the sterilizable enclosure 100 in the partially opened position 100B, as noted above. To this end, the sterilizable enclosure 100 is positioned adjacent to the transfer device 256 as depicted in FIG. 20A, with the latches 146 of the lock mechanism 112 facing towards the receptacles 268 of the transfer device 256. Next, the sterilizable enclosure 100 is brought into contact with the transfer device 256 such that the transfer device 256 holds the sterilizable enclosure 100 in the opened position 100B. To that end, the ramps 270 abut top and bottom edges of the frame 106, a portion of the upper wall 260 abuts a right edge of the frame 106, and a portion of the lower wall 262 supports a right edge of the base 110 (see FIG. 20B; see also FIG. 22). In this configuration, the cover elements 272 and the walls 258, 260, 262 cooperate to cover, shield, or otherwise obstruct access to certain portions of the sterilizable enclosure 100. In particular, and as is described in greater detail below, when viewed facing towards the passage 264, the transfer device advantageously restricts user to and prevents contact with the no-touch zone 236 of the sterilizable enclosure 100, e.g., users such as non-sterile personnel. Once the sterilizable enclosure 100 is held in the opened position 100B, the portable electronic device 102 is brought towards the transfer device 256 and is inserted through the passage 264 into the tray 170 of the sterilizable enclosure 100 (see FIG. 20C).

Here, the cover elements 272 are advantageously angled to promote alignment of the portable electronic device 102 with respect to the base 110 of the sterilizable enclosure 100. Subsequently, the handle 266 can be grasped to pull the transfer device 256 away from the sterilizable enclosure 100. As the transfer device 256 is moved away from the sterilizable enclosure 100, the ramps 270 come out of contact with the frame 106 and gravity causes the frame 106 to move towards the base 110 such that the sterilizable enclosure 100 moves towards the closed position 100A.

The transfer device 256 is advantageously manufactured as a unitary, one-piece component, comprised of a material which can withstand autoclave sterilization, as noted above. The sterilizable enclosure 100 and the transfer device 256 can be sterilized together, such as in a common container. Here, because the transfer device 256 holds the sterilizable enclosure 100 in the opened position 100B, vacuum locking of the sterilizable enclosure 100 is prevented, such as may otherwise occur during an autoclave process. Alternatively, the sterilizable enclosure 100 and the transfer device 256 can be sterilized separately and then subsequently used. It will be appreciated that the transfer device 256 could also be designed as a sterile, disposable, one-time-use article.

In one embodiment, securing the portable electronic device 102 within the sterilizable enclosure 100 via the transfer device 256 is achieved with two users: a sterile user and a non-sterile user. Here, the sterile user advantageously only handles the sterilizable enclosure 100, and the non-sterile user advantageously only handles the transfer device 256 and the portable electronic device 102. However, at the onset, the sterile user could handle both the previously-sterilized transfer device 256 and the previously-sterilized sterilizable enclosure 100, such as may be required to position the transfer device 256 and sterilizable enclosure 100 in the orientation depicted in FIG. 20B. Here, the shape and configuration of the transfer device 256 advantageously inhibits the sterile user from accessing the previously-described touch zone 234 (see FIG. 24) as they hold the base 110 and the frame 106 of the sterilizable enclosure 100. Specifically, the outer walls 258 are shaped so as to prevent the sterile user from positioning their hands between the base 110 and the frame 106 as they grasp the base 110 and the frame 106. Once the sterile user holds the sterilizable enclosure 100 in the position depicted in FIG. 20B, with the transfer device 256 supported on the sterilizable enclosure 100 and with the passage 264 facing towards the non-sterile user, the non-sterile user can insert the portable electronic device 102 through the passage 264. Here, the cover elements 272 help guide the portable electronic device 102 into position such that the non-sterile user's hands need not enter the passage 264. Once the portable electronic device 102 is supported on the base 110, the non-sterile user can grasp the handle 266 of the transfer device 256 while the sterile user continues to support the sterilizable enclosure 100. As the non-sterile user pulls the handle 266 to move the transfer device 256 away from the sterilizable enclosure 100, gravity moves the sterilizable enclosure 100 towards the closed position 100A, as noted above. The sterile user can then lock the sterilizable enclosure 100 in the closed position 100A to effect the capacitive coupling and to engage the seal 116, as described above.

In one embodiment, the sterilizable enclosure 100 is capable of satisfying design and performance standards for sterilization containment devices, ANSI/AAMI ST77. While the term "decontamination" as used herein refers to removal or killing of any amount of micro-organisms, "sterilization" is a specific level of decontamination that has been empirically determined as an acceptable level of destruction of micro-organisms for certain applications. Examples of the acceptable sterilization process conditions can include a 3-log reduction in micro-organisms, a 6-log reduction in micro-organisms, or a 12-log reduction in micro-organisms. A "validated sterilization process" is understood to be a sterilization process that, based on past testing, is known to sterilize a particular instrument to a desired level of sterilization that essentially ensures any microbial material on the instrument would be innocuous. By way of non-limiting example, a surgical instrument is often considered sterilized if the instrument has a desired level of sterilization corresponding to a 6-log reduction in micro-organisms. This means that the micro-organism population on the instrument was likely reduced by at least 99.9999%. U.S. Patent Publication No. 2015/0374868, hereby incorporated by reference, provides an explanation of how to obtain environmental measurements for a validated sterilization process.

However, it will be appreciated that the desired level of sterilization can be higher or lower than these exemplary reductions in micro-organisms as necessary for particular applications. Moreover, it will be appreciated that this disclosure is directed to sterilizable enclosures 100 adapted for use in a broad number of applications where it is desirable to use portable electronic devices 102 and where decontamination is required, such as an entire room for medical or non-medical applications. Non-limiting examples of non-medical applications requiring sterilization can include an ambulance, a manufacturing facility for computers, an aircraft, and a post office.

In certain embodiments, decontamination of the sterilizable enclosure 100 may be less stringent than steam autoclave and other rigorous methods of sterilization. For instance, in some cases, the sterilizable enclosure 100 may be decontaminated by hand using detergents, using an automated washer/disinfector, hand wipes, alcohol wipes, or other forms of manual cleaning. These other forms of cleaning may be useful to users that are hesitant to directly clean their portable electronic devices for fear of damage. In these cases, the embodiments of the sterilizable enclosure 100 described herein can significantly improve disinfection since the portable electronic device 102 is safely secure in the sterilizable enclosure 100 before cleaning, and thus able to be exposed to such cleaning methods without damage.

As noted above, the present disclosure is directed, generally, towards at least two types of sterilizable enclosures: the first type in which the base 110 and the frame 106 are pivotally attached to each other via one or more hinges 118 as depicted in FIGS. 1-20, 23-24, and 26-27, and the second type without hinges as depicted in FIGS. 28-36 and 39-40. As will be appreciated from the subsequent description below, the various components, structural features, configurations, arrangements, and the like of each of the sterilizable enclosures described herein and illustrated throughout the drawings can be interchanged for certain applications. Thus, in the following description of the embodiments depicted in FIGS. 28-36 and 39-40, the structure and components that are the same as or that otherwise correspond to the structure and components of the embodiments depicted in FIGS. 1-20, 23-24, and 26-27 are provided with the same reference numerals increased by 2000.

Referring now to FIGS. 28-36 and 39-40, certain embodiments of the second type of sterilizable enclosure 2100 are shown. As noted above, the second type of sterilizable enclosure 2100 is substantially similar to the first type of sterilizable enclosure 100 described above, but lacks hinges 118. Thus, for the purposes of clarity and consistency, only the specific differences between the second type of sterilizable enclosure 2100 and the first type of sterilizable enclosure 100 will be described below and only certain structural features and components common between the types will be discussed herein and depicted in the drawings. Unless otherwise indicated below, it will be appreciated that the description of the first type of sterilizable enclosure 100 above may be incorporated by reference with respect to the second type of the sterilizable enclosure 2100 without limitation.

With continued reference to FIGS. 28-36 and 39-40, as noted above, the sterilizable enclosure 2100 omits pivoting between the base 2110 and the frame 2106 in these embodiments and employs a corner lock arrangement, generally indicated at 2300, to "sandwich" and capture the secured portable electronic device 102 between the base 2110 and the frame 2106 in the closed position 2100A (see FIGS. 28, 29, and 32-36) with the touchscreen interface 104 engaging the glass panel 2114. The corner lock arrangement 2300 comprises four discrete lock mechanisms 2112. Each lock mechanism 2112 comprises a first lock element, generally indicated at 2142 (see FIGS. 31, 35, and 36), and a second lock element, generally indicated at 2144 (see FIGS. 30, 35, and 36). In this embodiment, the first lock elements 2142 are rotatably supported by the frame 2106 and the second lock elements 2144 are operatively attached to the base 2110, such as with fasteners 2134. However, those having ordinary skill in the art will appreciate that this arrangement could be interchanged for certain applications.

Figure 35:
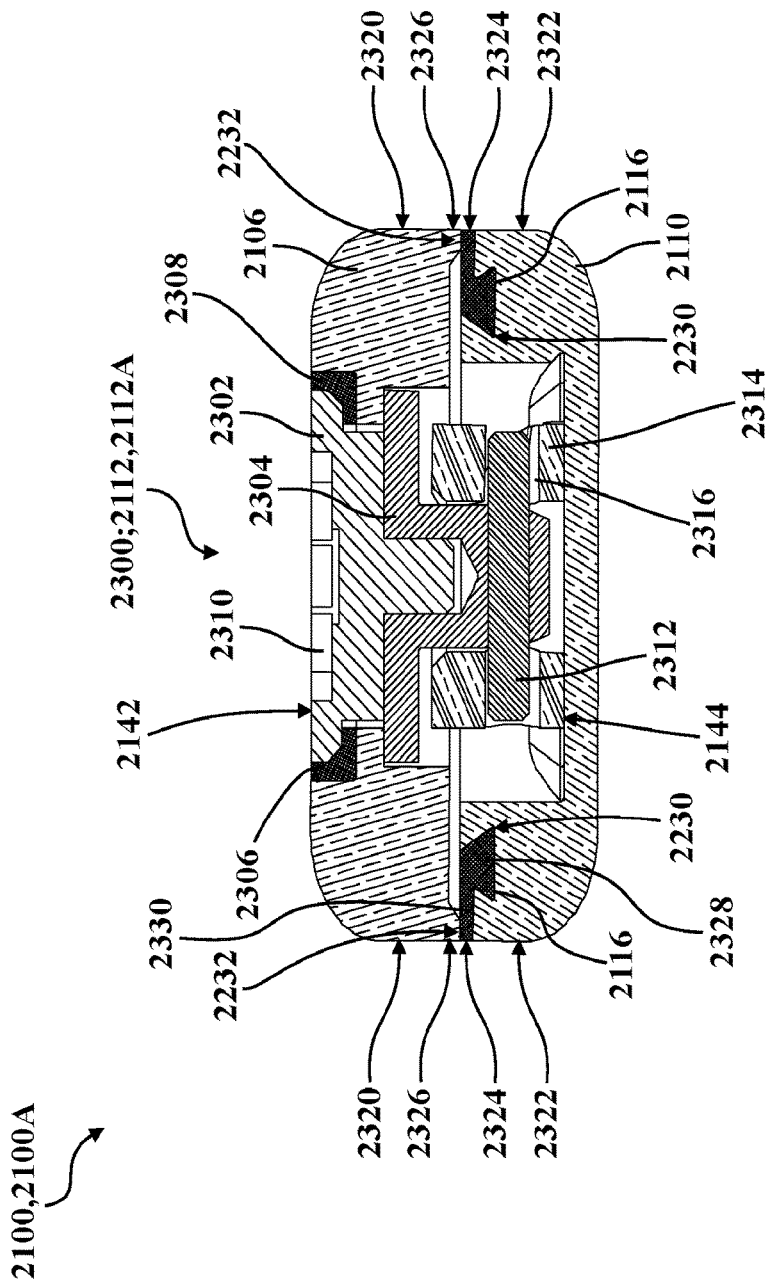
FIG. 35 is a sectional view taken along line 35-35 of FIG. 32.

As is best shown in FIG. 35, in this embodiment, the first lock elements 2142 of the sterilizable enclosure 2100 each comprise a twist latch 2302 operatively attached to a carrier 2304 for concurrent rotation. Each twist latch 2302 is accommodated in a blind bore 2306 formed in the frame 2106. A sealing washer 2308 is also supported in the blind bore 2306 and is complimentarily shaped to the twist latch 2302 and the blind bore 2306 so as to allow rotation of the twist latch 2302 and, at the same time, prevent contaminants from reaching the carrier 2304 (see also FIG. 36). The twist latch 2302 is advantageously arranged to be flush with the frame 2106, and comprises a drive formation 2310 (see FIG. 32) shaped to receive rotational torque from a tool, such as a conventional screwdriver, a chuck key, a custom tool, and the like. As a deterrence to theft, a lock arrangement (not shown) could be included to prevent the portable electronic device 102 from being removed from the sterilizable enclosure 2100 without a key (not shown). A pin 2312 is operatively attached to the carrier 2304 for concurrent rotation with the twist latch 2302.

Figure 30:
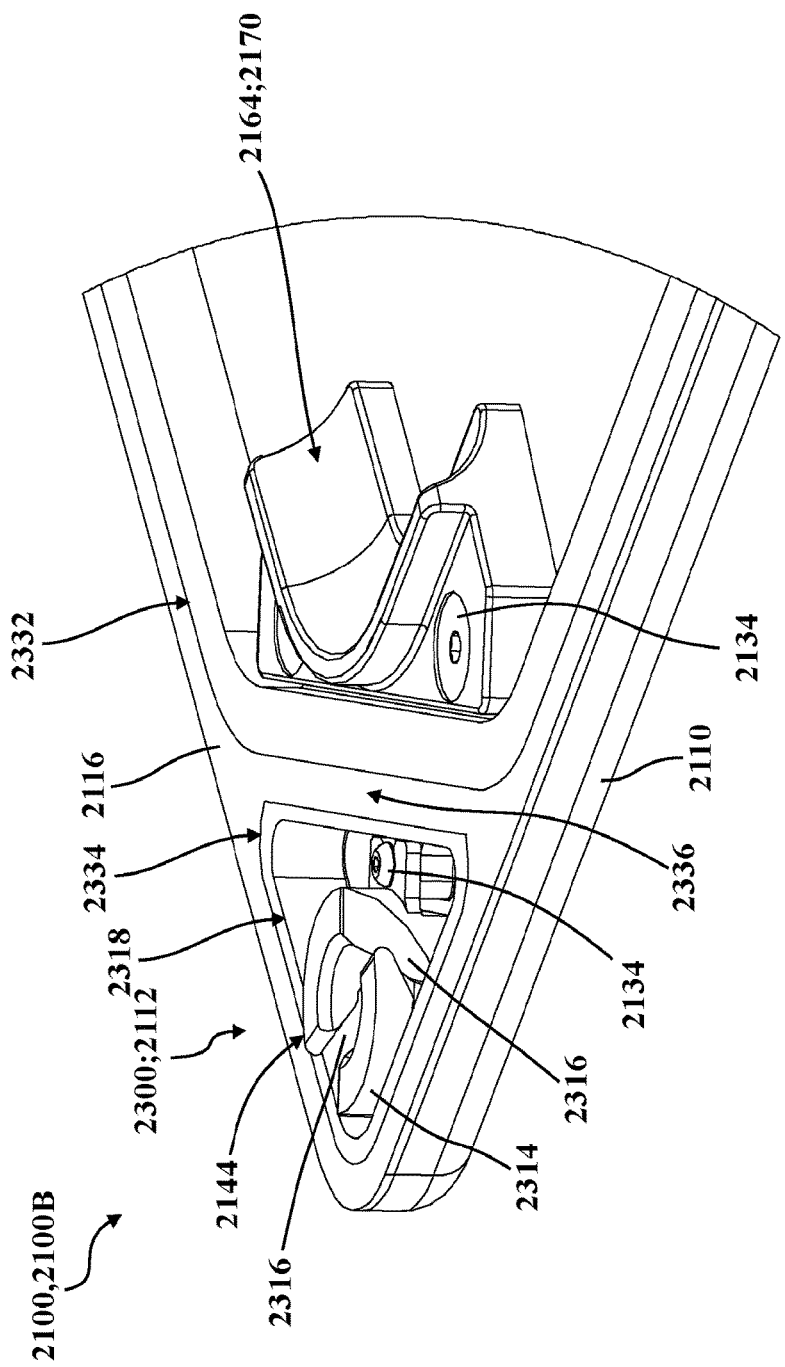
FIG. 30 is an enlarged partial perspective view of the base of the sterilizable enclosure taken from indicia 30 of FIG. 28.

In this embodiment, the second lock elements 2144 of the sterilizable enclosure 2100 each comprise a catch member 2314 in which one or more helical slots 2316 are defined (see FIG. 30). Here, each catch member 2314 operatively attached to the base 2110 via a fastener 2134, and is accommodated in a respective corner pocket 2318 formed in the base 2210 (see FIGS. 28 and 30), as described in greater detail below. The helical slots 2316 formed in the catch members 2314 are shaped to receive the respective pins 2312 of the first lock elements 2142.

Once the portable electronic device 102 is positioned in the bias elements 2164 defining the tray 2170 and attached to the base 2110, the frame 2106 is placed on top of the base 2110 and the portable electronic device 102. Here, each of the pins 2312 is positioned entering into one of the respective helical slots 2316. Subsequent rotation of each of the twist latches 2302, such as via a screwdriver engaging in the respective drive formations 2310, causes the respective carrier 2304 and pin 2312 to rotate. Here, because the pin 2312 is positioned in the helical slots 2316, rotation of the carrier 2304 causes the pin 2312 to traverse the helical slot 2316, thereby bringing the frame 2106 towards the base 2110 which, in turn, effects the capacitive coupling between the touchscreen interface 104 and the transparent panel 114 and engages the seal 2116 between the base 2110 and the frame 2106. It will be appreciated that the sterilizable enclosure 2100 is locked in the closed position 2100A via cooperation of the four lock mechanism 2112 of the corner lock arrangement 2300. Moreover, because of the configuration of the lock mechanisms 2112 in this embodiment, it will be appreciated that compression of the seal 2116 helps keep the sterilizable enclosure 2100 locked in the closed position 2100A in that reactive force from the compressed seal 2116 translated to the pin 2312 prevents the carrier 2304 and the twist latch 2302 from rotating freely. Other embodiments of the corner lock arrangement 2300 are contemplated. By way of non-limiting example, the embodiment of the sterilizable enclosure 2100 depicted in FIGS. 39 and 40 employs four lock mechanisms which are substantially similar to the lock mechanism 112 described in greater detail above in connection with the embodiment of the sterilizable enclosure 100 depicted in FIGS. 1-20C. Moreover, those having ordinary skill in the art will appreciate that the various lock mechanisms 112, 2112 described herein and depicted throughout the drawings could be interchanged for certain applications.

Figure 34:
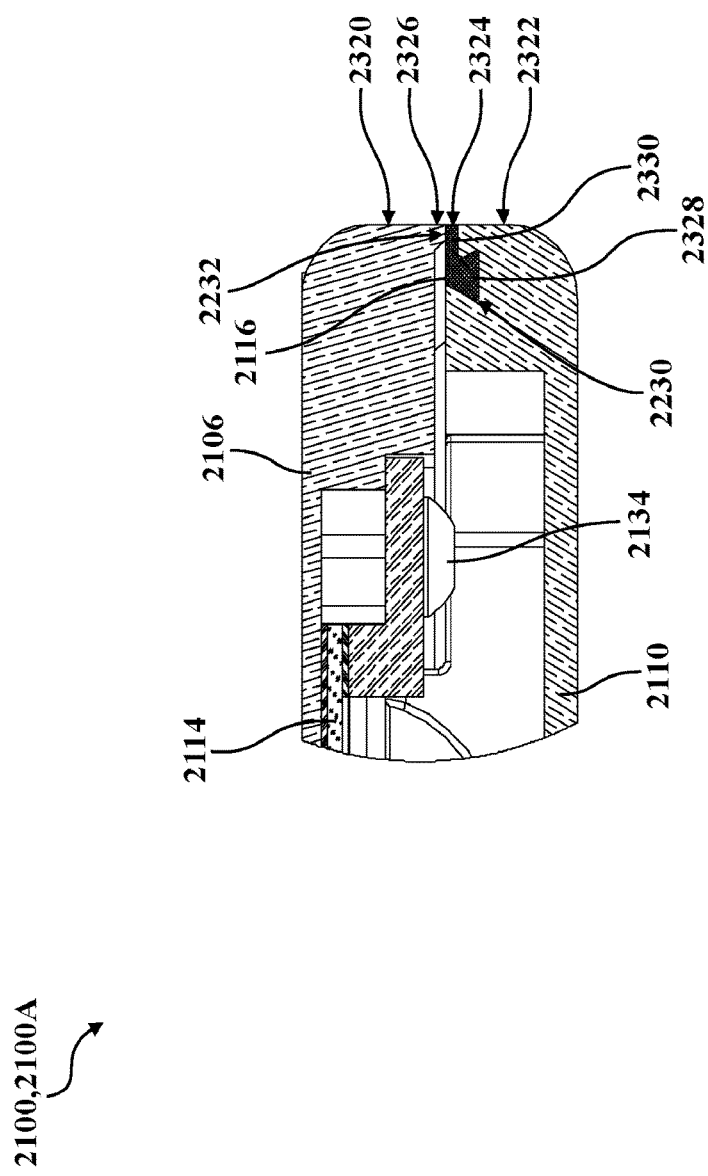
FIG. 34 is an enlarged partial sectional view of the sterilizable enclosure taken from indicia 34 of FIG. 33.

Referring now to FIG. 34, in this embodiment, the frame 2106 defines a frame periphery edge 2320, the base 2110 defines a base periphery edge 2322, and the seal 2116 defines a seal periphery edge 2324. As is best shown in FIG. 34, in this embodiment, when the sterilizable enclosure 2100 is in the closed position 2100A, the seal periphery edge 2324 is arranged adjacent to the frame periphery edge 2320 and the base periphery edge 2322. More specifically, the frame periphery edge 2320, the base periphery edge 2322, and the seal periphery edge 2324 are coincident when the sterilizable enclosure 2100 is in the closed position 2100A. As will be appreciated from the subsequent description below, this configuration helps prevent contaminants from being trapped between surfaces, edges, components, and the like, during use, thereby allowing the outer surface 2156 of the sterilizable enclosure 2100 to be effectively decontaminated without necessitating removal of the secured portable electronic device 102 (see FIG. 36). This may be advantageous for certain applications, such as where the sterilizable enclosure 102 is used in a hospital by a medical professional who visits different patients throughout the day without necessarily subjecting the sterilizable enclosure 2100 to more exhaustive decontamination procedures. Here, the medical professional could clean the sterilizable enclosure 2100 between patient visitations by, for example, using a disinfectant wipe to quickly clean the outer surface 2156 of the sterilizable enclosure 2100, in particular the seal periphery edge 2324, the frame periphery edge 2320, and the base periphery edge 2322. It will be appreciated that the seal periphery edge 2324 could extend beyond the frame periphery edge 2320 and the base periphery edge 2322 for certain applications. Because the seal periphery edge 2324 is aligned with the base periphery edge 2322 and the frame periphery edge 2320, micro-organisms are trapped at the outermost surface area of the sterilizable enclosure 2100 and, thus, can be effectively decontaminated for certain applications by manually wiping the external surface of the sterilizable enclosure 2100.

With continued reference to FIGS. 30, 31, 34, and 36, in one embodiment, the sterilizable enclosure 2100 further comprises an engagement element 2232 operatively attached to the frame 2106 which is shaped to engage the seal 2116 when the sterilizable enclosure 2100 is in the closed position 2100A. Here, the engagement element 2232 comprises an engagement periphery edge 2326 which is arranged adjacent to the seal periphery edge 2324. As is best shown in FIG. 34, because the engagement element 2232 is formed integrally with the frame 2106 in this embodiment, the engagement periphery edge 2326 forms part of the frame periphery edge 2320. In the representative embodiment illustrated in FIGS. 28-36, the engagement element 2232 has a generally trapezoidal cross-sectional profile and is shaped complimentarily to the seal 2116 so as to effect engagement with the seal 2116 in the closed position 2100A, as noted above.

Referring again to FIG. 34, in one embodiment, a channel 2230 is defined in the base 2110 spaced inwardly from the base periphery edge 2322 to accommodate at least a portion of the seal 2116. The seal 2116, in turn, comprises a channel portion 2328 shaped to be received in the channel 2230 formed in the base 2110, and an engagement portion 2330 extending from the channel portion 2328 to the seal periphery edge 2324. Here, at least a portion of the engagement portion 2330 of the seal 2116 is shaped to engage the frame 2106 when the sterilizable enclosure 2100 is in the closed position 2100A. The channel portion 2328 of the seal 2116 and the channel 2230 of the base 2110 each have a generally trapezoidal profile in the representative embodiment illustrated herein. This configuration helps retain the seal 2116 to the base 2110. However, other configurations of the seal 2116 and/or the channel 2230 are contemplated.

Figure 31:
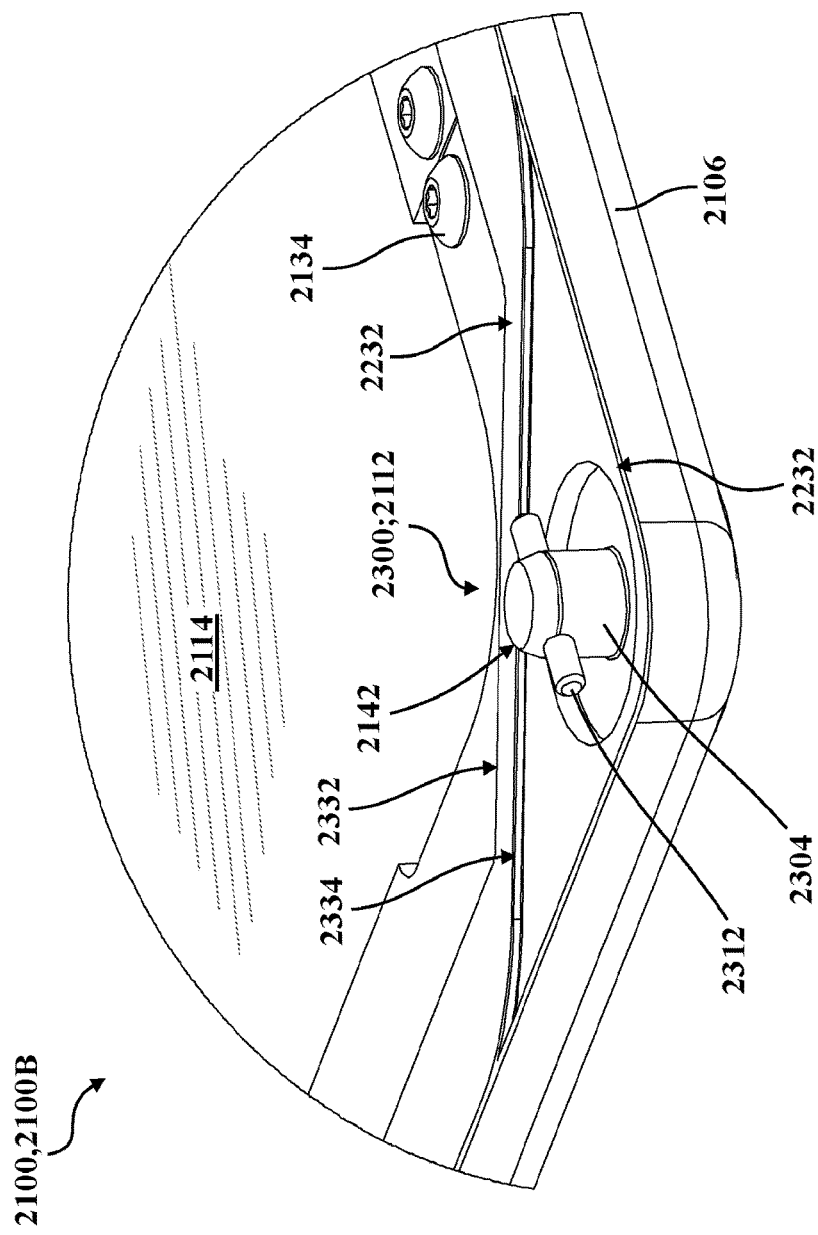
FIG. 31 is an enlarged partial perspective view of the frame of the sterilizable enclosure taken from indicia 31 of FIG. 29.
Figure 32:
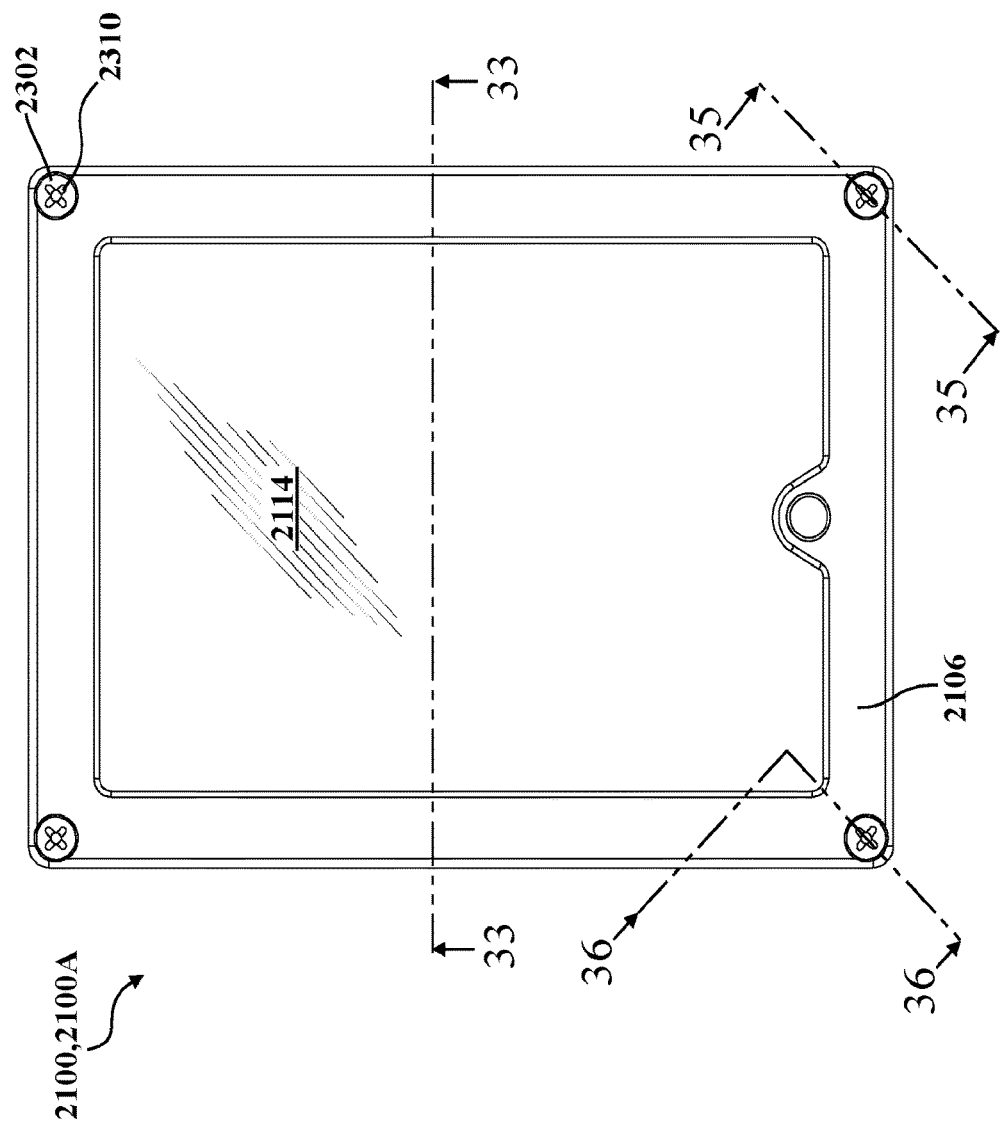
FIG. 32 is a top-side plan view of the sterilizable enclosure of FIGS. 28-31, shown in a closed position.
Figure 33:
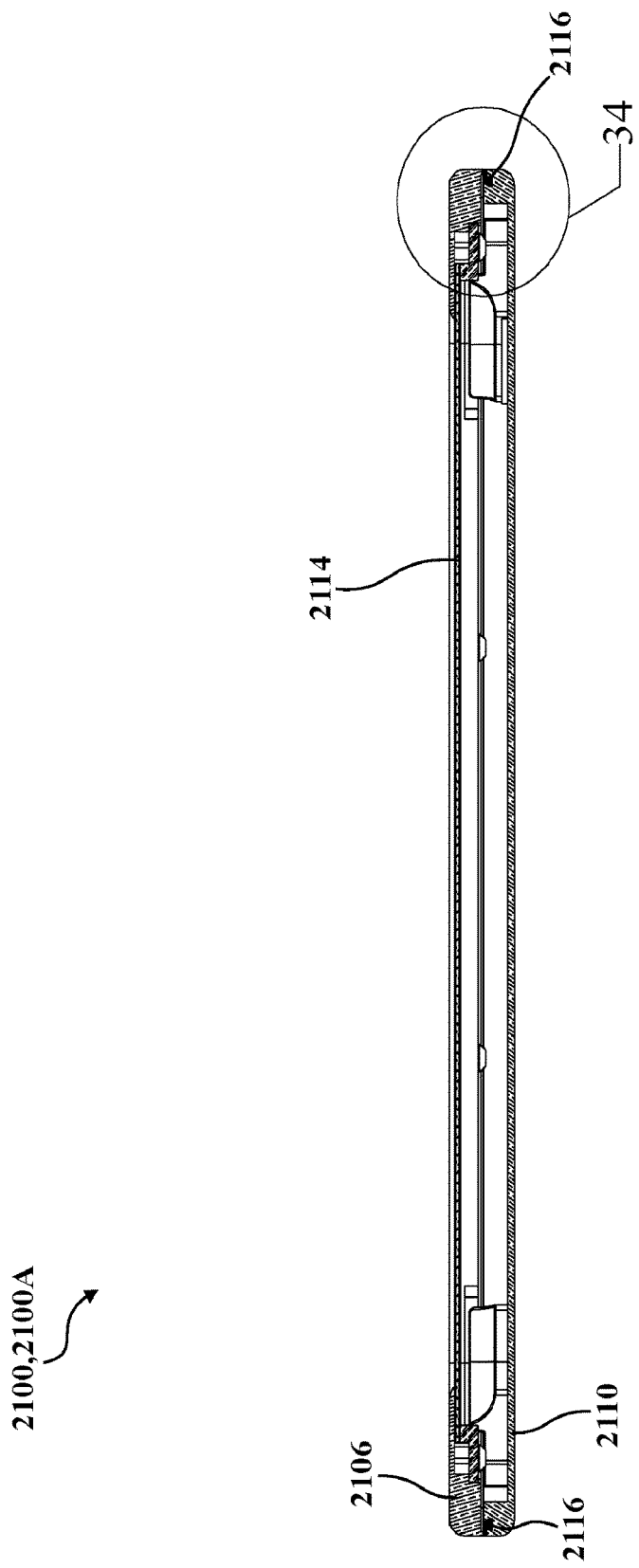
FIG. 33 is a sectional view taken along line 33-33 of FIG. 32.
Figure 36:
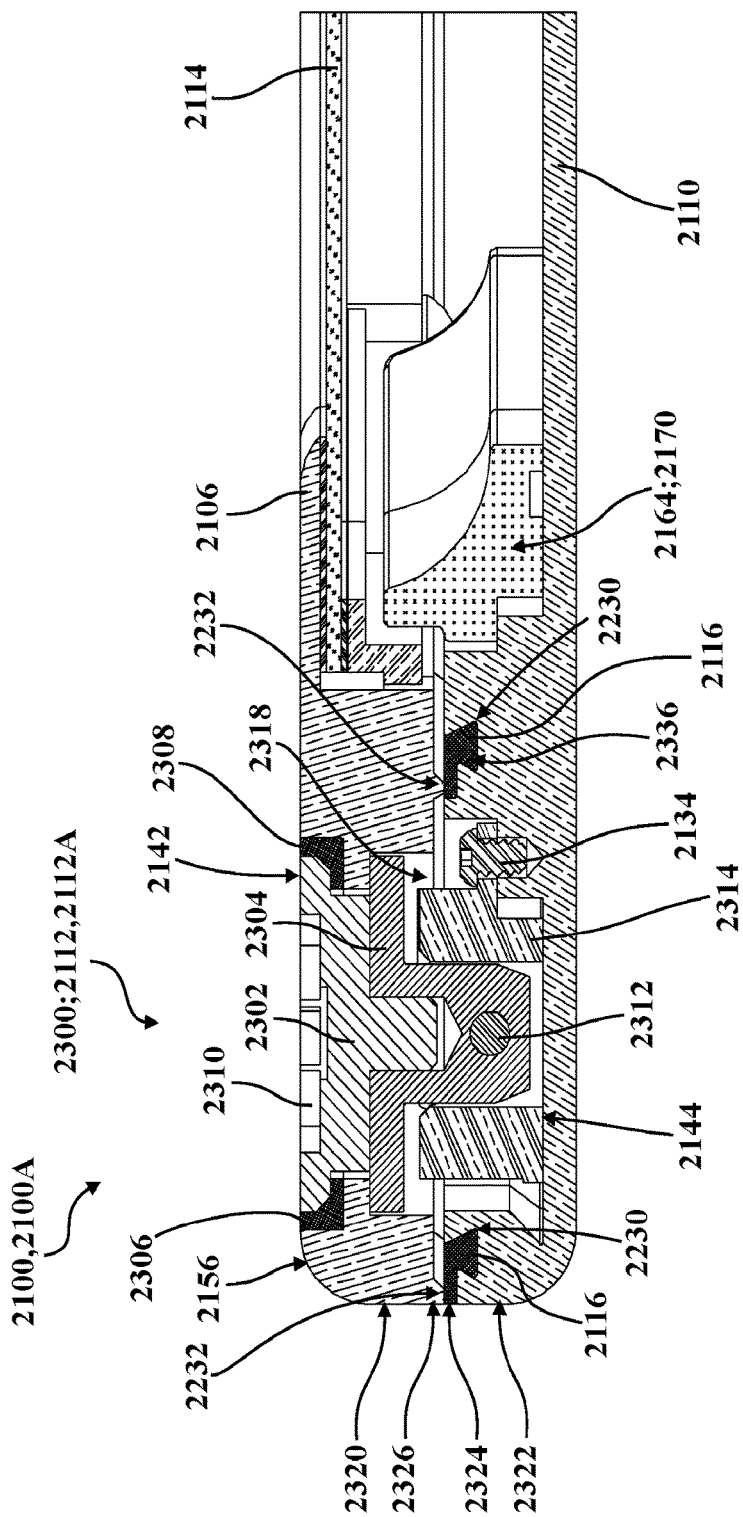
FIG. 36 is a sectional view taken along line 36-36 of FIG. 32.

Referring now to FIGS. 30, 31, and 36, in one embodiment, the seal 2116 defines a first seal region 2332 shaped to accommodate the portable electronic device 102, and a second seal region 2334 shaped to accommodate the lock mechanism 2112 and to partition the lock mechanism 2112 from the first seal region 2332. More specifically, in this embodiment, the seal 2116 comprises four integrally-formed seal leg elements 2336 which each define a discrete second seal region 2334 (see FIG. 30). The second seal regions 2334 are each shaped to partition one of the four lock mechanisms 2112 from the first seal region 2332. Here, each of the second seal regions 2334 has a generally triangular shape and encompasses the corner pockets 2318 in which the catch members 2314 are supported (see FIG. 30). Here too in this embodiment, the engagement element 2232 of the frame 2106 is shaped so as to engage the entire seal 2116, including the seal leg elements 2336, so as to isolate or otherwise partition the first seal regions 2332 from the second seal region 2334 (see FIG. 31). As shown in FIGS. 35 and 36, the entire seal 2116, including the seal leg elements 2336, has a commonly shaped cross-sectional profile. However, it will be appreciated that other configurations, shapes, profiles, and the like, are contemplated for the first and second seal regions 2332, 2334.

Partitioning the first seal region 2332 from the second seal regions 2334 helps ensure that contaminants do not come into contact with the secured portable electronic device 102 while, at the same time, allowing the outer surface 2156 to be effectively decontaminated without opening the sterilizable enclosure 2100. Moreover, while the sealing washers 2308 help prevent contaminants from approaching the corner pockets 2318, the partitioning afforded between the seal regions 2332, 2334 nevertheless ensures that contaminants do not enter the first seal region 2332. It will be appreciated that the partitioning afforded by the seal 2116 described above could be implemented into other embodiments, such as if the sterilizable enclosure were to employ internal hinges, living hinges, and the like, mounted within the corner pockets 2318 (not shown). Moreover, while the representative embodiment of the sterilizable enclosure 2100 illustrated in FIGS. 28-36 employs a single seal 2116, those having ordinary skill in the art will appreciate that more than one seal could be implemented, such as with an external seal configured to allow the use of a disinfectant wipe to quickly clean the seal periphery edge 2324, the frame periphery edge 2320, and the base periphery edge 2322 as noted above, and an internal seal defining the first seal region 2332 and formed as a separate component from the external seal, with internal hinges and/or lock mechanisms arranged between the external seal and the internal seal (not shown)

In this way, the embodiments of the sterilizable enclosure 100, 2100 described herein prevent both ingress and egress of contaminants to and from the secured portable electronic device 102, thereby significantly contributing to ease of cleaning, disinfecting, and maintaining a low number of contaminants on the outside of the enclosure 100, 2100, thereby affording increased opportunities for robust utilization of portable electronic devices 102 in industry. It will be appreciated that the sterilizable enclosures 100, 2100 enable medical professionals, such as nurses, doctors, emergency medical technicians, and the like, to utilize commercially-available, familiar portable electronic devices 102 in sterile environments without necessitating the use of complex, expensive, or otherwise unfamiliar devices or technology. Moreover, it will be appreciated that the sterilizable enclosures 2100 are reusable, serviceable, and compatible with conventional medical cleaning, decontamination, and disinfection equipment, chemicals, and procedures commonly utilized in the medical industry to ensure sterility. Thus, the sterilizable enclosures 100, 2100 maintain an aseptic environment for the secured portable electronic device 102 in that contaminants, such as pathogens, blood, tissue, and micro-organisms are prevented from passing to the secured portable electronic device 102 locked in the closed positions 100A, 2100A of the respective sterilizable enclosures 100, 2100. Similarly, the sterilizable enclosures 100, 2100 ensure that contaminants cannot leave the secured portable electronic device 102, thereby enabling existing decontamination and disinfection procedures to be performed after the sterilizable enclosures 100, 2100 are locked in the closed position 100A, 2100A which, in turn, facilitates aseptic use of the contaminated or otherwise non-sterile portable electronic device 102 in environments in which decontamination is required.

The sterilizable enclosures 100, 2100 could be used in: sterile fields during surgery; cadaver laboratories; clean rooms, including pharmaceutical and interplanetary spacecraft manufacturing; satellite manufacturing; decontamination areas; sterile inventory areas; patient rooms; hospital check-in areas; waiting rooms; nurses' stations; microbiology labs; field use by emergency medical technicians (EMTs); or any other area in which the sterilizable enclosures 100, 2100 may be advantageous. The portable electronic device 102 can provide great assistance in various work environments and the sterilizable enclosures 100, 2100 enable users to operate the portable electronic device 102 in these environments.

It will be further appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

Embodiments of the disclosure can be described with reference to the following numbered clauses, with specific features laid out in the dependent clauses:

I. A sterilizable enclosure for use in securing a portable electronic device having a touchscreen interface and for preventing ingress and egress of contaminants to and from the secured portable electronic device, said sterilizable enclosure comprising:
a frame comprising a frame periphery edge with said frame defining a window with a transparent panel operatively attached to said frame adjacent to said window and arranged to abut the touchscreen interface of the portable electronic device;
a base for being coupled to said frame and comprising a base periphery edge, wherein said base and said frame cooperate to define a closed position of said sterilizable enclosure in which the portable electronic device is secured between said base and said frame;
a seal comprising a seal periphery edge with said seal operatively attached to at least one of said base and said frame and arranged to be engaged between said base and said frame when said sterilizable enclosure is in said closed position so as to prevent ingress and egress of contaminants to and from the secured portable electronic device with said seal periphery edge arranged adjacent to said frame periphery edge and said base periphery edge.

II. The sterilizable enclosure as set forth in clause I, further comprising an engagement element operatively attached to the other of said base and said frame and shaped to engage said seal when said sterilizable enclosure is in said closed position.

III. The sterilizable enclosure as set forth in clause II, wherein said engagement element comprises an engagement periphery edge arranged adjacent to said seal periphery edge.

IV. The sterilizable enclosure as set forth in any one of the preceding clauses, wherein a channel is defined in said base spaced inwardly from said base periphery edge to accommodate at least a portion of said seal.

V. The sterilizable enclosure as set forth in clause IV, wherein said seal comprises a channel portion shaped to be received in said channel, and an engagement portion extending from said channel portion to said seal periphery edge with said engagement portion shaped to engage said frame in said closed position.

VI. The sterilizable enclosure as set forth in clause V, wherein said channel portion and said channel each have a generally trapezoidal profile.

VII. The sterilizable enclosure as set forth in any one of the preceding clauses, wherein said seal is a unitary once-piece component.

VIII. The sterilizable enclosure as set forth in any one of the preceding clauses, wherein said seal comprises a material with a melting point greater than 130 degrees celsius.

IX. The sterilizable enclosure as set forth in any one of the preceding clauses, further comprising a lock mechanism for selectively locking said sterilizable enclosure in said closed position, said lock mechanism comprising a first lock element rotatably coupled to one of said base and said frame, and a second lock element operatively attached to the other of said base and said frame arranged to engage said first lock element to lock said sterilizable enclosure in said closed position.

X. The sterilizable enclosure as set forth in clause IX, wherein said seal defines a first seal region shaped to accommodate the portable electronic device, and a second seal region shaped to accommodate said lock mechanism and to partition said lock mechanism from said first seal region.

XI. The sterilizable enclosure as set forth in clause X, further comprising four discrete lock mechanisms; and wherein said seal defines four discrete second seal regions each shaped to accommodate one of said lock mechanisms.

XII. The sterilizable enclosure as set forth in any one of the preceding clauses, wherein said transparent panel comprises an aluminosilicate material.

XIII. The sterilizable enclosure as set forth in any one of the preceding clauses, wherein said frame periphery edge, said base periphery edge, and said seal periphery edge are coincident when said sterilizable enclosure is in said closed position.

XIV. The sterilizable enclosure as set forth in any one of the preceding clauses, further comprising a bias mechanism operatively attached to said base to urge the touchscreen interface of the portable electronic device into abutment with said glass panel to enable a capacitive coupling between said glass panel and the touchscreen interface of the secured portable electronic device when said sterilizable enclosure is in said closed position.

XV. A sterilizable enclosure for use in securing a portable electronic device having a touchscreen interface and for preventing ingress and egress of contaminants to and from the secured portable electronic device, said sterilizable enclosure comprising:
a frame defining a window;
a base for being coupled to said frame, wherein said base and said frame cooperate to define a closed position of said sterilizable enclosure in which the portable electronic device is secured between said base and said frame;
a lock mechanism for selectively locking said sterilizable enclosure in said closed position;
a glass panel operatively attached to said frame adjacent to said window and arranged to abut the touchscreen interface of the portable electronic device when said sterilizable enclosure is locked in said closed position;
a seal operatively attached to at least one of said base and said frame and arranged to be engaged between said base and said frame when said sterilizable enclosure is locked in said closed position so as to prevent ingress and egress of contaminants to and from the secured portable electronic device; and
a biasing mechanism operatively attached to said base to urge the touchscreen interface of the portable electronic device into abutment with said glass panel to enable a capacitive coupling between said glass panel and the touchscreen interface of the secured portable electronic device when said sterilizable enclosure is in said closed position.

XVI. A sterilizable enclosure for use in securing a portable electronic device having a touchscreen interface and for preventing ingress and egress of contaminants to and from the secured portable electronic device, said sterilizable enclosure comprising:

a frame defining a window;

a base for being coupled to said frame, wherein said base and said frame cooperate to define a closed position of said sterilizable enclosure in which the portable electronic device is secured between said base and said frame;

a lock mechanism for selectively locking said sterilizable enclosure in said closed position, said lock mechanism comprising a lock element rotatably coupled to one of said base and said frame;

a glass panel operatively attached to said frame adjacent to said window and arranged to abut the touchscreen interface of the portable electronic device when said sterilizable enclosure is locked in said closed position; and a seal operatively attached to at least one of said base and said frame;

wherein rotation of said lock element of said lock mechanism from a first position to a second position urges said base and said frame towards each other to enable a capacitive coupling between said glass panel and the touchscreen interface of the secured portable electronic device and to engage said seal so as to prevent ingress and egress of contaminants to and from the secured portable electronic device.

XVII. The sterilizable enclosure as set forth in clause XVI, wherein said glass panel is arranged so that external tactile engagement of said glass panel is translated to an electrostatic field of the touchscreen interface of the secured portable electronic device when said sterilizable enclosure is locked in said closed position.

XVIII. The sterilizable enclosure as set forth in any one of clauses XVI through XVII, wherein said lock mechanism further comprises a second lock element; and wherein said lock elements cooperate to selectively lock said sterilizable enclosure in said closed position.

XIX. The sterilizable enclosure as set forth in any one of clauses XVI through XVIII, wherein said lock mechanism comprising said lock element rotatably coupled to one of said base and said frame further comprises a catch operatively attached to the other of said base and said frame arranged to engage said lock element when said lock element is in said second position.

XX. The sterilizable enclosure as set forth in clause XIX, wherein rotation of said lock element from said first position to said second position moves said lock mechanism between: an unlocked configuration wherein said lock element is disengaged from said catch such that said base and said frame can be moved out of said closed position to an opened position of said sterilizable enclosure; and a locked configuration wherein said lock element engages said catch such that said base and said frame are maintained in said closed position of said sterilizable enclosure.

XXI. The sterilizable enclosure as set forth in clause XX, wherein said lock element comprises a cam arranged such that rotation of said lock element towards said second position urges said frame towards said base.

XXII. The sterilizable enclosure as set forth in any one of clauses XVI through XXI, wherein said lock mechanism has an autoclave configuration wherein rotation of said lock element to a third position prevents said base and said frame from abutting each other.

XXIII. The sterilizable enclosure as set forth in any one of clauses XVI-XXII, wherein said base is pivotally coupled to said frame.

XXIV. A sterilizable enclosure for use in securing a portable electronic device having a touchscreen interface and for preventing ingress and egress of contaminants to and from the secured portable electronic device, said sterilizable enclosure comprising:

a frame defining a window with a transparent panel operatively attached to said frame adjacent to said window and arranged to abut the touchscreen interface of the portable electronic device;

a base for being coupled to said frame, wherein said base and said frame cooperate to define a closed position of said sterilizable enclosure in which the portable electronic device is secured between said base and said frame;

a seal operatively attached to one of said base and said frame and arranged to be engaged between said base and said frame when said sterilizable enclosure is in said closed position so as to prevent ingress and egress of contaminants to and from the secured portable electronic device;

a engagement element operatively attached to the other of said base and said frame and shaped to engage said seal when said sterilizable enclosure is in said closed position, wherein said seal and said engagement element each define a boundary between: a touch zone comprising first portions of said base and said frame, and a no-touch zone comprising second portions of said base and said frame; and an indicia configured to differentiate said first portions of said touch zone from said second portions of said no-touch zone to promote contact only within said first portions of said base and said frame of said sterilizable enclosure.

XXV. The sterilizable enclosure as set forth in clause XXIV, wherein said indicia is disposed on at least one of said first portions of said base and said frame defining said touch zone.

XXVI. The sterilizable enclosure as set forth in any one of clauses XXIV through XXV, wherein said indicia is disposed on at least one of said second portions of said base and said frame defining said no-touch zone.

XXVII. The sterilizable enclosure as set forth in clause XXVI, wherein a second indicia is disposed on at least one of said first portions of said base and said frame defining said touch zone.

XXVIII. The sterilizable enclosure as set forth in clause XXVII, wherein said indicia disposed on said second portions of said base and said frame defining said no-touch zone is a first color, and wherein said second indicia disposed on said first portions of said base and said frame defining said touch zone is a second color.

XXIX. The sterilizable enclosure as set forth in any one of clauses XXIV through XXVIII, wherein said indicia comprises text.

XXX. The sterilizable enclosure as set forth in any one of clauses XXIV through XXIX, wherein said touch zone comprises a frame touch surface area of said frame, and a base touch surface area of said base.

XXXI. The sterilizable enclosure as set forth in clause XXX, wherein said no-touch zone comprises a frame no-touch surface area of said frame separate from said frame touch surface area, and a base no-touch surface area of said base separate from said base touch surface area.

XXXII. The sterilizable enclosure as set forth in any one of clauses XXIV through XXXI, wherein an inner periphery of said seal defines said boundary between said touch zone and said no-touch zone.

XXXIII. A method of securing a portable electronic device having a touchscreen interface for use in a sterile environment, said method comprising:

providing a sterilizable enclosure comprising a frame defining a window with a transparent panel operatively attached to said frame adjacent to said window and arranged to abut the touchscreen interface of the portable electronic device, a base pivotally coupled to said frame, and a seal arranged to be engaged between said base and said frame when said sterilizable enclosure is in a closed position so as to prevent ingress and egress of contaminants to and from the secured portable electronic device;

providing a transfer device configured to shield at least a portion of said sterilizable enclosure from contaminants while holding said sterilizable enclosure in an opened position with said frame pivoted away from said base;

holding said sterilizable enclosure in said opened position with said transfer device;

inserting the portable electronic device into said sterilizable enclosure while in said opened position; and moving said transfer device away from said sterilizable enclosure to allow said frame to move towards said base into said closed position.

What is claimed is:

1. A sterilizable enclosure for use in securing a portable electronic device having a touchscreen interface and for preventing ingress and egress of contaminants to and from the secured portable electronic device, said sterilizable enclosure comprising:
    a frame comprising a frame periphery edge with said frame defining a window with a glass panel operatively attached to said frame adjacent to said window and arranged to abut the touchscreen interface of the portable electronic device;
    a base for being coupled to said frame and comprising a base periphery edge, wherein said base and said frame cooperate to define a closed position of said sterilizable enclosure in which the portable electronic device is secured between said base and said frame;
    a seal comprising a seal periphery edge with said seal operatively attached to at least one of said base and said frame and arranged to be engaged between said base and said frame when said sterilizable enclosure is in said closed position so as to prevent ingress and egress of contaminants to and from the secured portable electronic device with said seal periphery edge arranged adjacent to said frame periphery edge and said base periphery edge; and
    a biasing mechanism operatively attached to said base and spaced inwardly of the base periphery edge to urge the touchscreen interface of the portable electronic device into abutment with said glass panel to enable a capacitive coupling between said glass panel and the touchscreen interface of the secured portable electronic device when said sterilizable enclosure is in said closed position.

2. The sterilizable enclosure as set forth in claim 1, further comprising an engagement element operatively attached to the other of said base and said frame and shaped to engage said seal when said sterilizable enclosure is in said closed position.

3. The sterilizable enclosure as set forth in claim 2, wherein said engagement element comprises an engagement periphery edge arranged adjacent to said seal periphery edge.

4. The sterilizable enclosure as set forth in claim 1, wherein a channel is defined in said base spaced inwardly from said base periphery edge to accommodate at least a portion of said seal.

5. The sterilizable enclosure as set forth in claim 4, wherein said seal comprises a channel portion shaped to be received in said channel, and an engagement portion extending from said channel portion to said seal periphery edge with said engagement portion shaped to engage said frame in said closed position.

6. The sterilizable enclosure as set forth in claim 5, wherein said channel portion and said channel each have a generally trapezoidal profile.

7. The sterilizable enclosure as set forth in claim 1, wherein said seal is a unitary once-piece component.

8. The sterilizable enclosure as set forth claim 1, wherein said seal comprises a material with a melting point greater than 130 degrees celsius.

9. The sterilizable enclosure as set forth in claim 1, further comprising a lock mechanism for selectively locking said sterilizable enclosure in said closed position, said lock mechanism comprising a first lock element rotatably coupled to one of said base and said frame, and a second lock element operatively attached to the other of said base and said frame arranged to engage said first lock element to lock said sterilizable enclosure in said closed position.

10. The sterilizable enclosure as set forth in claim 9, wherein said seal defines a first seal region shaped to accommodate the portable electronic device, and a second seal region shaped to accommodate said lock mechanism and to partition said lock mechanism from said first seal region.

11. The sterilizable enclosure as set forth in claim 10, further comprising four discrete lock mechanisms; and
    wherein said seal defines four discrete second seal regions each shaped to accommodate one of said lock mechanisms.

12. The sterilizable enclosure as set forth claim 1, wherein said glass panel comprises an aluminosilicate material.

13. The sterilizable enclosure as set forth in claim 1, wherein said frame periphery edge, said base periphery edge, and said seal periphery edge are coincident when said sterilizable enclosure is in said closed position.

14. A sterilizable enclosure for use in securing a portable electronic device having a touchscreen interface and for preventing ingress and egress of contaminants to and from the secured portable electronic device, said sterilizable enclosure comprising:
    a frame defining a window;
    a base for being coupled to said frame and the base having a base periphery edge, wherein said base and said frame cooperate to define a closed position of said sterilizable enclosure in which the portable electronic device is secured between said base and said frame;
    a lock mechanism for selectively locking said sterilizable enclosure in said closed position;
    a glass panel operatively attached to said frame adjacent to said window and arranged to abut the touchscreen interface of the portable electronic device when said sterilizable enclosure is locked in said closed position;
    a seal operatively attached to at least one of said base and said frame and arranged to be engaged between said base and said frame when said sterilizable enclosure is locked in said closed position so as to prevent ingress and egress of contaminants to and from the secured portable electronic device; and a biasing mechanism operatively attached to said base and spaced inwardly of the base periphery edge to urge the touchscreen interface of the portable electronic device into abutment with said glass panel to enable a capacitive coupling between said glass panel and the touchscreen interface of the secured portable electronic device when said sterilizable enclosure is in said closed position.

15. The sterilizable enclosure as set forth in claim 14, further comprising an engagement element operatively attached to the other of said base and said frame and shaped to engage said seal when said sterilizable enclosure is in said closed position.

16. The sterilizable enclosure as set forth in claim 14, wherein said seal is a unitary once-piece component.

17. The sterilizable enclosure as set forth in claim 14, wherein said lock mechanism comprising a first lock element rotatably coupled to one of said base and said frame, and a second lock element operatively attached to the other of said base and said frame arranged to engage said first lock element to lock said sterilizable enclosure in said closed position.

18. The sterilizable enclosure as set forth in claim 14, wherein said seal defines a first seal region shaped to accommodate the portable electronic device and a second seal region shaped to accommodate said lock mechanism and to partition said lock mechanism from said first seal region.

19. The sterilizable enclosure as set forth in claim 18, further comprising four discrete lock mechanisms; and wherein said seal defines four discrete second seal regions each shaped to accommodate one of said lock mechanisms.

* * * * *